(12) United States Patent
Ledeboer et al.

(10) Patent No.: US 8,741,912 B2
(45) Date of Patent: Jun. 3, 2014

(54) DEAZAPURINES USEFUL AS INHIBITORS OF JANUS KINASES

(75) Inventors: Mark Ledeboer, Acton, MA (US); David Messersmith, Somerville, MA (US); Francois Maltais, Tewksbury, MA (US); Huai Gao, Lincoln, MA (US); Tiansheng Wang, Concord, MA (US); Jingrong Cao, Newton, MA (US); John Duffy, Northborough, MA (US); Gabriel Martinez-Botella, Wayland, MA (US); Cornelia Forster, Pelham, NH (US); Marion Wannamaker, Bolton, MA (US); Francesco Salituro, Marlboro, MA (US); Albert Pierce, Cambridge, MA (US); Luc Farmer, Foxboro, MA (US); Valerie Marone, Cambridge, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 724 days.

(21) Appl. No.: 11/732,845

(22) Filed: Apr. 5, 2007

(65) Prior Publication Data
US 2009/0088445 A1    Apr. 2, 2009

Related U.S. Application Data

(60) Provisional application No. 60/789,441, filed on Apr. 5, 2006.

(51) Int. Cl.
| | |
|---|---|
| C07D 487/04 | (2006.01) |
| A61K 31/519 | (2006.01) |
| A61P 35/00 | (2006.01) |
| A61P 29/00 | (2006.01) |
| A61P 37/06 | (2006.01) |
| A61P 25/16 | (2006.01) |
| A61P 25/28 | (2006.01) |

(52) U.S. Cl.
USPC ...................... 514/265.1; 544/280

(58) Field of Classification Search
USPC ...................... 544/280; 514/260.1
See application file for complete search history.

(56) References Cited

U.S. PATENT DOCUMENTS

| | | | | |
|---|---|---|---|---|
| 7,407,962 | B2 * | 8/2008 | Aronov et al. | 514/258.1 |
| 7,598,257 | B2 * | 10/2009 | Rodgers et al. | 514/265.1 |
| 2004/0214928 | A1 * | 10/2004 | Aronov et al. | 524/90 |
| 2005/0137201 | A1 | 6/2005 | Aronov et al. | |
| 2006/0003968 | A1 | 1/2006 | Green et al. | |
| 2006/0122213 | A1 | 6/2006 | Pierard et al. | |
| 2006/0183761 | A1 | 8/2006 | Ledeboer et al. | |
| 2007/0043063 | A1 | 2/2007 | Salituro et al. | |
| 2007/0135461 | A1 | 6/2007 | Rodgers et al. | |
| 2007/0135466 | A1 | 6/2007 | Ledeboer et al. | |
| 2007/0203142 | A1 | 8/2007 | Farmer et al. | |
| 2007/0207995 | A1 | 9/2007 | Salituro et al. | |

FOREIGN PATENT DOCUMENTS

| | | |
|---|---|---|
| WO | 99/65909 | 12/1999 |
| WO | 01/42246 | 6/2001 |
| WO | 2004/072063 | 8/2004 |
| WO | 2005/117909 | 12/2005 |
| WO | 2006/101783 | 9/2006 |
| WO | 2007/070514 | 6/2007 |
| WO | 2007/117494 | 10/2007 |

* cited by examiner

*Primary Examiner* — Susanna Moore
(74) *Attorney, Agent, or Firm* — Booyong S. Lim

(57) ABSTRACT

The present invention relates to compounds useful as inhibitors of protein kinases, particularly of JAK family kinases. The invention also provides pharmaceutically acceptable compositions comprising said compounds and methods of using the compositions in the treatment of various disease, conditions, or disorders. The compounds are generally represented by structural formula I or pharmaceutically acceptable salts thereof:

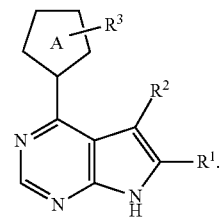

6 Claims, No Drawings

DEAZAPURINES USEFUL AS INHIBITORS OF JANUS KINASES

This application claims benefit of priority from U.S. Provisional Application 60/789,441, filed Apr. 5, 2006, which is herein incorporated by reference in its entirety.

TECHNICAL FIELD OF THE INVENTION

The present invention relates to compounds useful as inhibitors of Janus kinases (JAK). The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK3 has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Accordingly, there is a great need to develop compounds useful as inhibitors of protein kinases. In particular, it would be desirable to develop compounds that are useful as inhibitors of JAK family kinases.

SUMMARY OF THE INVENTION

It has now been found that compounds of this invention, and pharmaceutically acceptable compositions thereof, are effective as inhibitors of protein kinases, particularly the JAK family kinases. These compounds have the general formula I:

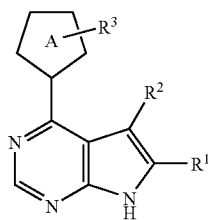

I or a pharmaceutically acceptable salt thereof, wherein Ring A, $R^1$, $R^2$ and $R^3$ are as defined herein.

These compounds, and pharmaceutically acceptable compositions thereof, are useful for treating or lessening the severity of a variety of disorders, including proliferative disorders, cardiac disorders, neurodegenerative disorders, autoimmune disorders, conditions associated with organ transplantation, inflammatory disorders, or immunologically mediated disorders in a patient.

The compounds and compositions provided by this invention are also useful for the study of JAK kinases in biological and pathological phenomena; the study of intracellular signal transduction pathways mediated by such kinases; and the comparative evaluation of new kinase inhibitors.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. If a substituent radical or structure is not identified or defined as "optionally substituted", the substituent radical or structure is unsubstituted. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and In yet other embodiments, aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle" or "cycloalkyl") refers to a hydrocarbon that is completely saturated or that contains one or more units of unsaturation, but which is not aromatic, that has a single point of attachment to the rest of the molecule, and wherein any individual ring in said bicyclic ring system has 3-7 members. Unless otherwise specified, the term "cycloaliphatic" refers to a monocyclic $C_3$-$C_8$ hydrocarbon or bicyclic $C_8$-$C_{12}$ hydrocarbon. Suitable cycloaliphatic groups include, but are not limited to, cycloalkyl, cycloalkenyl, and cycloalkynyl. Further examples of aliphatic groups include cyclopropyl, cyclobutyl, cyclopentyl, cyclopentenyl, cyclohexyl, cyclohexenyl, cycloheptyl, and cycloheptenyl.

The term "heterocycle", "heterocyclyl" or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle", "heterocyclyl" or "heterocyclic" group has three to fourteen ring members in which one or more ring members is a heteroatom independently selected from oxygen, sulfur, nitrogen, or phosphorus, and each ring in the system contains 3 to 7 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl, and anthracene.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definitions of $R^2$ and $R^4$ below. Other suitable substituents include: halogen; —R°; —OR°; —SR°; 1,2-methylenedioxy; 1,2-ethylenedioxy; phenyl (Ph) optionally substituted with R°; —O(Ph) optionally substituted with R°; —(CH$_2$)$_{1-2}$(Ph), optionally substituted with R°; —CH=CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°; —NR°NR°C(O)R°; —NR°NR°C(O)N(R°)$_2$; —NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°) R°; —C(NOR°)R°; —S(O)$_2$R°; —S(O)$_3$R°; —SO$_2$N(R°)$_2$; —S(O)R°; —NR°SO$_2$N(R°)$_2$; —NR°SO$_2$R°; —N(OR°)R°; —C(=NH)—N(R°)$_2$; or —(CH$_2$)$_{0-2}$NHC(O)R°; wherein each independent occurrence of R° is selected from hydrogen, optionally substituted $C_{1-6}$ aliphatic, an unsubstituted 5-6 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$ aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$ aliphatic groups of R* is unsubstituted.

In some embodiments, optional substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$ (Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$ aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R$^+$, or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

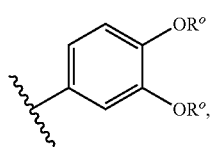

these two occurrences of R° are taken together with the oxygen atoms to which they are bound to form a fused 6-membered oxygen containing ring:

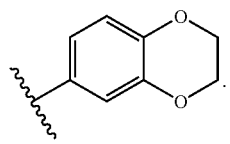 [SMILES: *c1ccc2c(c1)OCCO2 ; "."]

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below), represents substitution of the substituent at any substitutable position in any of the rings within the multiple ring system. For example, formula a represents possible substitution in any of the positions shown in formula b.

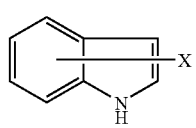

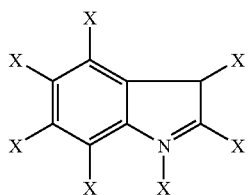

This also applies to multiple ring systems fused to optional ring systems (which would be represented by dotted lines). For example, in formula c, X is an optional substituent both for ring A and ring B.

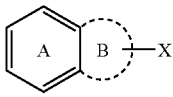

c

If, however, two rings in a multiple ring system each have different substituents drawn from the center of each ring, then, unless otherwise specified, each substituent only represents substitution on the ring to which it is attached. For example, in formula d, Y is an optionally substituent for ring A only, and X is an optional substituent for ring B only.

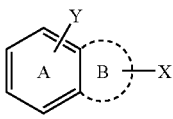

d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

Description of Compounds of the Invention

The present invention relates to a compound of formula I:

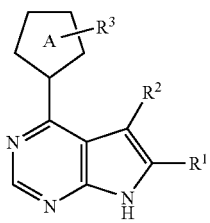

I or a pharmaceutically acceptable salt thereof, wherein:

Ring A is a 5-membered monocyclic heteroaryl having 1-4 heteroatoms selected from nitrogen, oxygen, or sulfur linked via a carbon atom to the deazapurine, provided that there is no more than one oxygen or sulfur heteroatom in Ring A, and if there is an oxygen or sulfur heteroatom, then there are no more than two nitrogen heteroatoms in Ring A, wherein Ring A is optionally substituted with up to 1-3 occurrences of $R^8$;

$R^1$ is —$(C_{1-2}$ aliphatic$)_p$-$R^4$, wherein $R^1$ is optionally substituted with 1-3 occurrences of $J^{R1}$;

$R^2$ is —$(C_{1-2}$ aliphatic$)_d$-$R^5$, wherein $R^2$ is optionally substituted with 1-3 occurrences of $J^{R2}$;

p and d are each independently 0 or 1;

$R^4$ is H, halogen, CN, $NH_2$, $NO_2$, $CF_3$, $C_{1-4}$ aliphatic, cyclopropyl, $NCH_3$, $OCH_3$, —C(=O)$NH_2$, —C(=O)$CH_3$, —NC(=O)$CH_3$, or OH;

$R^5$ is H, halogen, CN, $NH_2$, $NO_2$, $CF_3$, $C_{1-4}$ aliphatic, cyclopropyl, $NCH_3$, $OCH_3$, —C(=O)$NH_2$, —C(=O)$CH_3$, —NC(=O)$CH_3$, or OH;

each $J^{R1}$ is independently selected from halogen, $OCH_3$, OH, $NO_2$, $NH_2$, $SCH_3$, $NCH_3$, CN, or unsubstituted $C_{1-2}$ aliphatic; or two $J^{R1}$, together with the carbon to which they are attached, form a cyclopropyl ring or C=O;

each $J^{R2}$ is independently selected from halogen, $OCH_3$, OH, $NO_2$, $NH_2$, $SCH_3$, $NCH_3$, CN, or unsubstituted $C_{1-2}$ aliphatic; or two $J^{R2}$, together with the carbon to which they are attached, form a cyclopropyl ring or C=O;

$R^3$ is —$(U)_m$—X;

U is a $C_{1-6}$ aliphatic, wherein up to two methylene units are optionally and independently replaced by $G^U$ and wherein U is optionally substituted with 1-4 $J^U$;

$G^U$ is —NH—, —$NR^6$—, —O—, —S—, —$CO_2$—, —OC(O)—, —C(O)CO—, —C(O)—, —C(O)NH—, —C(O)$NR^6$—, —NC(=N—CN)N—, —NHCO—, —$NR^6$CO—, —NHC(O)O—, —$NR^6$C(O)O—, —$SO_2$NH—, —$SO_2NR^6$—, —$NHSO_2$—, —$NR^6SO_2$—, —NHC(O)NH—, —$NR^6$C(O)NH—, —NHC(O)$NR^6$—, —$NR^6$C(O)$NR^6$, —OC(O)NH—, —OC(O)$NR^6$—, —$NHSO_2$NH—, —$NR^6SO_2$NH—, —$NHSO_2NR^6$—, —$NR^6SO_2NR^6$—, —SO—, or —$SO_2$—;

$R^6$ is $C_{1-6}$ aliphatic or a $C_{3-10}$ cycloaliphatic; or two $R^6$ groups, together with the atom to which they are attached, optionally form a 3-7 membered cycloaliphatic or heterocyclyl, wherein said aliphatic, cycloaliphatic or heterocyclyl is optionally substituted with R", —OR", —SR", —$NO_2$, —$CF_3$, —CN, —$CO_2$R", —COR", OCOR", CONHR", or NHCOR", wherein R" is H or an unsubstituted $C_{1-6}$ aliphatic;

m is 0 or 1;

X is H, halogen, CN, $NO_2$, S(O)R, $SO_2$R, or a group selected from a $C_{1-6}$ aliphatic, a $C_{3-10}$ cycloaliphatic, a $C_{6-10}$ aryl, a 5-10 membered heteroaryl, or a 5-10 membered heterocyclyl, wherein said group is optionally substituted with 1-4 $J^X$;

R is an optionally substituted group selected from a $C_{1-6}$ aliphatic, a $C_{3-10}$ cycloaliphatic, a $C_{6-10}$ aryl, a 5-10 membered heteroaryl, or a 5-10 membered heterocyclyl, wherein R is independently and optionally substituted with 1-6 occurrences of $J^R$;

each $J^R$ is independently selected from halogen, L, -$(L_n)$-R', -$(L_n)$-N(R')$_2$, -$(L_n)$-SR', -$(L_n)$-OR', -$(L_n)$-$(C_{3-10}$ cycloaliphatic), -$(L_n)$-$(C_{6-10}$ aryl), -$(L_n)$-(5-10 membered heteroaryl), -$(L_n)$-(5-10 membered heterocyclyl), oxo, $C_{1-4}$haloalkoxy, $C_{1-4}$haloalkyl, -$(L_n)$-$NO_2$, -$(L_n)$-CN, -$(L_n)$-OH, -$(L_n)$-$CF_3$, —$CO_2$R', —$CO_2$H, —COR', —COH, —OC(O)R', —C(O)NHR', C(O)N(R')$_2$, —NHC(O)R', or NR'C(O)R'; or two $J^R$ groups, on the same substituent or different substituents, together with the atom(s) to which each $J^R$ group is bound, form a 5-7 membered saturated, unsaturated, or partially saturated ring;

each $J^U$ is independently selected from halogen, L, -$(L_n)$-R'- $(L_n)$-N(R')$_2$, -$(L_n)$-SR', -$(L_n)$-OR', -$(L_n)$-$(C_{3-10}$ cycloaliphatic), -$(L_n)$-$(C_{6-10}$ aryl), -$(L_n)$-(5-10 membered heteroaryl), -(L$_n$)-(5-10 membered heterocyclyl), oxo, C$_{1-4}$haloalkoxy, C$_{1-4}$haloalkyl, -(L$_n$)-NO$_2$, -(L$_n$)-CN, -(L$_n$)-OH, -(L$_n$)-CF$_3$, —CO$_2$R', —CO$_2$H, —COR', —COH, —OC(O)R', —C(O)NHR', C(O)N(R')$_2$, —NHC(O)R', or NR'C(O)R'; or two J$^U$ groups, on the same substituent or different substituents, together with the atom(s) to which each J$^U$ group is bound, form a 5-7 membered saturated, unsaturated, or partially saturated ring;

each J$^X$ is independently selected from halogen, L, -(L$_n$)-R',-(L$_n$)-N(R')$_2$, -(L$_n$)-SR', -(L$_n$)-OR', -(L$_n$)-(C$_{3-10}$ cycloaliphatic), -(L$_n$)-(C$_{6-10}$ aryl), -(L$_n$)-(5-10 membered heteroaryl), -(L$_n$)-(5-10 membered heterocyclyl), oxo, C$_{1-4}$haloalkoxy, C$_{1-4}$haloalkyl, -(L$_n$)-NO$_2$, -(L$_n$)-CN, -(L$_n$)-OH, -(L$_n$)-CF$_3$, —CO$_2$R', —CO$_2$H, —COR', —COH, —OC(O)R', —C(O)NHR', C(O)N(R')$_2$, —NHC(O)R', or NR'C(O)R'; or two J$^X$ groups, on the same substituent or different substituents, together with the atom(s) to which each J$^X$ group is bound, form a 5-7 membered saturated, unsaturated, or partially saturated ring;

each L is independently a C$_{1-6}$ aliphatic wherein up to three methylene units are replaced by —NH—, —NR$^7$—, —O—, —S—, —CO$_2$, —OC(O)—, —C(O)CO—, —C(O)—, —C(O)NH—, —C(O)NR$^7$—, —NC(=N—CN)N, —NHCO—, —NR$^7$CO—, —NHC(O)O—, —NR$^7$C(O)O—, —SO$_2$NH—, —SO$_2$NR$^7$—, —NHSO$_2$—, —NR$^7$SO$_2$—, —NHC(O)NH—, —NR$^7$C(O)NH—, —NHC(O)NR$^7$—, —NR$^7$C(O)NR$^7$, —OC(O)NH—, —OC(O)NR$^7$—, —NHSO$_2$NH—, —NR$^7$SO$_2$NH—, —NHSO$_2$NR$^7$—, —NR$^7$SO$_2$NR$^7$—, —SO—, or —SO$_2$—;

each n is independently 0 or 1;

each R' is independently H or C$_{1-6}$ aliphatic; or two R' groups, together with the atom to which they are attached, optionally form a 3-6 membered cycloaliphatic or heterocyclyl, wherein said aliphatic, cycloaliphatic or heterocyclyl is optionally substituted with R*, —OR*, —SR*, —NO$_2$, —CF$_3$, —CN, —CO$_2$R*, —COR*, OCOR*, NHCOR*, wherein R* is H or C$_{1-6}$ aliphatic;

R$^7$ is selected from C$_{1-6}$ aliphatic, C$_{3-10}$ cycloaliphatic, C$_{6-10}$ aryl, 5-10 membered heteroaryl, or 5-10 membered heterocyclyl; or two R$^7$ groups, on the same substituent or different substituents, together with the atom(s) to which each R$^6$ group is bound, form a 3-8 membered heterocyclyl;

each R$^8$ is independently —(C$_{1-3}$ aliphatic)$_y$-R$^9$, wherein R$^8$ is optionally substituted with 1-5 occurrences of J$_{R8}$;

each y is independently 0 or 1;

R$^9$ is halogen, CN, NH$_2$, NO$_2$, CF$_3$, C$_{1-4}$ aliphatic, cyclopropyl, NHR$^{10}$, N(R$^{10}$)$_2$, OR$^{10}$, C(O)OR$^{10}$, —C(O)NH$_2$, —C(O)R$^{10}$, —NC(O)R$^{10}$, or OH;

R$^{10}$ is C$_{1-4}$ aliphatic;

each J$^{R8}$ is independently selected from halogen, OCH$_3$, OH, NO$_2$, NH$_2$, SCH$_3$, NCH$_3$, CN, or unsubstituted C$_{1-2}$aliphatic; or two J$^{R8}$, together with the carbon to which they are attached, form a cyclopropyl ring or C=O;

provided that said compound is not

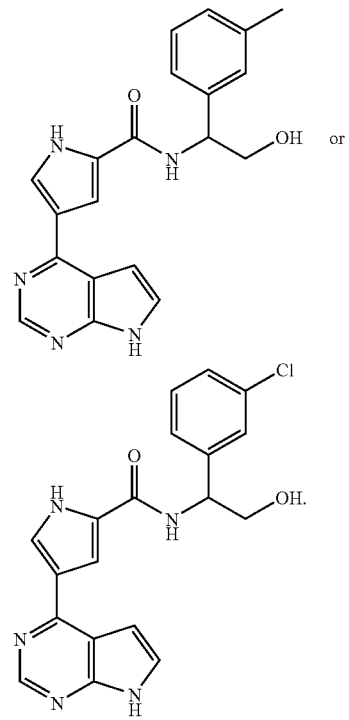

In one embodiment, R$^1$ is H, halogen or C$_{1-4}$ aliphatic. In a further embodiment, R$^1$ is H or halogen. In yet a further embodiment, R$^1$ is H.

In one embodiment, R$^2$ is H, halogen or C$_{1-4}$ aliphatic. In a further embodiment, R$^2$ is H, Cl, F or CH$_3$. In yet a further embodiment, R$^2$ is H.

In another embodiment, both R$^1$ and R$^2$ are H.

In one embodiment, Ring A is selected from the following:

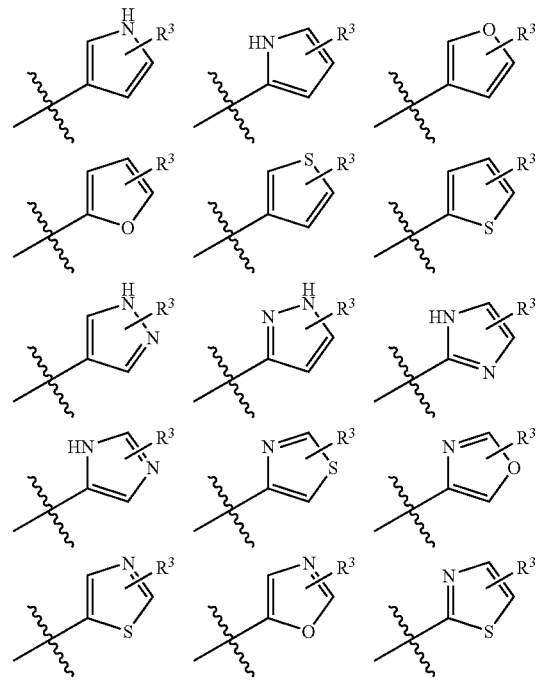

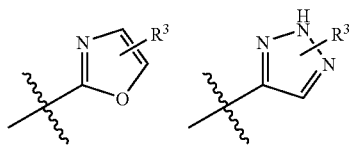

wherein Ring A is optionally substituted with 1-3 occurrences of R⁸.

In a further embodiment, Ring A is selected from the following:

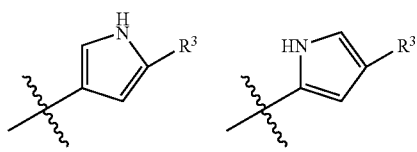
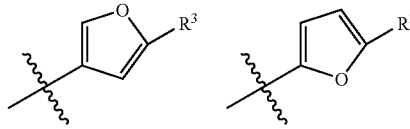
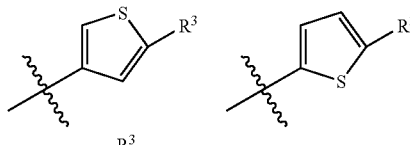
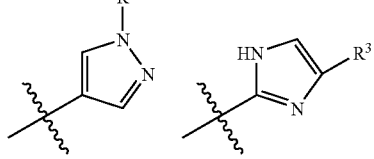
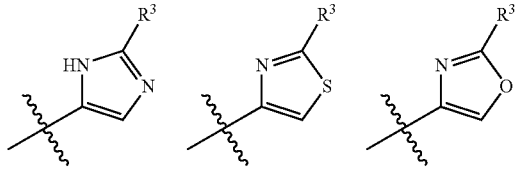
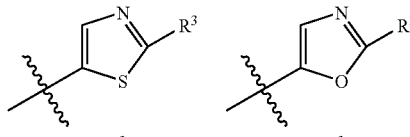
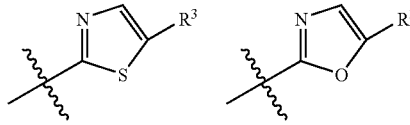
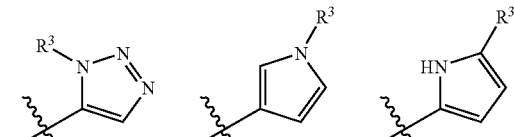
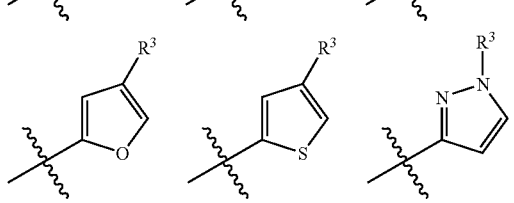

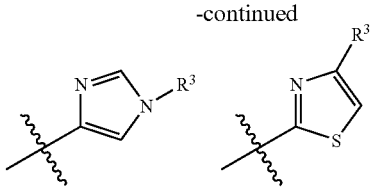
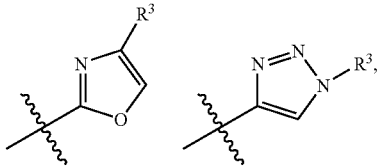

wherein Ring A is optionally substituted with 1-3 occurrences of R⁸.

In yet a further embodiment, Ring A is selected from the following:

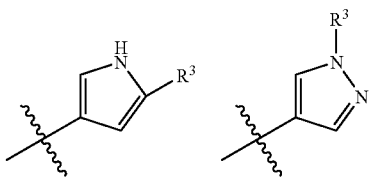
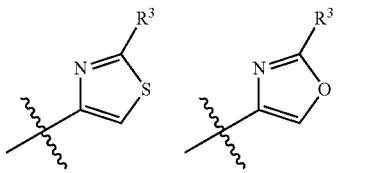
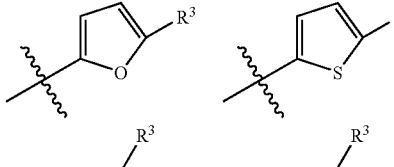
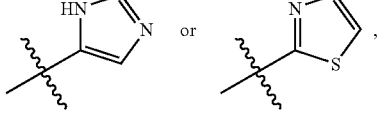

or

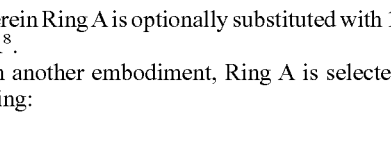, wherein Ring A is optionally substituted with 1-3 occurrences of R⁸.

In another embodiment, Ring A is selected from the following:

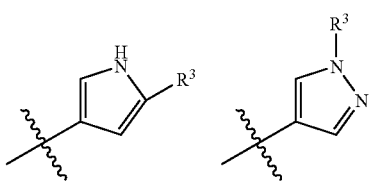
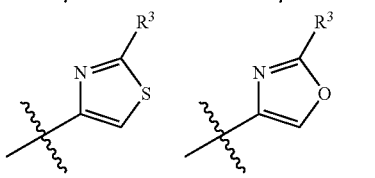

-continued

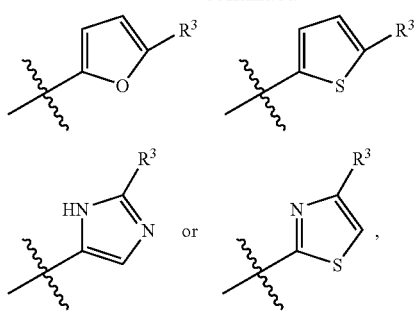

In another embodiment, Ring A is selected from the following:

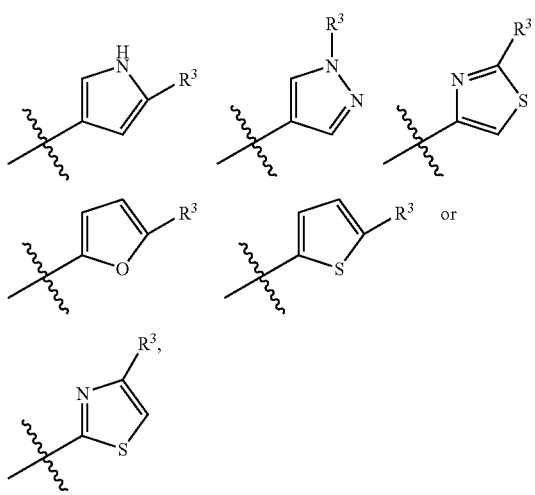

wherein Ring A is optionally substituted with 1-3 occurrences of $R^8$.

In another embodiment, Ring A is selected from the following:

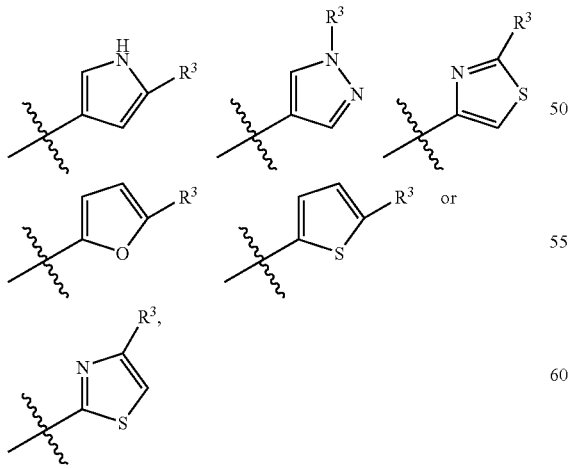

wherein Ring A is optionally substituted with 1-3 occurrences of $R^8$, and $R^1$ and $R^2$ are both H.

In another embodiment, Ring A is selected from the following:

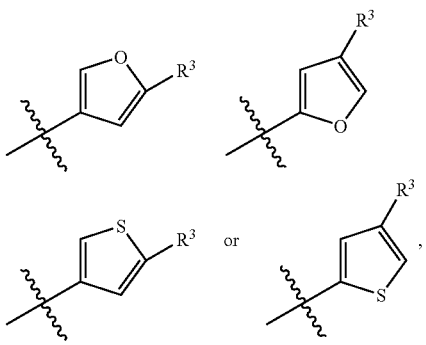

wherein Ring A is optionally substituted with 1-3 occurrences of $R^8$.

In another embodiment, Ring A is selected from the following:

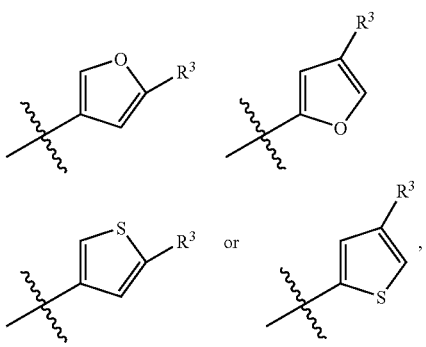

wherein Ring A is optionally substituted with 1-3 occurrences of $R^8$, and $R^1$ and $R^2$ are both H.

In another embodiment, Ring A is selected from the following:

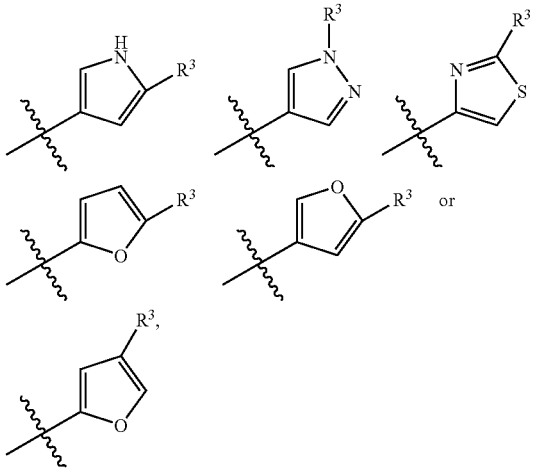

wherein Ring A is optionally substituted with 1-3 occurrences of $R^8$.

In another embodiment, Ring A is selected from the following:

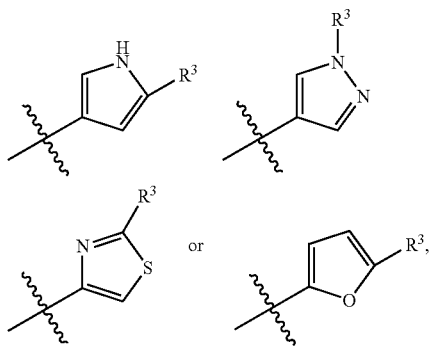

wherein Ring A is optionally substituted with 1-3 occurrences of $R^8$.

In one embodiment, Ring A is unsubstituted by $R^8$. In another embodiment, Ring A is substituted by one occurrence of $R^8$ and $R^8$ is halogen.

In one embodiment, $R^3$ is not H.

In another embodiment, m is 1 and U is selected from C(O)NH, C(O)NR$^6$, NHC(O), NR$^6$C(O), C(O), C(O)O, C(O)NH(CH$_2$)$_{1-3}$, C(O)NR$^6$(CH$_2$)$_{1-3}$, NHC(O)(CH$_2$)$_{1-3}$, NR$^6$C(O)(CH$_2$)$_{1-3}$, C(O)(CH$_2$)$_{1-3}$, C(O)O(CH$_2$)$_{1-3}$, (CH$_2$)$_{1-3}$C(O)NH, (CH$_2$)$_{1-3}$C(O)NR$^6$, (CH$_2$)$_{1-3}$NHC(O), (CH$_2$)$_{1-3}$NR$^6$C(O), (CH$_2$)$_{1-3}$C(O) or (CH$_2$)$_{1-3}$C(O)O. In a further embodiment, m is 1 and U is selected from C(O)NH, C(O)NR$^6$, NHC(O), NR$^6$C(O), C(O), C(O)O, C(O)NHCH$_2$, C(O)NR$^6$CH$_2$, NHC(O)CH$_2$, NR$^6$C(O)CH$_2$, C(O)CH$_2$, C(O)OCH$_2$, CH$_2$C(O)NH, CH$_2$C(O)NR$^6$, CH$_2$NHC(O), CH$_2$NR$^6$C(O), CH$_2$C(O) or CH$_2$C(O)O. In yet a further embodiment, m is 1 and U is selected from C(O)NH, C(O)NR$^6$, NHC(O), NR$^6$C(O), C(O), C(O)O, C(O)NHCH$_2$, C(O)NR$^6$CH$_2$, NHC(O)CH$_2$, NR$^6$C(O)CH$_2$, C(O)CH$_2$, C(O)OCH$_2$, CH$_2$C(O)NH, CH$_2$C(O)NR$^6$, CH$_2$NHC(O), CH$_2$NR$^6$C(O), CH$_2$C(O) or CH$_2$C(O)O. In yet a further embodiment, m is 1 and U is selected from C(O)NH, C(O)NR$^6$, NHC(O), NR$^6$C(O), C(O), C(O)NHCH$_2$, C(O)NR$^6$CH$_2$, NHC(O)CH$_2$ or NR$^6$C(O)CH$_2$.

In another embodiment, $R^6$ is $C_{1-4}$ aliphatic optionally substituted with —OH, —OCH$_3$, —SH, —SCH$_3$, —CF$_3$, —CN, —CO$_2$H, —CO$_2$CH$_3$, NHCOH, NHCOCH$_3$, CONH$_2$ or CONHCH$_3$. In a further embodiment, $R^6$ is $C_{1-3}$ aliphatic optionally substituted with —OH, —CF$_3$ or —CN.

In another embodiment, m is 0 and U is absent.

In another embodiment, X is a group selected from a $C_{1-6}$ aliphatic, a $C_{3-7}$ cycloaliphatic, a $C_{6-10}$ aryl, a 5-8 membered heteroaryl, or a 5-8 membered heterocyclyl, wherein said group is optionally substituted with 1-4 $J^X$. In a further embodiment, X is a group selected from a $C_{1-6}$ aliphatic, a $C_{3-6}$ cycloaliphatic, phenyl, a 5-6 membered heteroaryl, or a 5-7 membered heterocyclyl, wherein said group is optionally substituted with 1-4 $J^X$. In yet a further embodiment, X is $C_{1-4}$ straight or branched alkyl, $C_{2-4}$ straight or branched alkenyl, $C_{2-4}$ straight or branched alkynyl, cyclopropyl, cyclobutyl, cyclopentyl, cyclohexyl, phenyl, pyridyl, pyrimidinyl, pyrrolyl, piperindinyl, pyrrolidinyl, dihydro-1H-pyrrolyl, tetrahydro-1H-pyranyl, tetrahydrofuranyl, wherein said group is optionally substituted with 1-4 $J^X$. In another embodiment, X is not an optionally substituted $C_{6-10}$ aryl. In a further embodiment, X is not an optionally substituted phenyl.

In one embodiment, each $J^X$ is independently selected from halogen, R', -(L$_n$)-N(R')$_2$, -(L$_n$)-SR', -(L$_n$)-OR', -(L$_n$)-(C$_{3-6}$ cycloaliphatic), oxo, $C_{1-4}$ haloalkyl, -(L$_n$)-CN, -(L$_n$)-OH, -(L$_n$)-CF$_3$, —CO$_2$R', —CO$_2$H, —COR', —COH, —OC(O)R', —C(O)NHR', or —NC(O)R'; or two $J^X$ groups, on the same substituent or different substituents, together with the atom(s) to which each $J^X$ group is bound, form a 5-7 membered saturated, unsaturated, or partially saturated ring. In a further embodiment, each $J^X$ is independently selected from $C_{1-4}$ aliphatic, $C_{3-7}$ cycloaliphatic, halogen, (CH$_2$)$_{0-3}$OH, (CH$_2$)$_{0-3}$OCH$_3$, (CH$_2$)$_{0-3}$OCH$_2$CH$_3$, oxo, (CH$_2$)$_{0-3}$NH$_2$, (CH$_2$)$_{0-3}$NHCH$_3$, (CH$_2$)$_{0-3}$N(CH$_3$)$_2$, (CH$_2$)$_{0-3}$SH, (CH$_2$)$_{0-3}$SCH$_3$, (CH$_2$)$_{0-3}$SCH$_2$CH$_3$, (CH$_2$)$_{0-3}$CN, (CH$_2$)$_{0-3}$CF$_3$, CO$_2$H, —CO$_2$CH$_3$, —CO$_2$CH$_2$CH$_3$, —COCH$_3$, —COCH$_2$CH$_3$, —COH, —OC(O)CH$_3$, —C(O)NHCH$_3$, or —NC(O)CH$_3$. In yet a further embodiment, each $J^X$ is independently selected from $C_{1-4}$ straight or branched alkyl, $C_{2-4}$ straight or branched alkenyl, $C_{2-4}$ straight or branched alkynyl, cyclopropyl, cyclobutyl, cyclopentyl, cyclohexyl, chloro, fluoro, —OH, —OCH$_3$, —CH$_2$OCH$_3$, —CH$_2$OH, oxo, —CH$_2$CN, —CH$_2$CF$_3$, —CN, or —CF$_3$, CO$_2$H, —CO$_2$CH$_3$, or —COCH$_3$. In another embodiment, $J^X$ is not phenyl.

In another embodiment, the invention provides a compound of formula II:

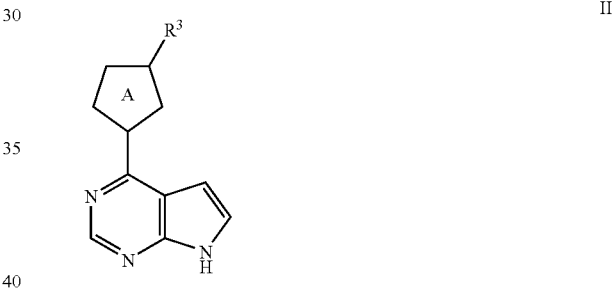

or a pharmaceutically acceptable salt thereof, wherein Ring A and $R^3$ are as defined above.

In one embodiment of formula II, Ring A is selected from the following:

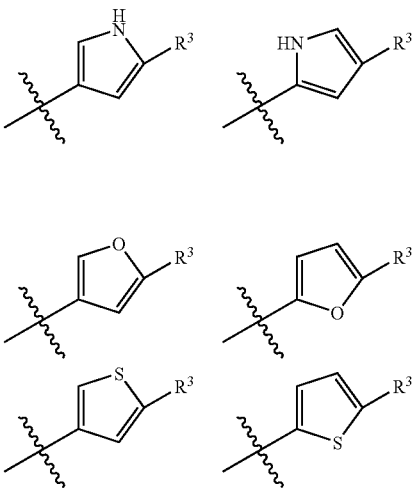

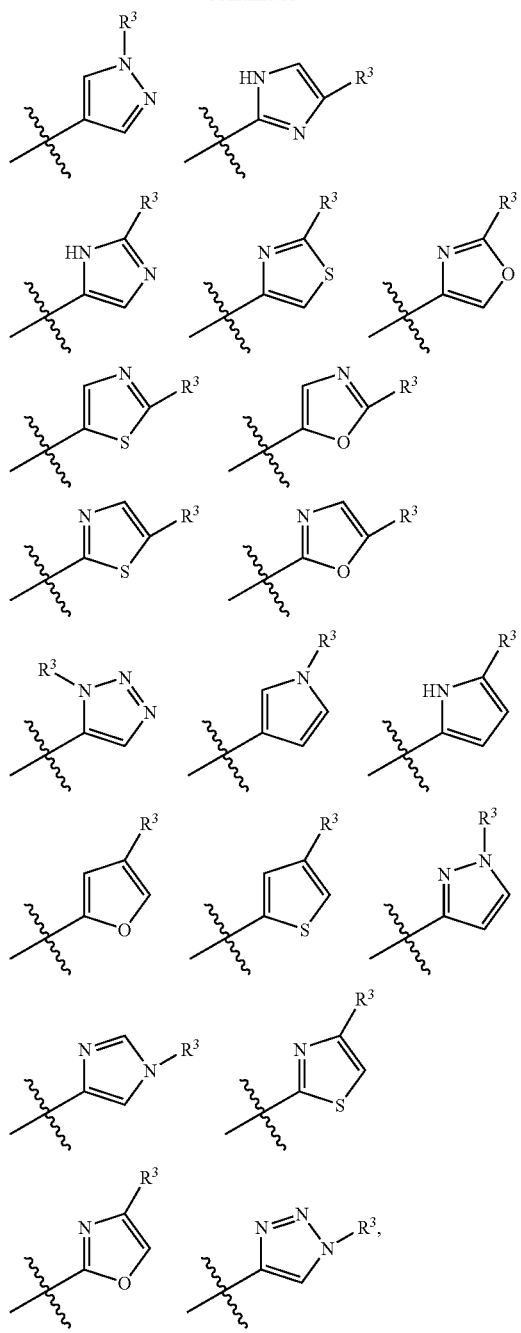

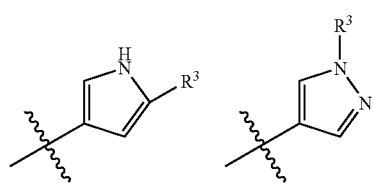

wherein Ring A is optionally substituted with 1-3 occurrences of $R^8$.

In a further embodiment of formula II, Ring A is selected from the following:

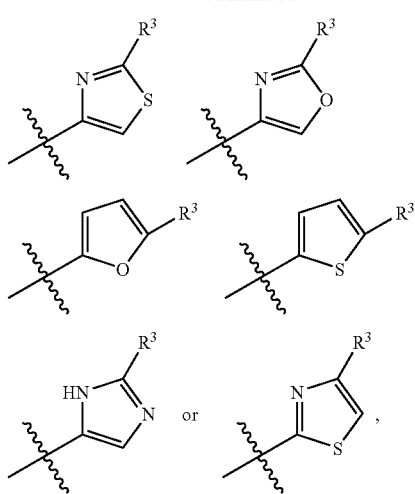

wherein Ring A is optionally substituted with 1-3 occurrences of $R^8$.

In yet another embodiment of formula II, Ring A is selected from the following:

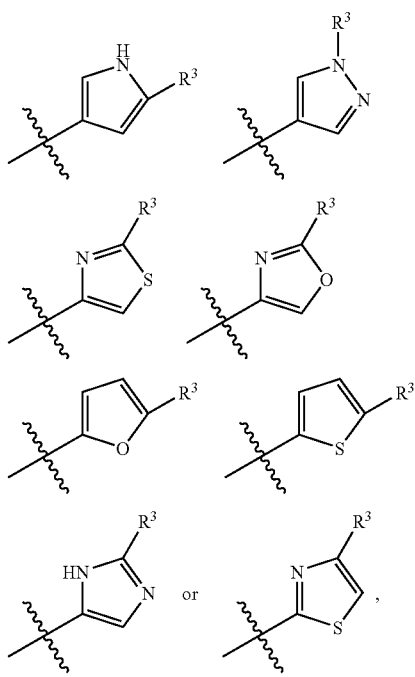

In yet a further embodiment of formula II, Ring A is selected from the following:

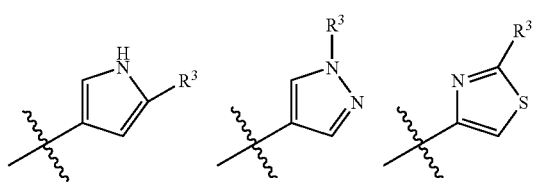

-continued

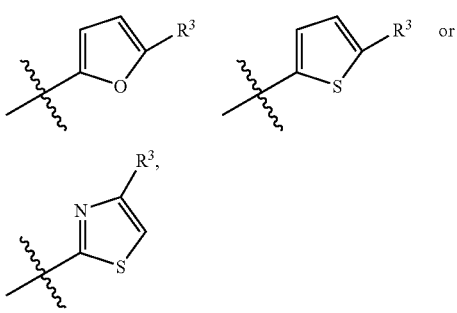

wherein Ring A is optionally substituted with 1-3 occurrences of $R^8$.

In yet a further embodiment of formula II, Ring A is selected from the following:

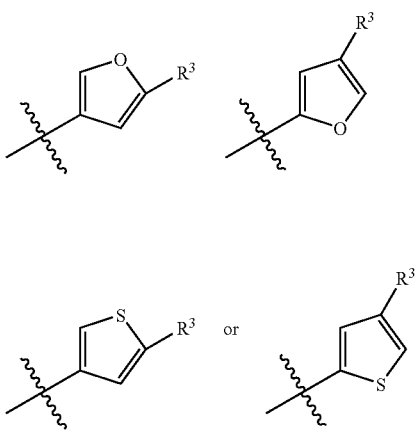

wherein Ring A is optionally substituted with 1-3 occurrences of $R^8$.

In another embodiment of formula II, Ring A is selected from the following:

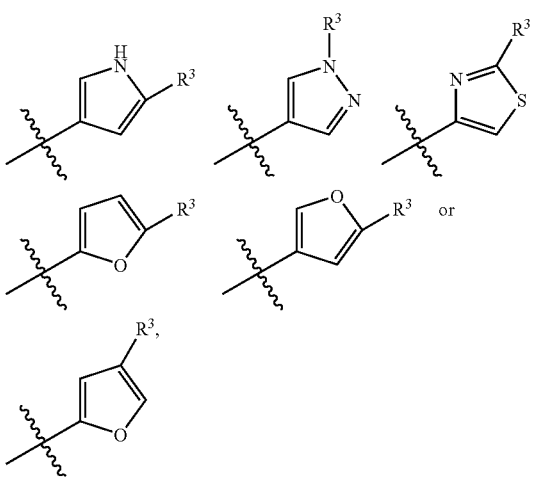

wherein Ring A is optionally substituted with 1-3 occurrences of $R^8$.

In another embodiment of formula II, Ring A is selected from the following:

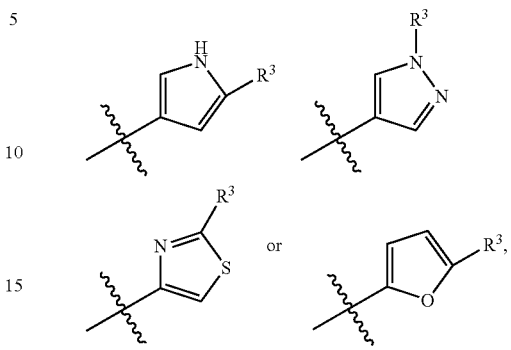

wherein Ring A is optionally substituted with 1-3 occurrences of $R^8$.

In one embodiment of formula II, Ring A is unsubstituted by $R^8$.

In another embodiment of formula II, $R^3$ is not H.

In another embodiment of formula II, m is 1 and U is selected from C(O)NH, C(O)$NR^6$, NHC(O), $NR^6$C(O), C(O), C(O)O, C(O)NH(CH$_2$)$_{1-3}$, C(O)$NR^6$(CH$_2$)$_{1-3}$, NHC(O)(CH$_2$)$_{1-3}$, $NR^6$C(O)(CH$_2$)$_{1-3}$, C(O)(CH$_2$)$_{1-3}$, C(O)O(CH$_2$)$_{1-3}$, (CH$_2$)$_{1-3}$C(O)NH, (CH$_2$)$_{1-3}$C(O)$NR^6$, (CH$_2$)$_{1-3}$NHC(O), (CH$_2$)$_{1-3}$$NR^6$C(O), (CH$_2$)$_{1-3}$C(O) or (CH$_2$)$_{1-3}$C(O)O. In a further embodiment, m is 1 and U is selected from C(O)NH, C(O)$NR^6$, NHC(O), $NR^6$C(O), C(O), C(O)O, C(O)NHCH$_2$, C(O)$NR^6$CH$_2$, NHC(O)CH$_2$, $NR^6$C(O)CH$_2$, C(O)CH$_2$, C(O)OCH$_2$, CH$_2$C(O)NH, CH$_2$C(O)$NR^6$, CH$_2$NHC(O), CH$_2$$NR^6$C(O), CH$_2$C(O) or CH$_2$C(O)O. In yet a further embodiment, m is 1 and U is selected from C(O)NH, C(O)$NR^6$, NHC(O), $NR^6$C(O), C(O), C(O)O, C(O)NHCH$_2$, C(O)$NR^6$CH$_2$, NHC(O)CH$_2$, $NR^6$C(O)CH$_2$, C(O)CH$_2$, C(O)OCH$_2$, CH$_2$C(O)NH, CH$_2$C(O)$NR^6$, CH$_2$NHC(O), CH$_2$$NR^6$C(O), CH$_2$C(O) or CH$_2$C(O)O. In yet a further embodiment, m is 1 and U is selected from C(O)NH, C(O)$NR^6$, NHC(O), $NR^6$C(O), C(O), C(O)NHCH$_2$, C(O)$NR^6$CH$_2$, NHC(O)CH$_2$ or $NR^6$C(O)CH$_2$.

In another embodiment of formula II, $R^6$ is $C_{1-4}$ aliphatic optionally substituted with —OH, —OCH$_3$, —SH, —SCH$_3$, —CF$_3$, —CN, —CO$_2$H, —CO$_2$CH$_3$, NHCOH, NHCOCH$_3$, CONH$_2$ or CONHCH$_3$. In a further embodiment, $R^6$ is $C_{1-3}$ aliphatic optionally substituted with —OH, —CF$_3$ or —CN.

In another embodiment of formula II, m is 0 and U is absent.

In another embodiment of formula II, X is a group selected from a $C_{1-6}$ aliphatic, a $C_{3-7}$ cycloaliphatic, a $C_{6-10}$ aryl, a 5-8 membered heteroaryl, or a 5-8 membered heterocyclyl, wherein said group is optionally substituted with 1-4 $J^X$. In a further embodiment, X is a group selected from a $C_{1-6}$ aliphatic, a $C_{3-6}$ cycloaliphatic, phenyl, a 5-6 membered heteroaryl, or a 5-7 membered heterocyclyl, wherein said group is optionally substituted with 1-4 $J^X$. In yet a further embodiment, X is $C_{1-4}$ straight or branched alkyl, $C_{2-4}$ straight or branched alkenyl, $C_{2-4}$ straight or branched alkynyl, cyclopropyl, cyclobutyl, cyclopentyl, cyclohexyl, phenyl, pyridyl, pyrimidinyl, pyrrolyl, piperidinyl, pyrrolidinyl, dihydro-1H-pyrrolyl, tetrahydro-1H-pyranyl, tetrahydrofuranyl, wherein said group is optionally substituted with 1-4 $J^X$. In another embodiment, X is not an optionally substituted $C_{6-10}$ aryl. In a further embodiment, X is not an optionally substituted phenyl.

In one embodiment of formula II, each $J^X$ is independently selected from halogen, R', $-(L_n)-N(R')_2$, $-(L_n)-SR'$, $-(L_n)-OR'$, $-(L_n)-(C_{3-6}$ cycloaliphatic), oxo, $C_{1-4}$haloalkyl, $-(L_n)-CN$, $-(L_n)-OH$, $-(L_n)-CF_3$, $-CO_2R'$, $-CO_2H$, $-COR'$, $-COH$, $-OC(O)R'$, $-C(O)NHR'$, or $-NC(O)R'$; or two $J^X$ groups, on the same substituent or different substituents, together with the atom(s) to which each $J^X$ group is bound, form a 5-7 membered saturated, unsaturated, or partially saturated ring. In a further embodiment, each $J^X$ is independently selected from $C_{1-4}$ aliphatic, $C_{3-7}$ cycloaliphatic, halogen, $(CH_2)_{0-3}$ OH, $(CH_2)_{0-3}OCH_3$, $(CH_2)_{0-3}OCH_2CH_3$, oxo, $(CH_2)_{0-3}$ $NH_2$, $(CH_2)_{0-3}NHCH_3$, $(CH_2)_{0-3}N(CH_3)_2$, $(CH_2)_{0-3}SH$, $(CH_2)_{0-3}$ $SCH_3$, $(CH_2)_{0-3}SCH_2CH_3$, $(CH_2)_{0-3}CN$, $(CH_2)_{0-3}$ $CF_3$, $CO_2H$, $-CO_2CH_3$, $-CO_2CH_2CH_3$, $-COCH_3$, $-COCH_2CH_3$, $-COH$, $-OC(O)CH_3$, $-C(O)NHCH_3$, or $-NC(O)CH_3$. In yet a further embodiment, each $J^X$ is independently selected from $C_{1-4}$ straight or branched alkyl, $C_{2-4}$ straight or branched alkenyl, $C_{2-4}$ straight or branched alkynyl, cyclopropyl, cyclobutyl, cyclopentyl, cyclohexyl, chloro, fluoro, $-OH$, $-OCH_3$, $-CH_2OCH_3$, $-CH_2OH$, oxo, $-CH_2CN$, $-CH_2CF_3$, $-CN$, or $-CF_3$, $CO_2H$, $-CO_2CH_3$, or $-COCH_3$. In another embodiment, $J^X$ is not phenyl.

In another embodiment, the invention provides a compound of formulae I or II, wherein said compound inhibits a JAK kinase with a lower $K_i$ (i.e., is more potent) than said compound inhibits one or more kinases selected from Aurora-2 (AUR-A), Src, CDK2 or Flt-3. In another embodiment, the invention provides a compound of formulae I or II, wherein said compound inhibits JAK2 with a lower $K_i$ than said compound inhibits one or more kinases selected from JAK3, Aurora-2, Src, CDK2 or Flt-3. In another embodiment, the invention provides a compound of formulae I or II, wherein said compound inhibits a JAK kinase with a lower $K_i$ than said compound inhibits ERK2.

In another embodiment, the invention provides a compound of Table 1:

TABLE 1

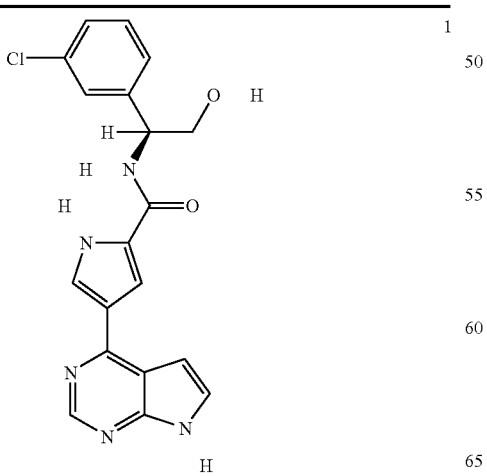

1

TABLE 1-continued

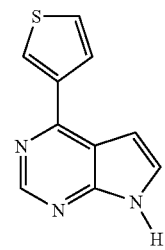 [SMILES: c1nc(-c2ccsc2)c2cc[nH]c2n1]

2

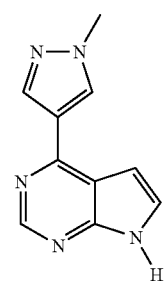

3

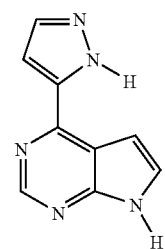 [SMILES: c1cc(-c2ncnc3[nH]ccc23)[nH]n1]

4

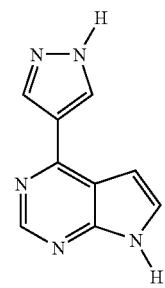 [SMILES: c1nc(-c2cn[nH]c2)c2cc[nH]c2n1]

5

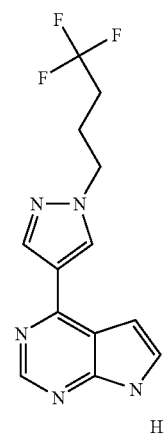

6

TABLE 1-continued
| | |
|---|---|
| 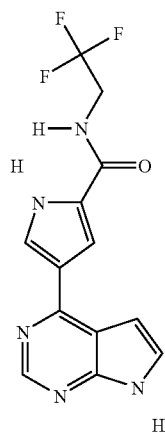 7 | 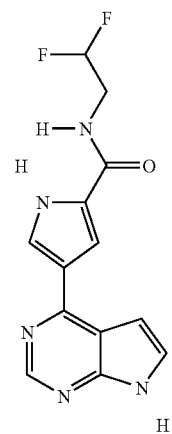 10 |
| 8 | 11 |
| 9 | 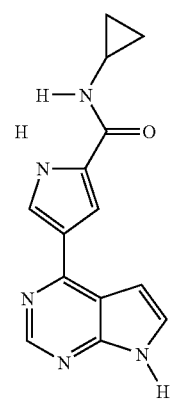 12 |

TABLE 1-continued
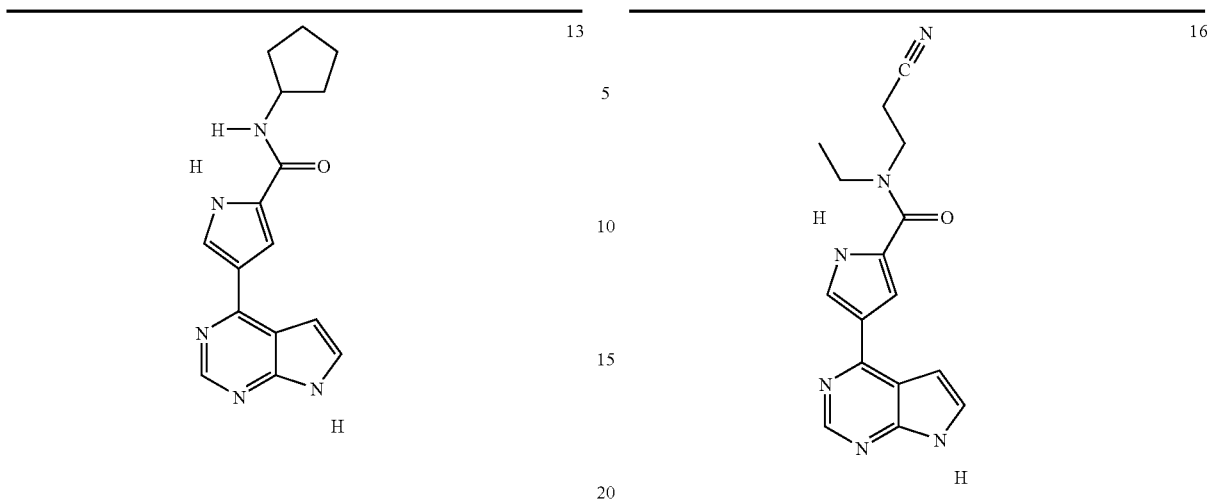
TABLE 1-continued
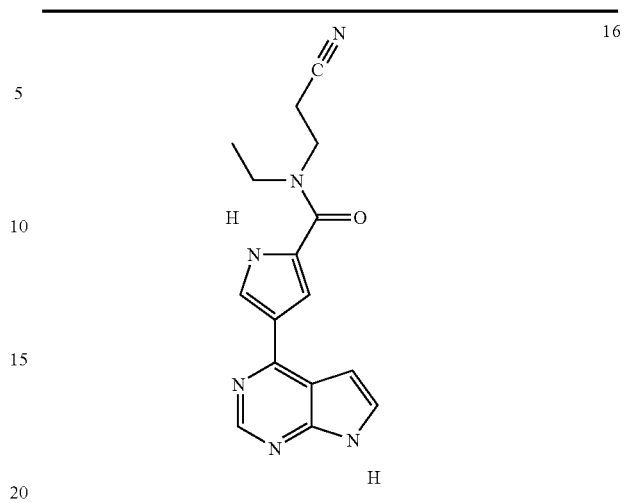

TABLE 1-continued
| 19 | 22 |
|---|---|
| 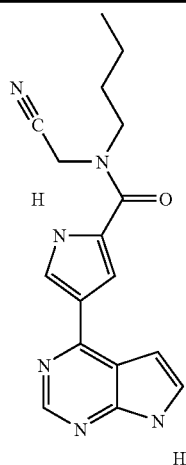 | 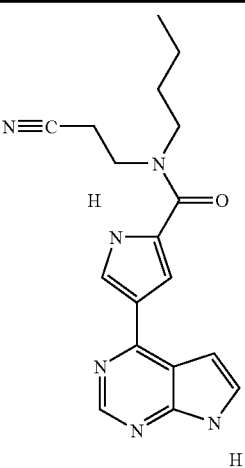 |
| 20 | 23 |
| 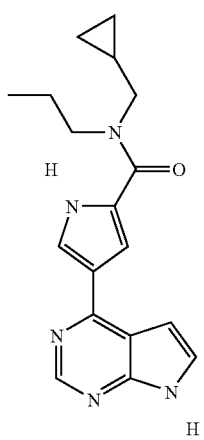 | 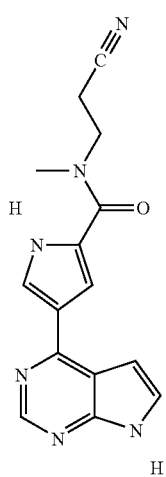 |
| 21 | 24 |
| 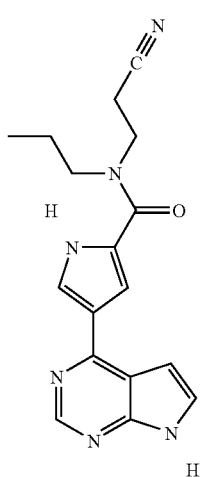 | 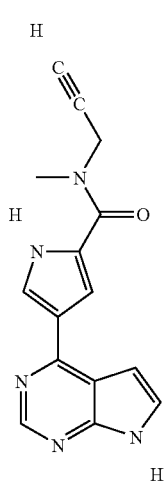 |

TABLE 1-continued
| 25 |
|---|
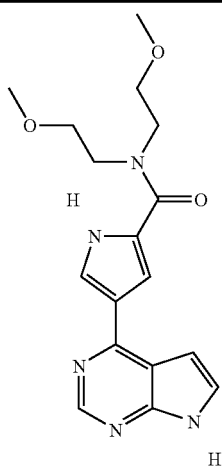
| 26 |
|---|
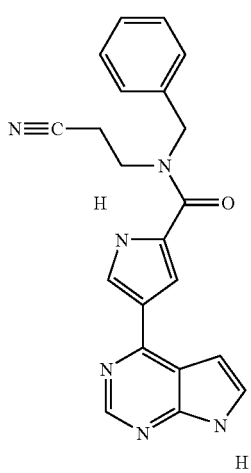
| 27 |
|---|
TABLE 1-continued
| 28 |
|---|
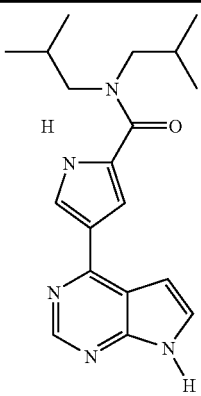
| 29 |
|---|
| 30 |
|---|
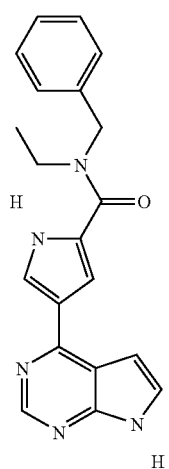

TABLE 1-continued
| | |
|---|---|
| 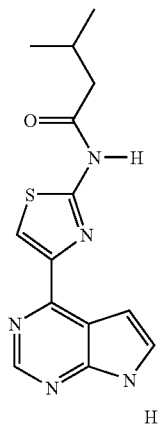 | 31 |
| 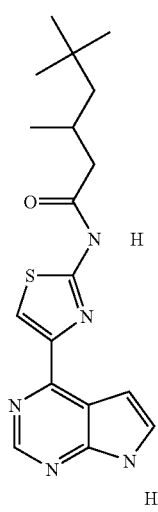 | 32 |
| | 33 |
TABLE 1-continued
| | |
|---|---|
| 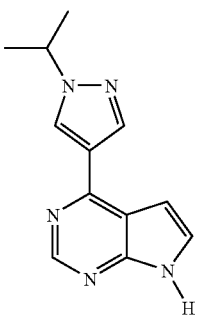 [SMILES: CC(C)n1cc(-c2ncnc3[nH]ccc23)cn1] | 34 |
| 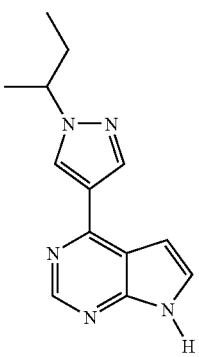 [SMILES: CCC(C)n1cc(-c2ncnc3[nH]ccc23)cn1] | 35 |
| 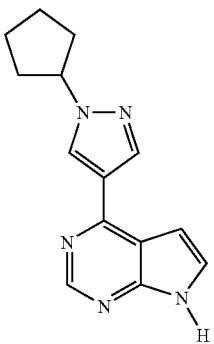 [SMILES: c1nc(-c2cnn(C3CCCC3)c2)c2cc[nH]c2n1] | 36 |
| 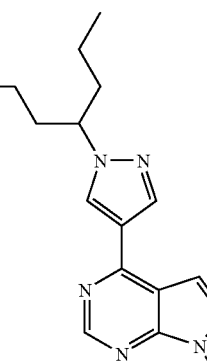 | 37 |

TABLE 1-continued
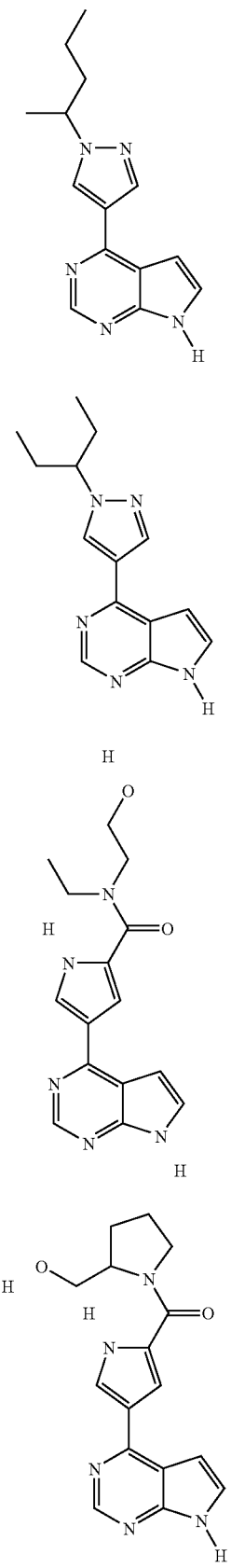
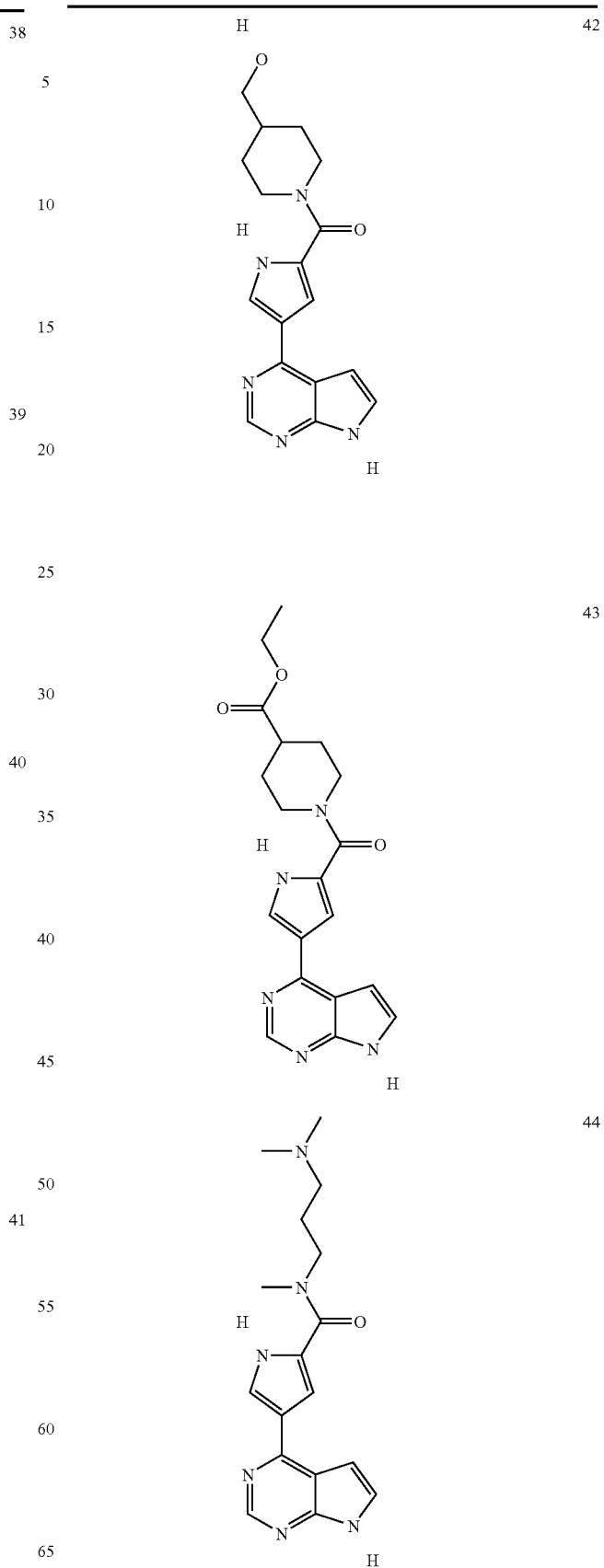

TABLE 1-continued
| | |
|---|---|
| 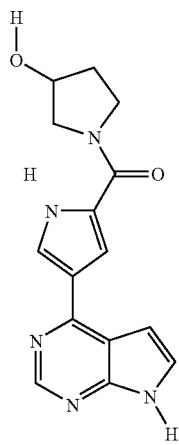 45 | 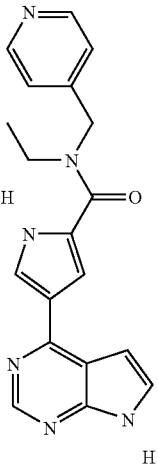 48 |
| 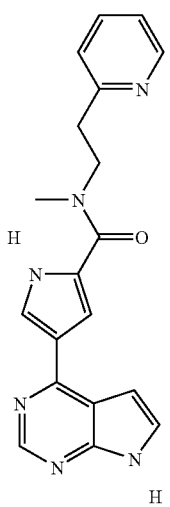 46 | 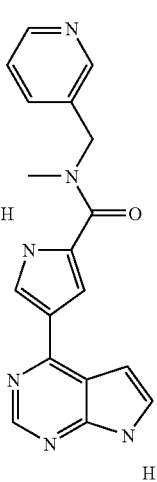 49 |
| 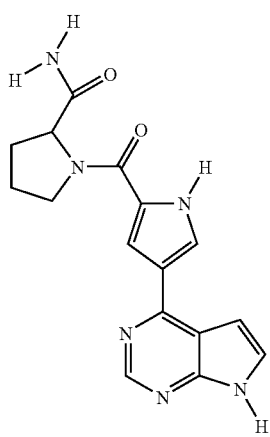 [SMILES: NC(=O)C1CCCN1C(=O)c1cc(-c2ncnc3[nH]ccc23)c[nH]1] 47 | 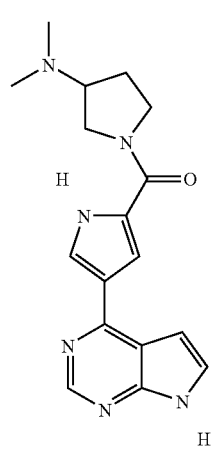 50 |

TABLE 1-continued
| | |
|---|---|
| 51 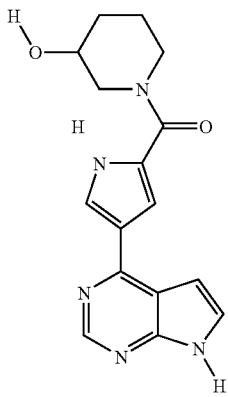 | 55 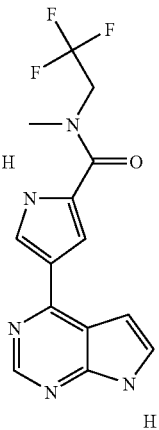 |
| 52 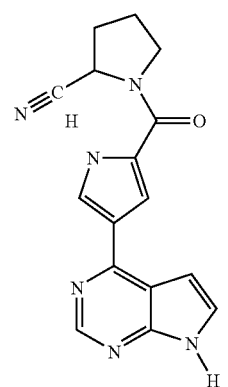 | 56 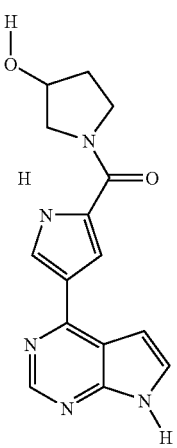 |
| 53 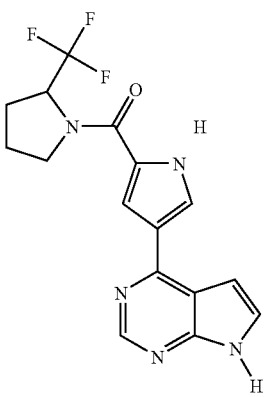 | 57 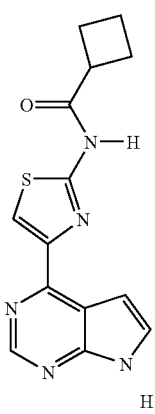 |
| 54 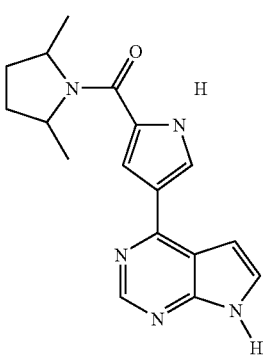 | |

TABLE 1-continued
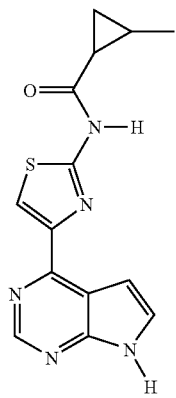 58
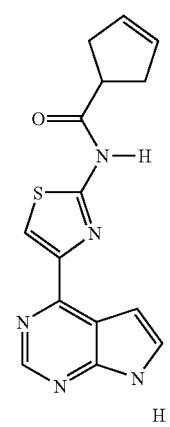 59
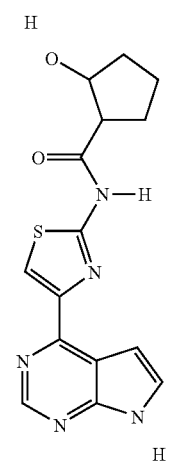 60
TABLE 1-continued
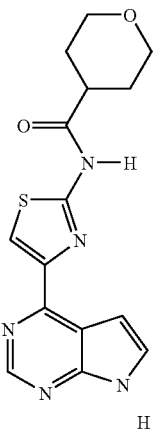 61
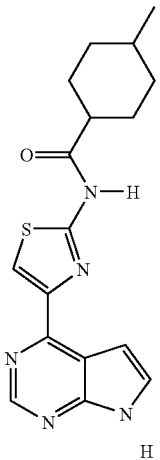 62
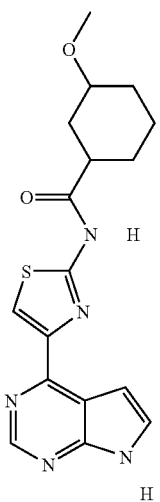 63

TABLE 1-continued
64
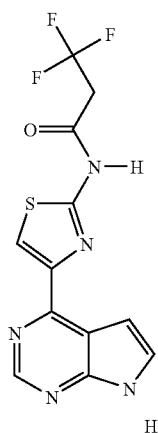
67
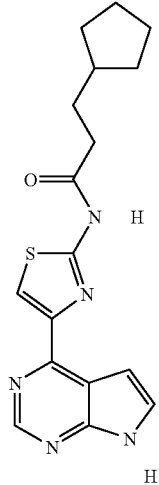
65
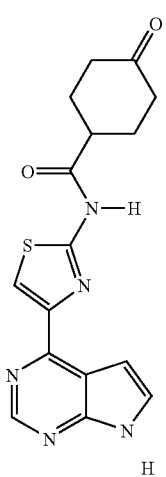
68
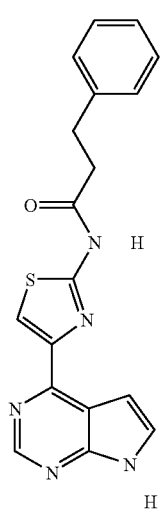
66
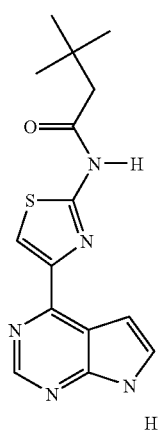
69
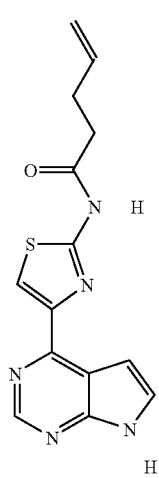

TABLE 1-continued
70
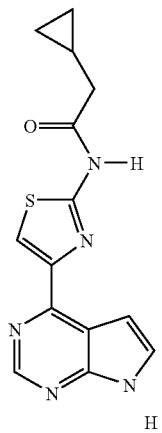
71
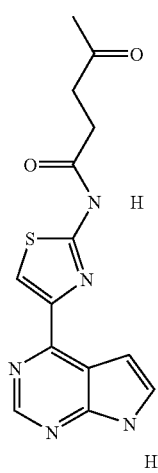
72
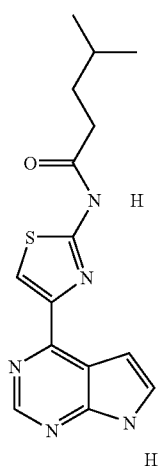
TABLE 1-continued
73
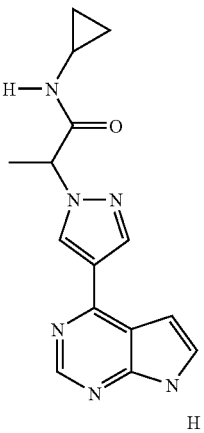
74
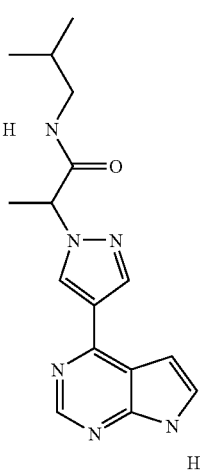
75
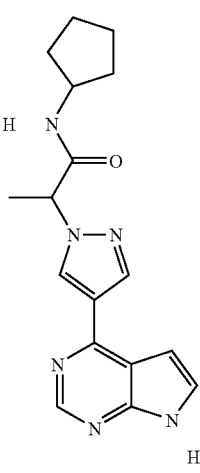

TABLE 1-continued
| | |
|---|---|
| 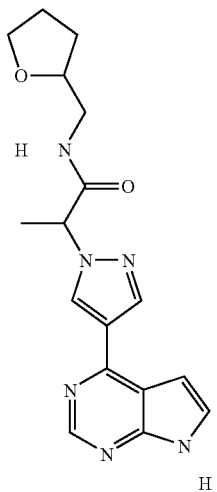 76 | 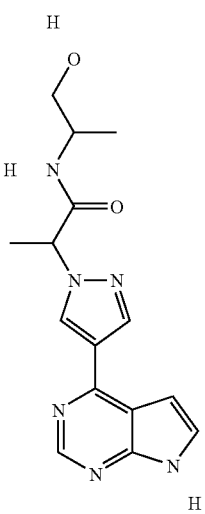 79 |
| 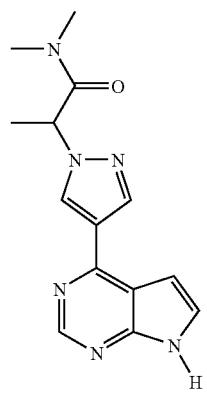 [SMILES: CC(C(=O)N(C)C)n1cc(-c2ncnc3[nH]ccc23)cn1] 77 | 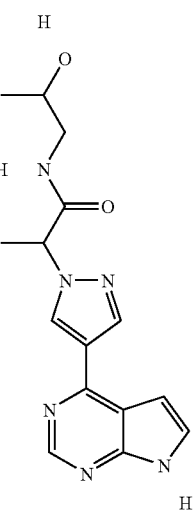 80 |
| 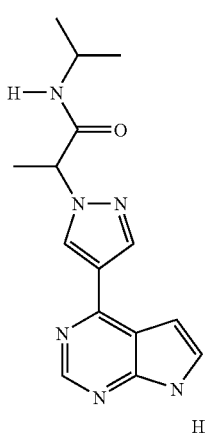 78 | 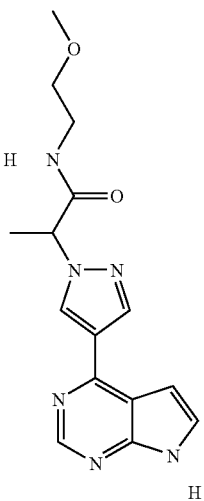 81 |

TABLE 1-continued
| | |
|---|---|
| 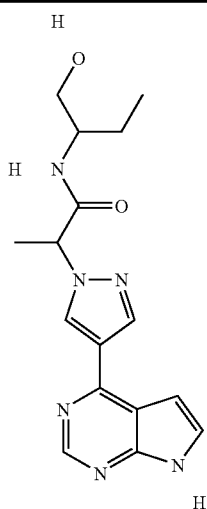 | 82 |
| 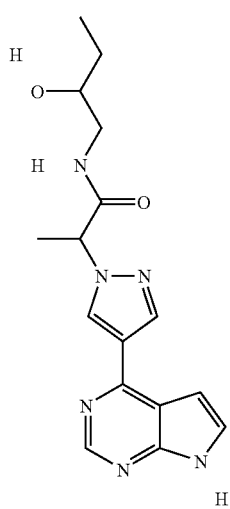 | 83 |
| 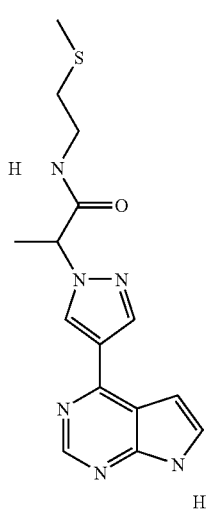 | 84 |
TABLE 1-continued
| | |
|---|---|
| 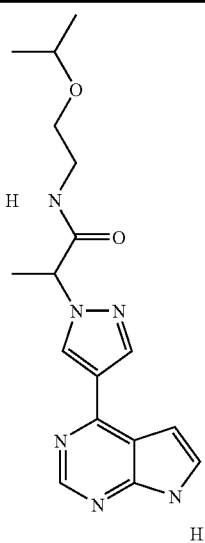 | 85 |
| 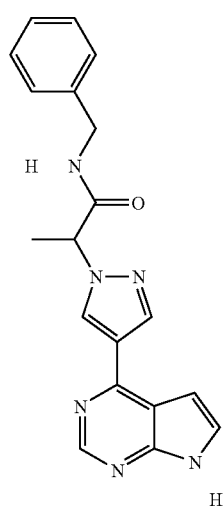 | 86 |
| 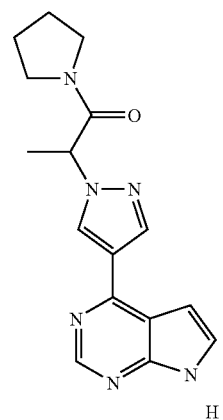 | 87 |

TABLE 1-continued
88 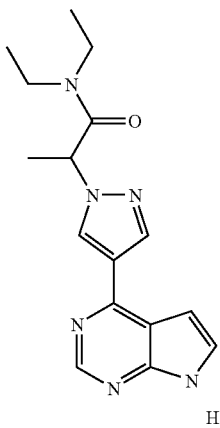
89 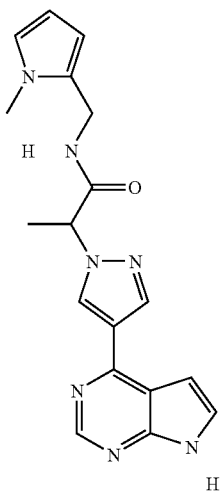
90 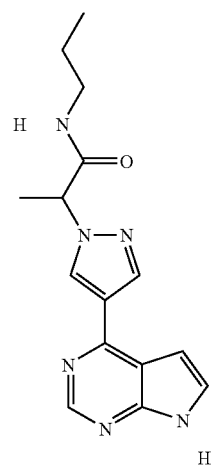
TABLE 1-continued
91 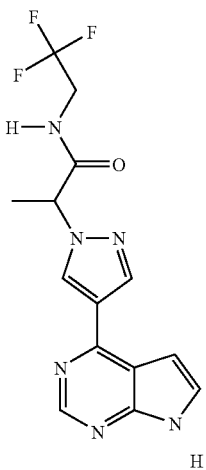
92 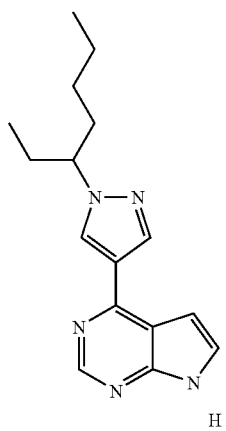
93 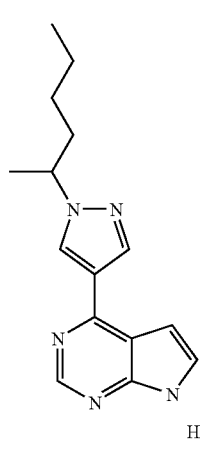

TABLE 1-continued
| | |
|---|---|
| 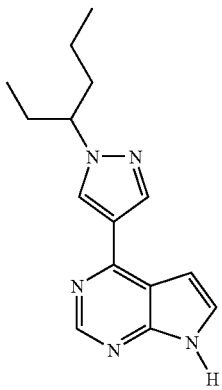 [SMILES: CCCC(CC)n1cc(-c2ncnc3[nH]ccc23)cn1] 94 | 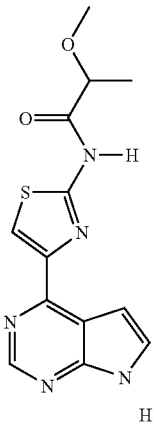 97 |
| 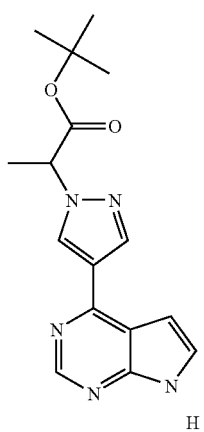 95 | 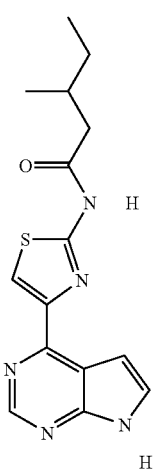 98 |
| 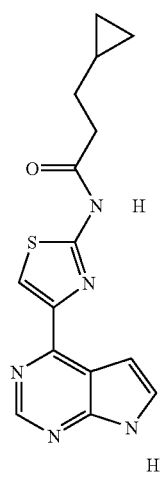 96 | 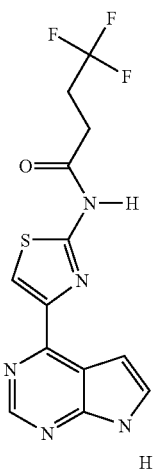 99 |

TABLE 1-continued
| | |
|---|---|
| 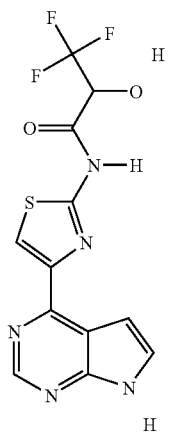 | 100 |
| 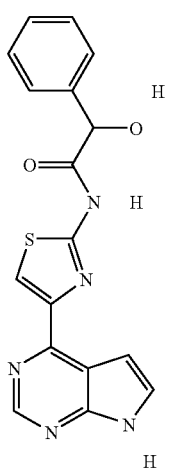 | 101 |
| 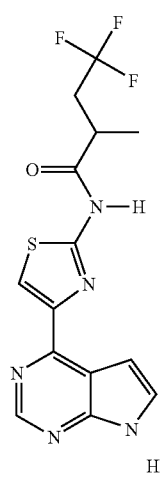 | 102 |
TABLE 1-continued
| | |
|---|---|
| 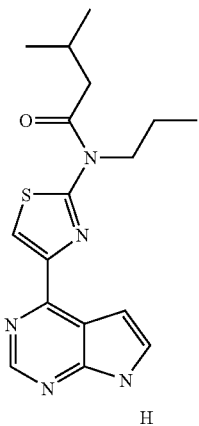 | 103 |
| 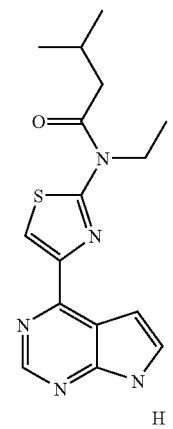 | 104 |
| 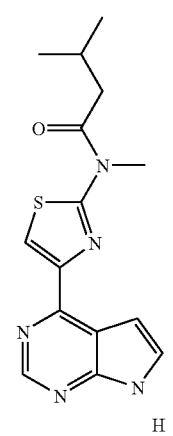 | 105 |
| 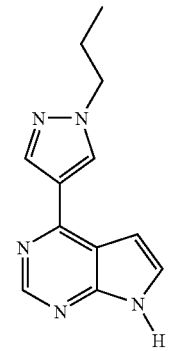 [SMILES: CCCn1cc(-c2ncnc3[nH]ccc23)cn1] | 106 |

TABLE 1-continued
107 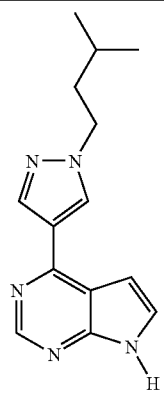
108 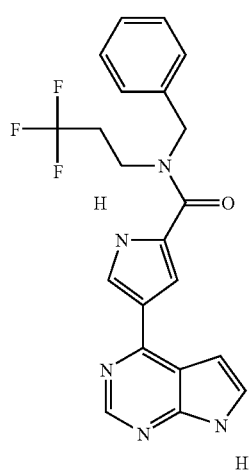
109 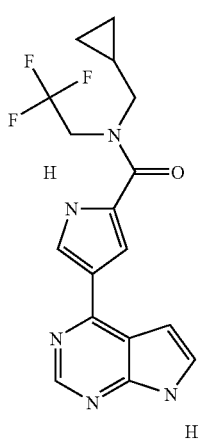
TABLE 1-continued
110 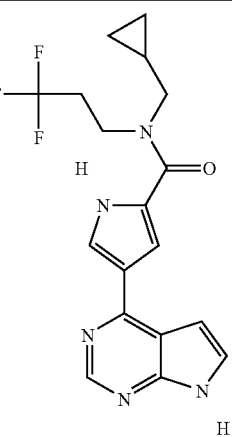
111 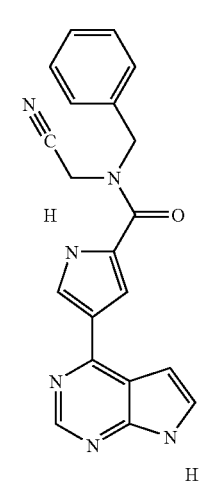
112 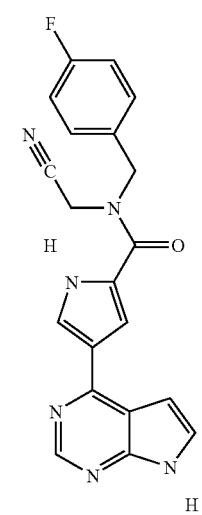

TABLE 1-continued
| | |
|---|---|
| 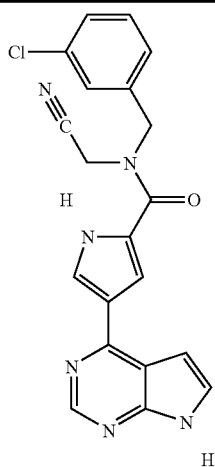 | 113 |
| 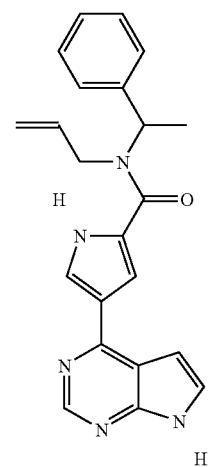 | 114 |
| 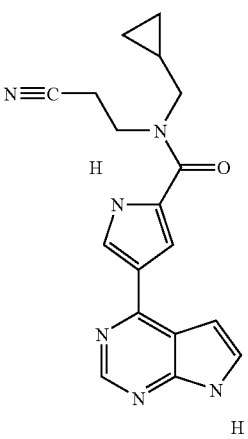 | 115 |
TABLE 1-continued
| | |
|---|---|
| 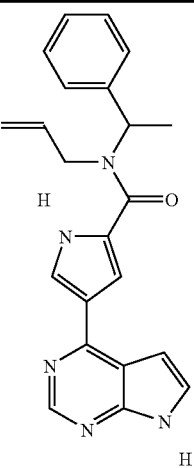 | 116 |
| 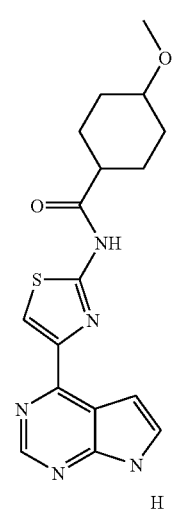 | 117 |
| 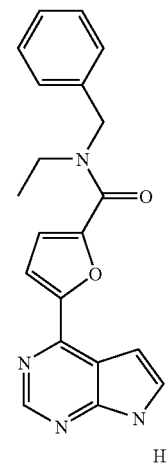 | 118 |

TABLE 1-continued
| 119 | 122 |
| 120 | 123 |
| 121 | 124 |
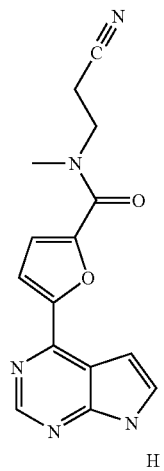
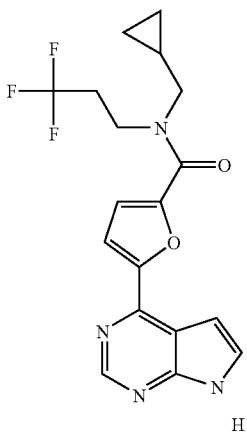
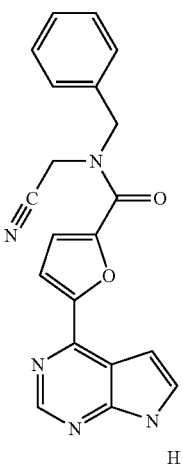

TABLE 1-continued
| 125 | 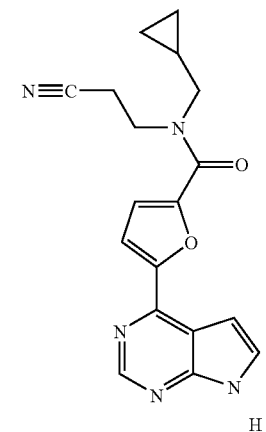 |
| 126 | 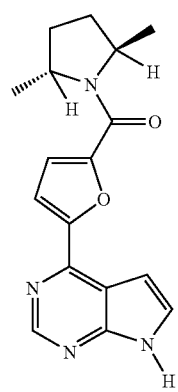 [SMILES: C[C@@H]1CC[C@@H](C)N1C(=O)c1ccc(-c2ncnc3[nH]ccc23)o1] |
| 127 | 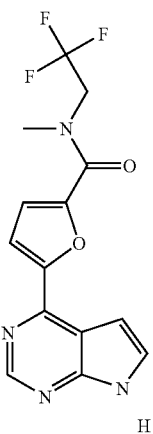 |
TABLE 1-continued
| 128 | 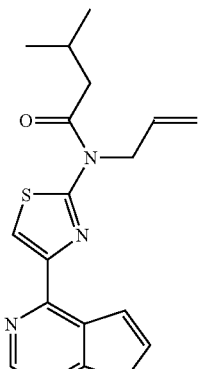 |
| 129 | 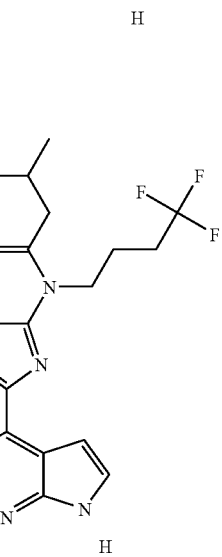 |
| 130 | 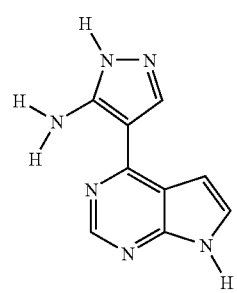 [SMILES: Nc1[nH]ncc1-c1ncnc2[nH]ccc12] |
| 131 | 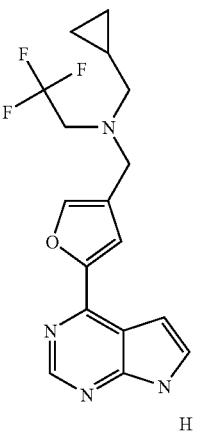 |

TABLE 1-continued
| | |
|---|---|
| 132 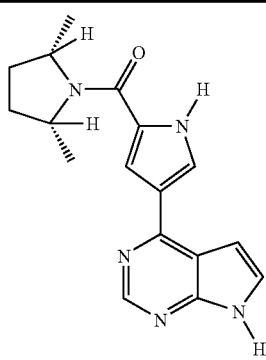 | 135 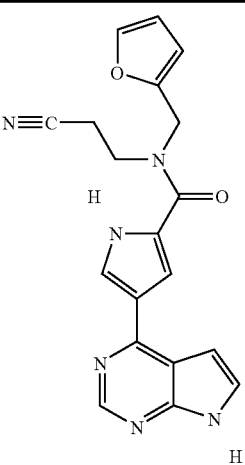 |
| 133 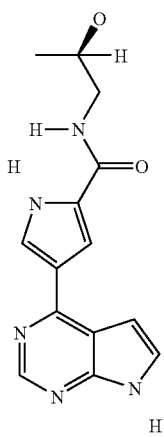 | 136 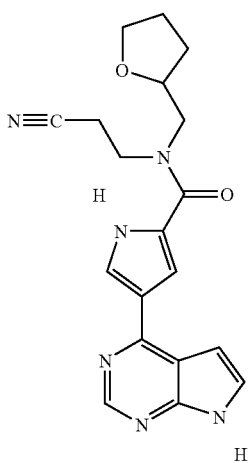 |
| 134 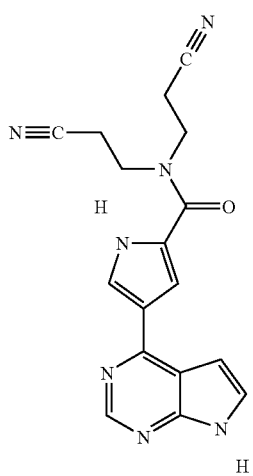 | 137 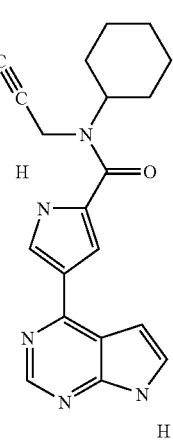 |

TABLE 1-continued
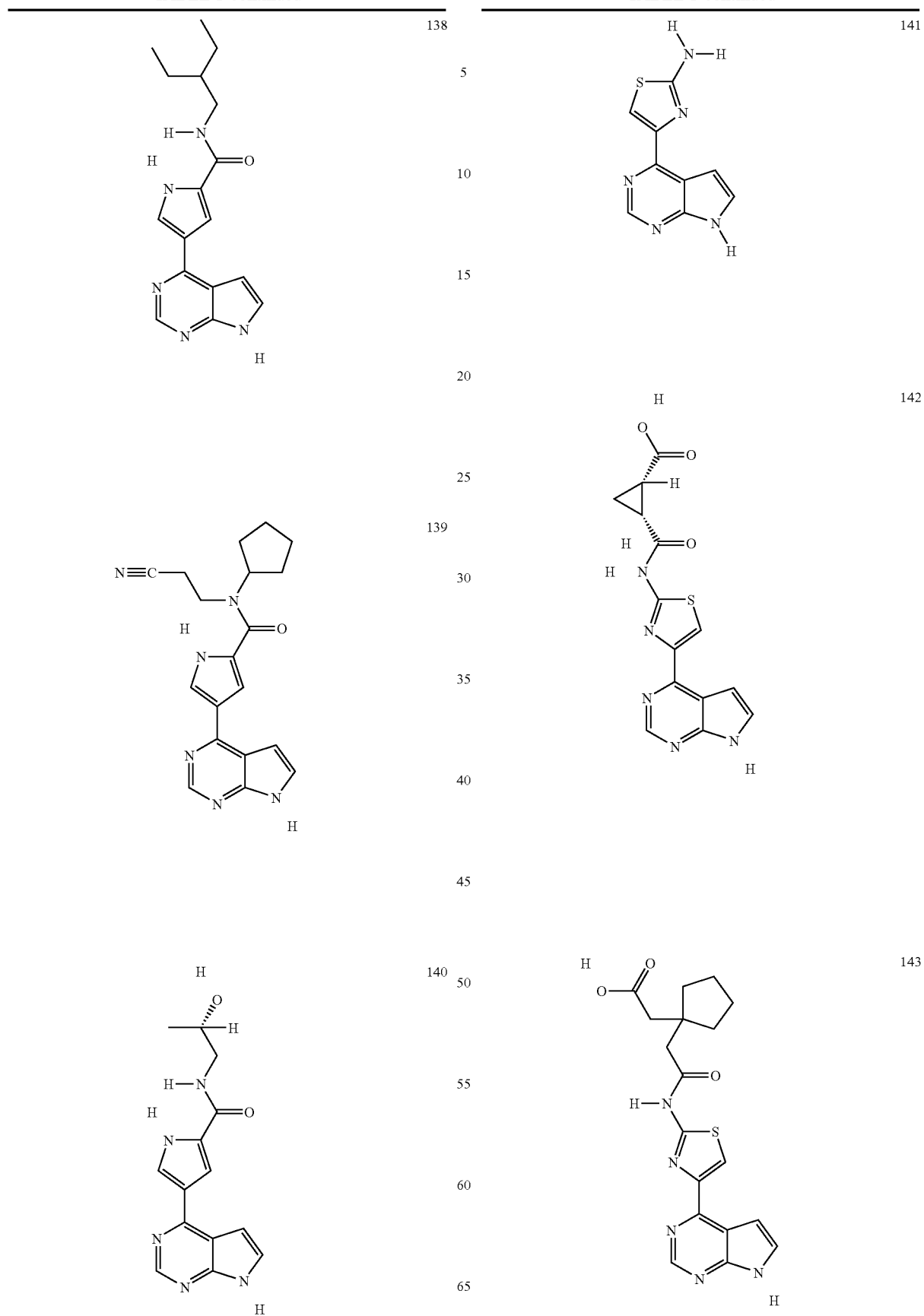

TABLE 1-continued
| 144 | 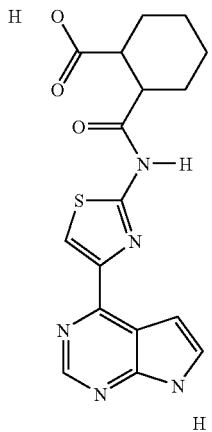 |
| 145 | 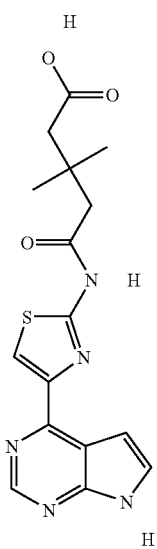 |
| 146 | 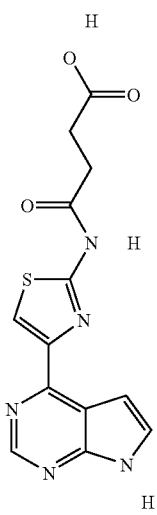 |
TABLE 1-continued
| 147 | 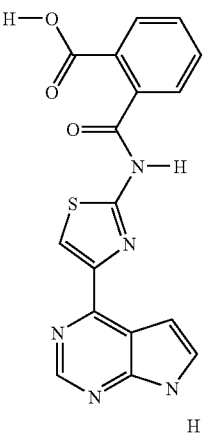 |
| 148 | 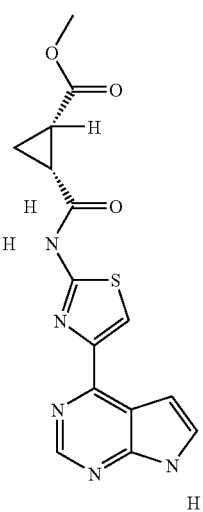 |
| 149 | 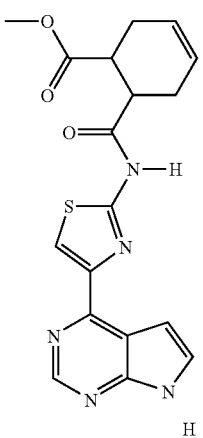 |

TABLE 1-continued
| | |
|---|---|
| 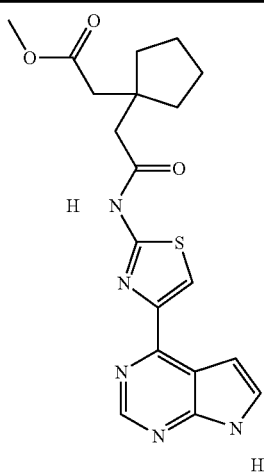 | 150 |
| 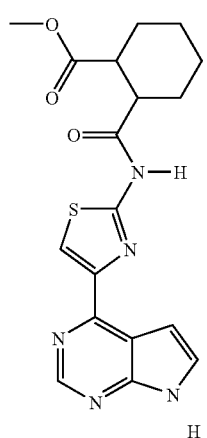 | 151 |
| 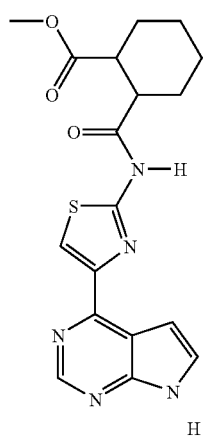 | 152 |
| 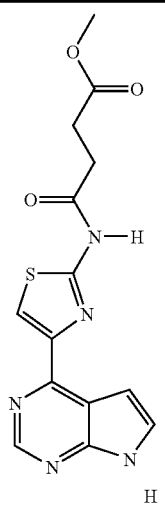 | 153 |
| 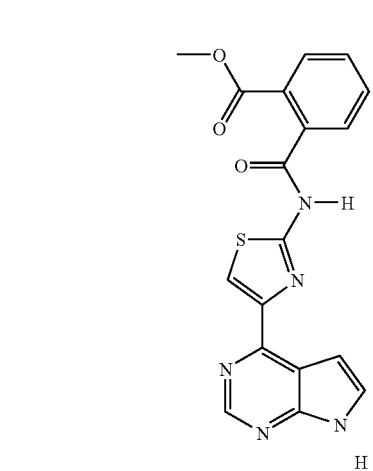 | 154 |
| 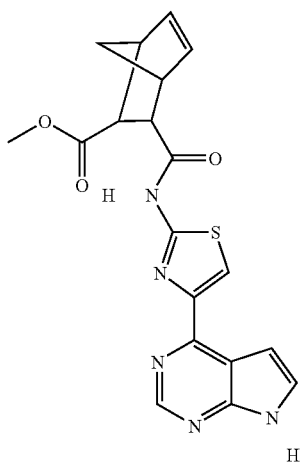 | 155 |

TABLE 1-continued
| | |
|---|---|
| 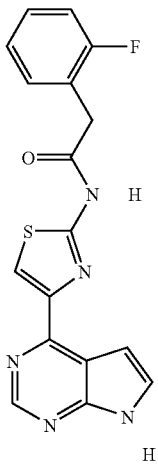 | 156 |
| 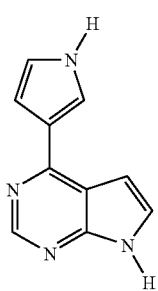 [SMILES: c1nc(-c2cc[nH]c2)c2cc[nH]c2n1] | 158 |
In another embodiment, the invention provides a compound of Table 2:
TABLE 2
| | |
|---|---|
| 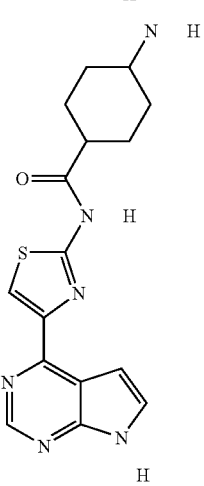 | 159 |
| 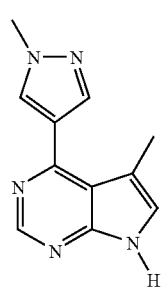 [SMILES: Cc1c[nH]c2ncnc(-c3cnn(C)c3)c12] | 160 |
| 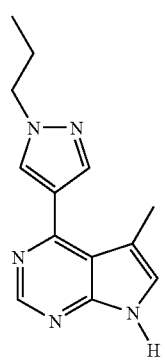 [SMILES: CCCn1cc(-c2ncnc3[nH]cc(C)c23)cn1] | 161 |
| 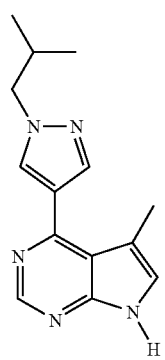 [SMILES: Cc1c[nH]c2ncnc(-c3cnn(CC(C)C)c3)c12] | 162 |

TABLE 2-continued
| | |
|---|---|
| 163 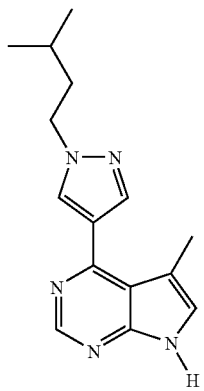 [SMILES: Cc1c[nH]c2ncnc(-c3cnn(CCC(C)C)c3)c12] | 167 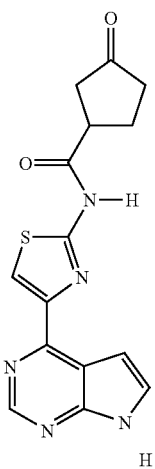 |
| 164 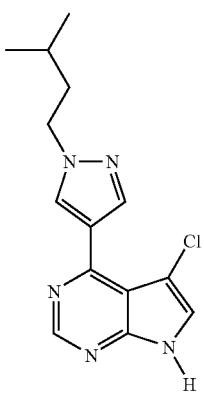 [SMILES: CC(C)CCn1cc(-c2ncnc3[nH]cc(Cl)c23)cn1] | 168 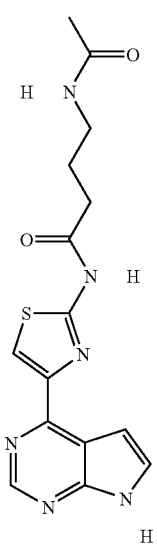 |
| 165 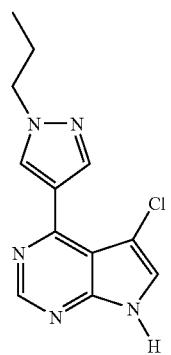 [SMILES: CCCn1cc(-c2ncnc3[nH]cc(Cl)c23)cn1] | 169 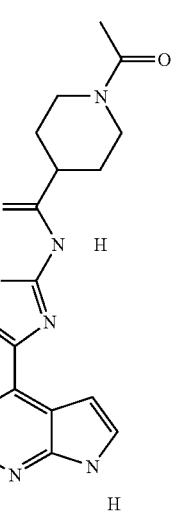 |
| 166 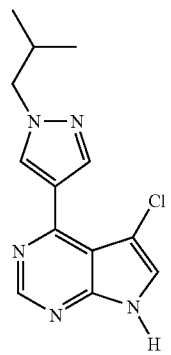 [SMILES: CC(C)Cn1cc(-c2ncnc3[nH]cc(Cl)c23)cn1] | |

TABLE 2-continued
170
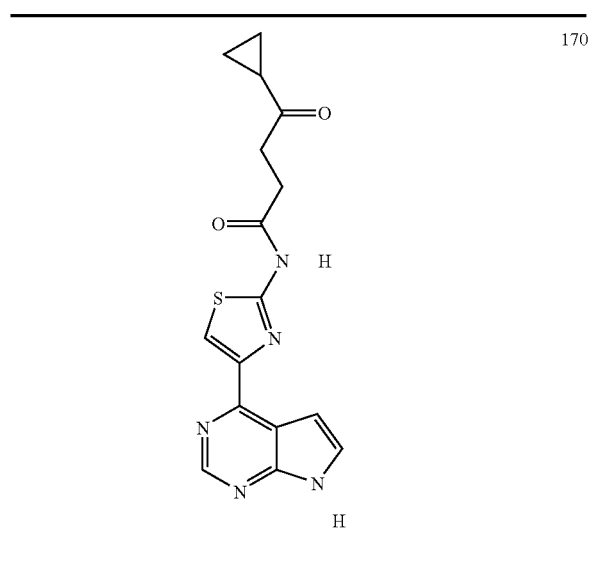
171
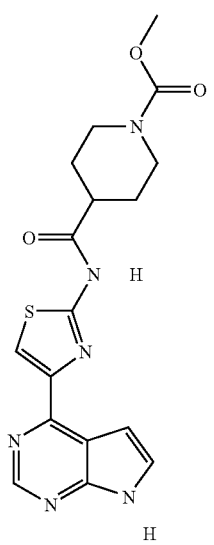
172
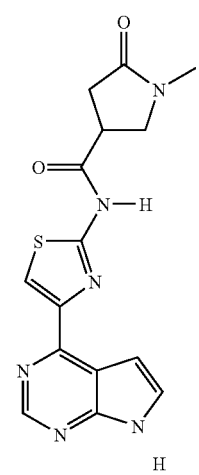
TABLE 2-continued
173
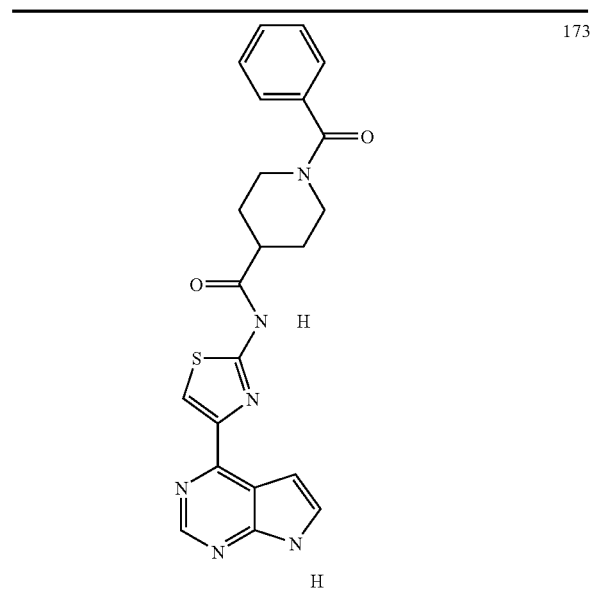
174
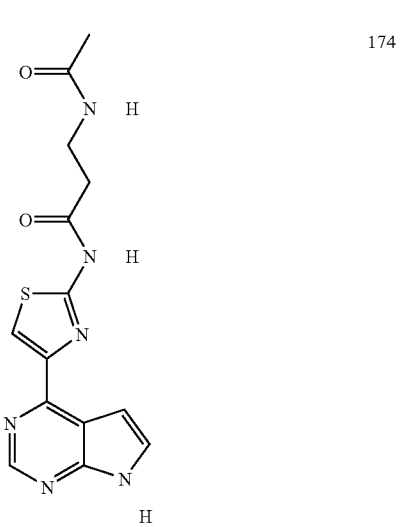
175
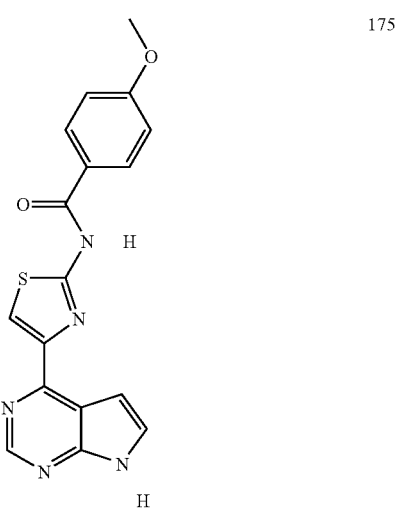

TABLE 2-continued
| | |
|---|---|
| 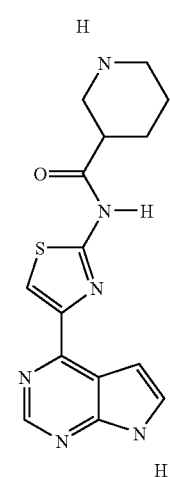 | 176 |
| 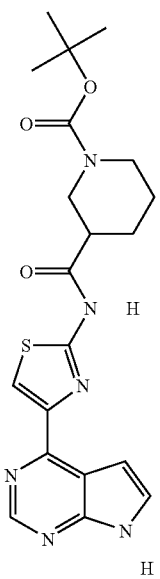 | 177 |
| 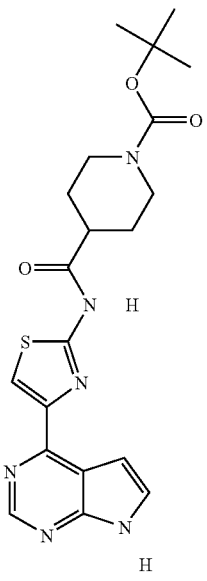 | 178 |
TABLE 2-continued
| | |
|---|---|
| 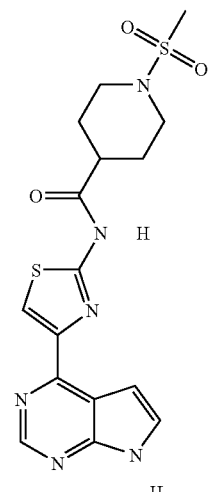 | 179 |
| 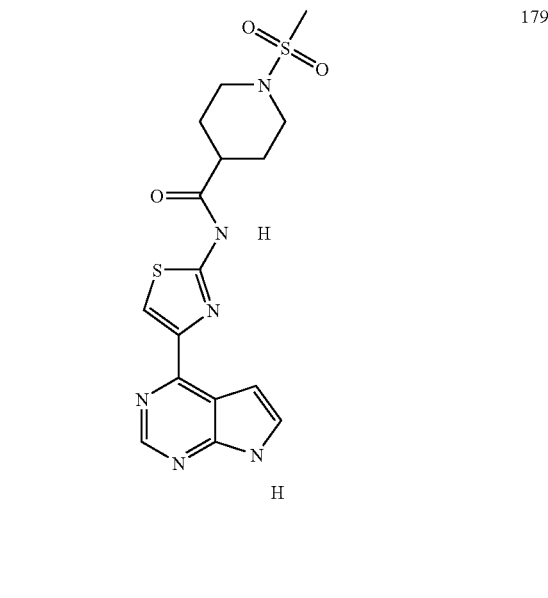 | 180 |
| | 181 |
| 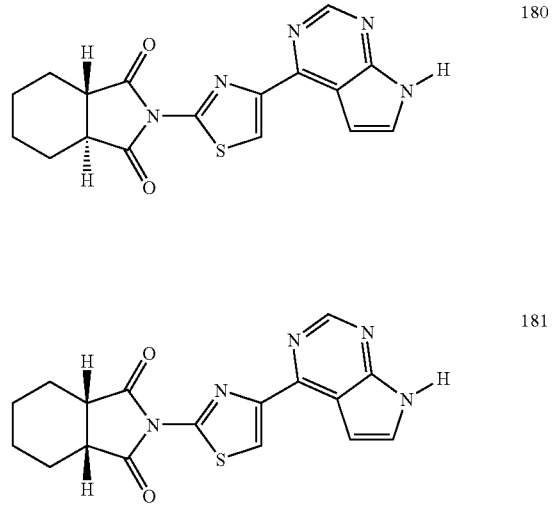 | 182 |

TABLE 2-continued
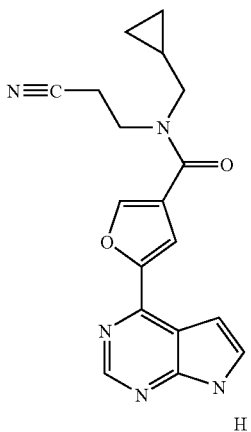
183
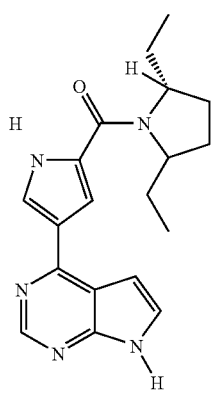
184
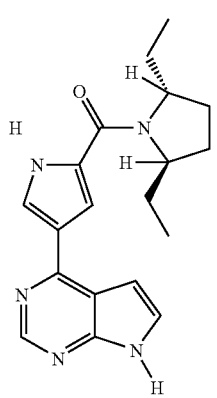
185
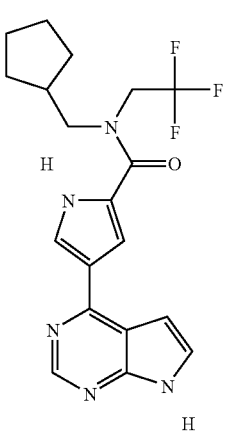
186
TABLE 2-continued
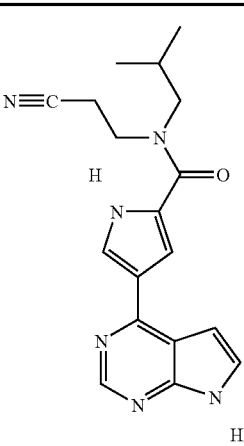
187
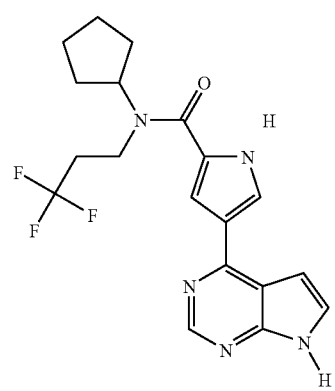
188
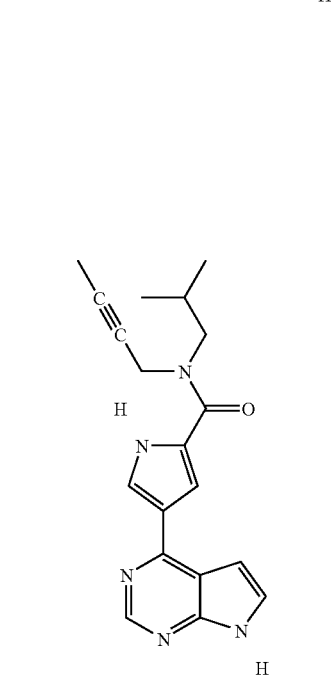
189

TABLE 2-continued
| | |
|---|---|
| 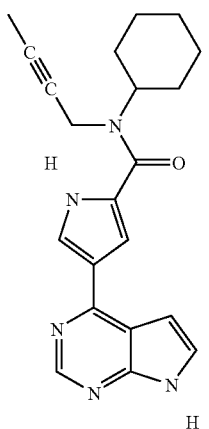 | 190 |
| 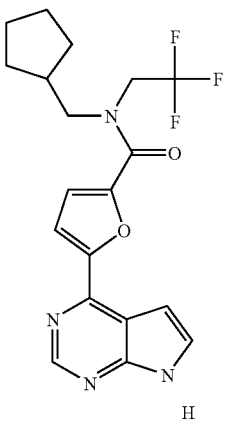 | 191 |
| 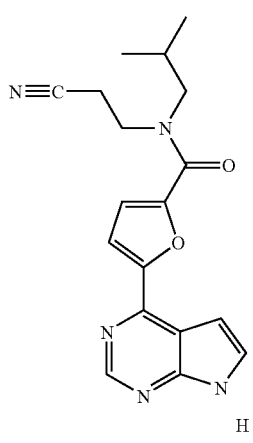 | 192 |
| 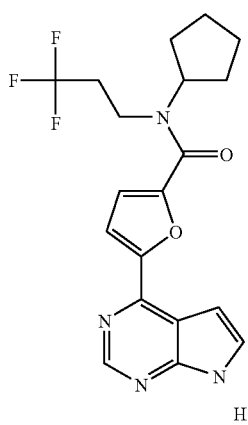 | 193 |
| 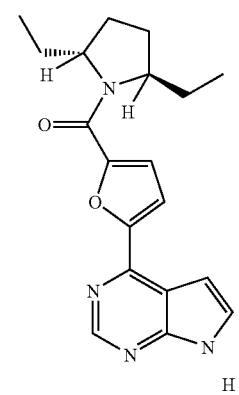 | 194 |
| 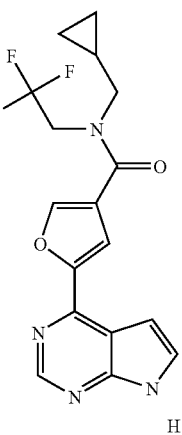 | 195 |

TABLE 2-continued
| | |
|---|---|
| 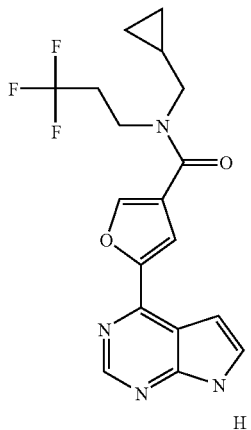 | 196 |
| 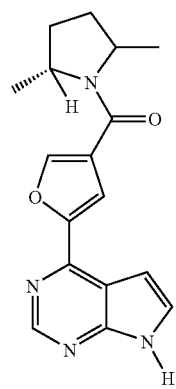 [SMILES: CC1CC[C@@H](C)N1C(=O)c1coc(-c2ncnc3[nH]ccc23)c1] | 197 |
| 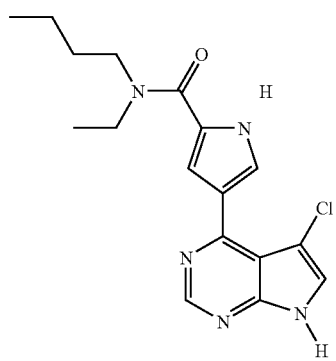 | 198 |
| 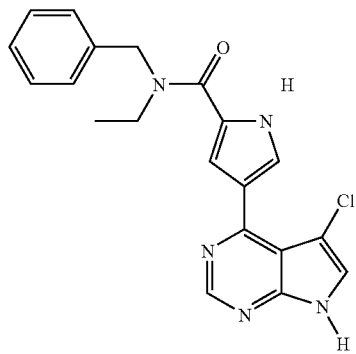 | 199 |
| 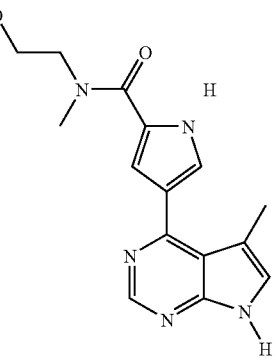 | 200 |
| 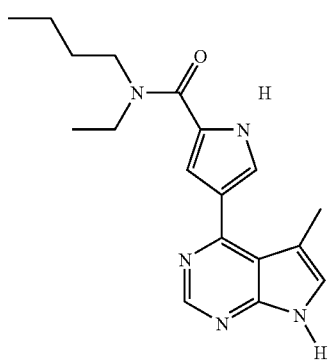 | 201 |
| 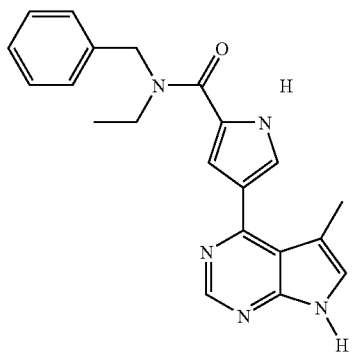 | 202 |
| 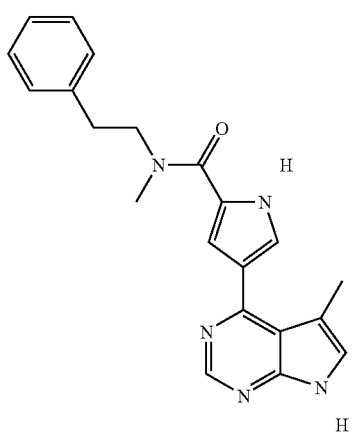 | 203 |

TABLE 2-continued
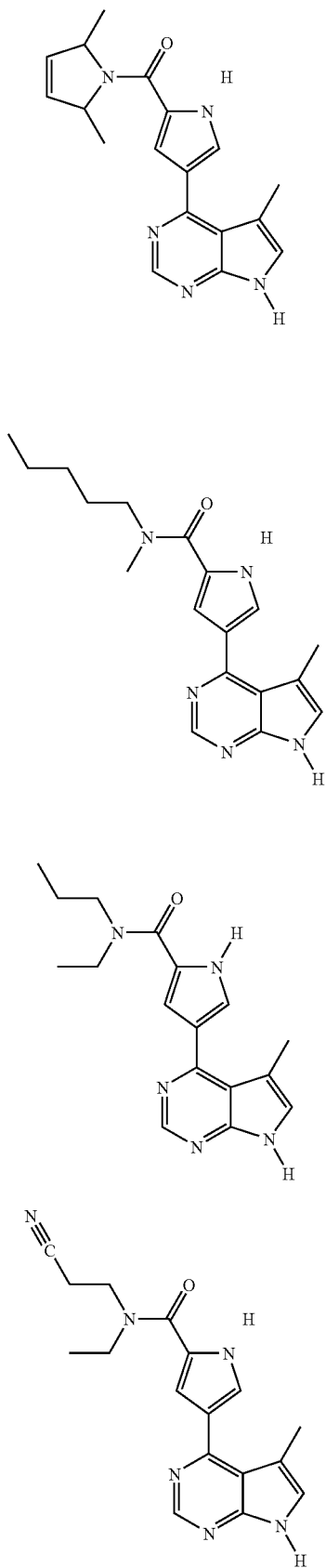
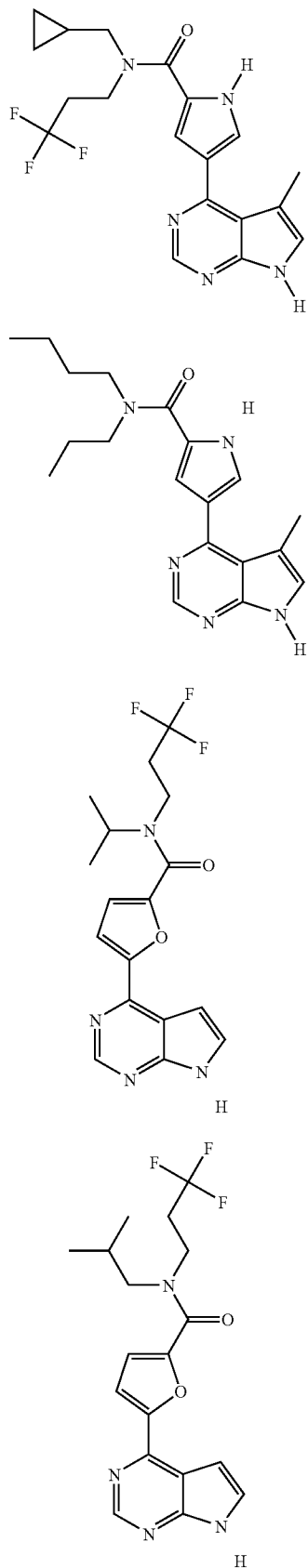

TABLE 2-continued
212 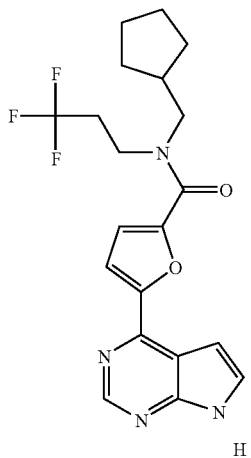
213 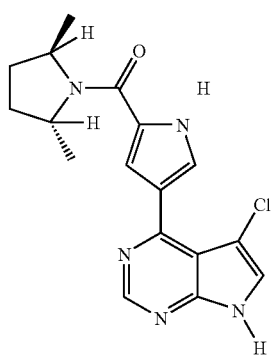
214 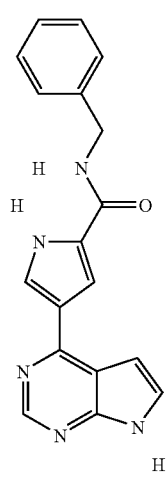
TABLE 2-continued
215 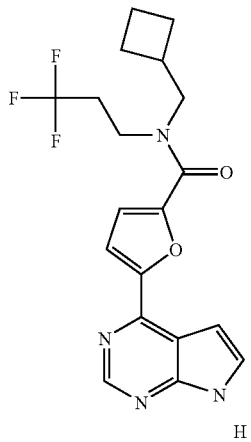
216 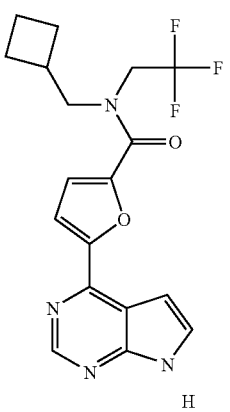
217 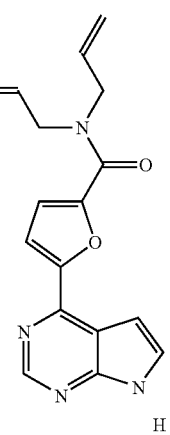
218 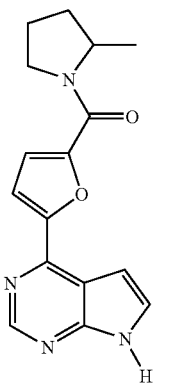 [SMILES: CC1CCCN1C(=O)c1ccc(-c2ncnc3[nH]ccc23)o1]

TABLE 2-continued
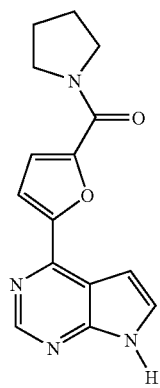 [SMILES: O=C(c1ccc(-c2ncnc3[nH]ccc23)o1)N1CCCC1]
219
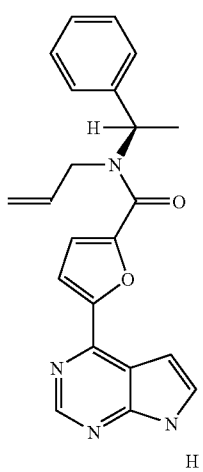
220
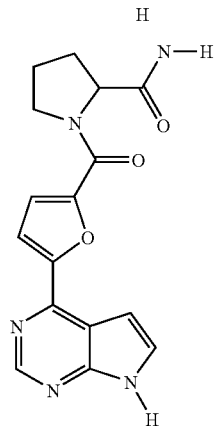
221
TABLE 2-continued
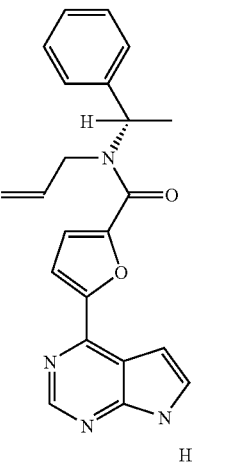
222
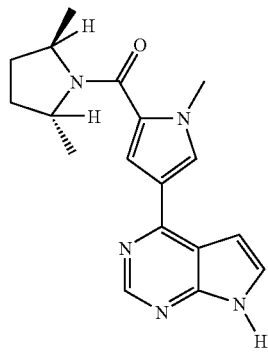 [SMILES: C[C@@H]1CC[C@@H](C)N1C(=O)c1cc(-c2ncnc3[nH]ccc23)cn1C]
223
224

TABLE 2-continued
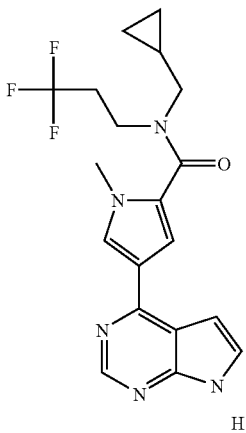
225
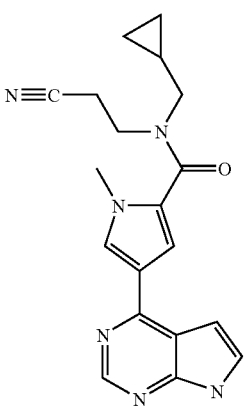
226
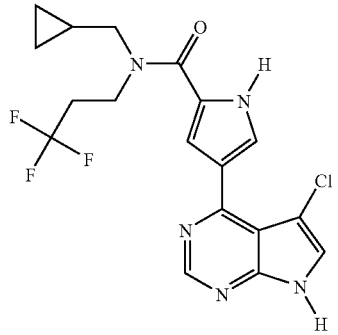 [SMILES: O=C(c1cc(-c2ncnc3[nH]cc(Cl)c23)c[nH]1)N(CCC(F)(F)F)CC1CC1]
227
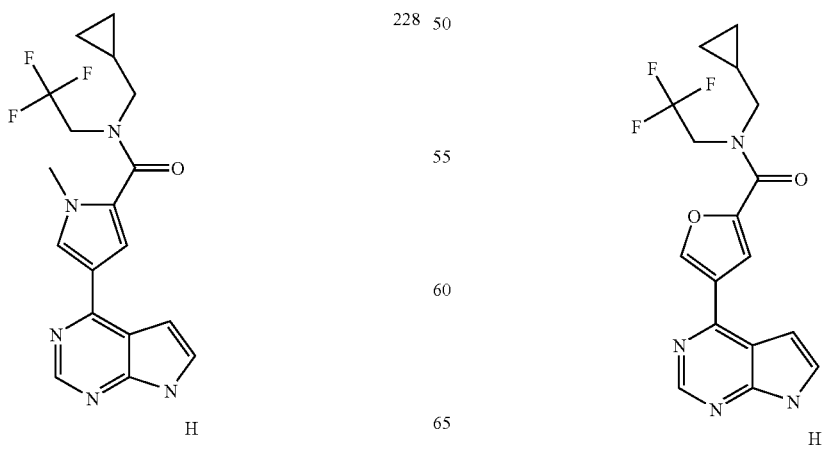
228
TABLE 2-continued
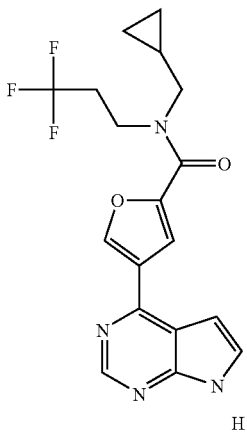
229
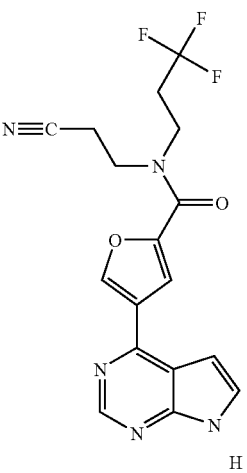
230
231

TABLE 2-continued
| | |
|---|---|
| 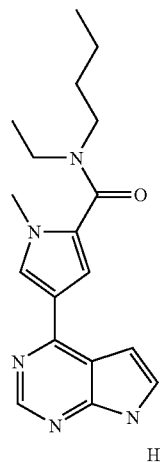 232 | 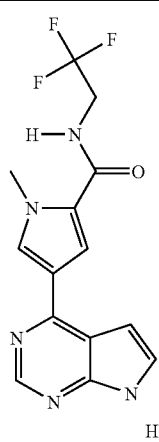 235 |
| 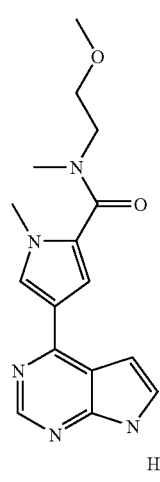 233 |  236 |
| 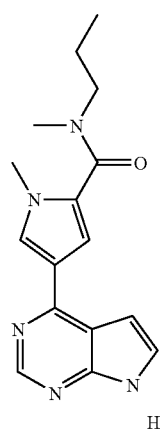 234 | 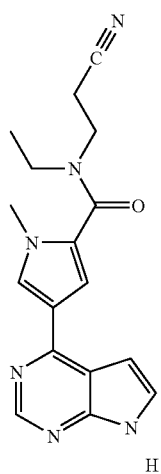 237 |

TABLE 2-continued
238 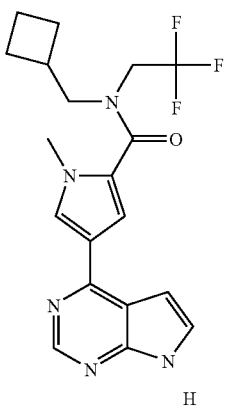
239 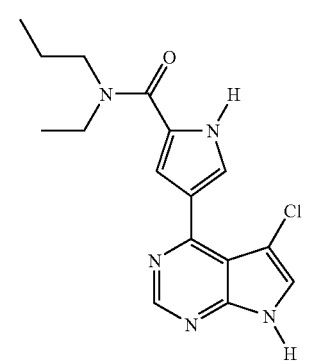 [SMILES: CCCN(CC)C(=O)c1cc(-c2ncnc3[nH]cc(Cl)c23)c[nH]1]
240 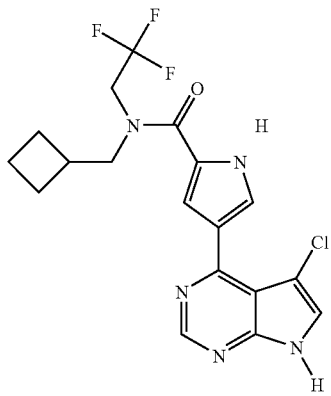
241 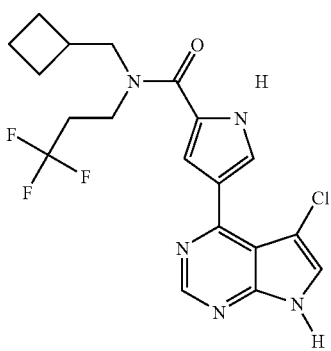
TABLE 2-continued
242 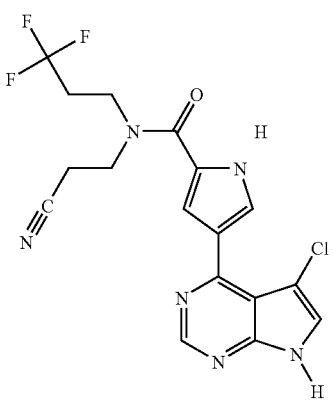
243 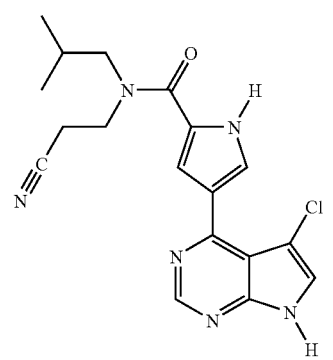 [SMILES: CC(C)CN(CCC#N)C(=O)c1cc(-c2ncnc3[nH]cc(Cl)c23)c[nH]1]
244 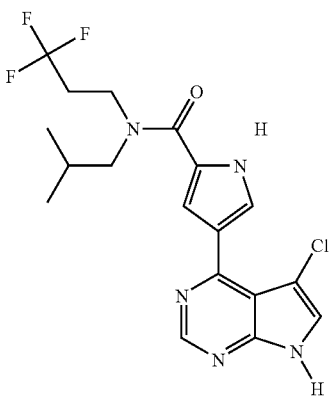
245 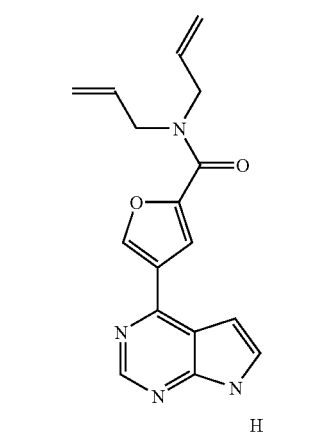

TABLE 2-continued
| | |
|---|---|
| 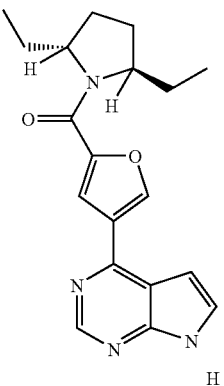 | 246 |
| 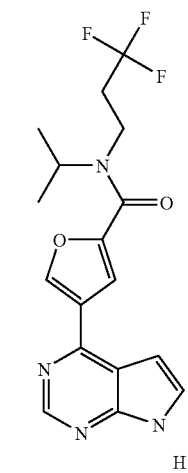 | 247 |
| 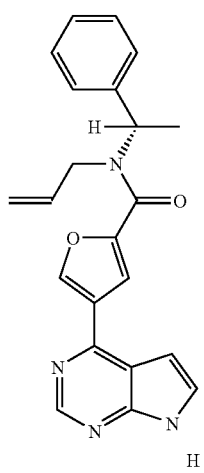 | 248 |
TABLE 2-continued
| | |
|---|---|
| 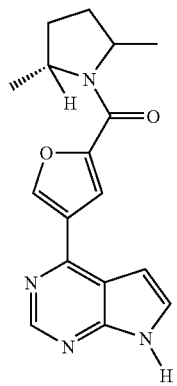 [SMILES: CC1CC[C@@H](C)N1C(=O)c1cc(-c2ncnc3[nH]ccc23)co1] | 249 |
| 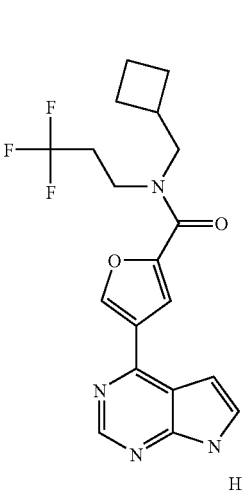 | 250 |
| 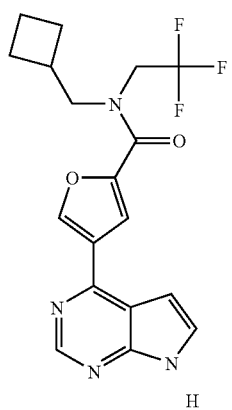 | 251 |

TABLE 2-continued

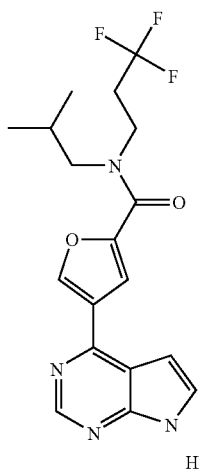
252

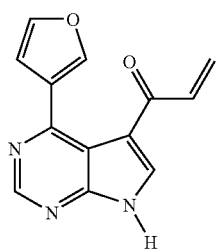 [SMILES: C=CC(=O)c1c[nH]c2ncnc(-c3ccoc3)c12]
253

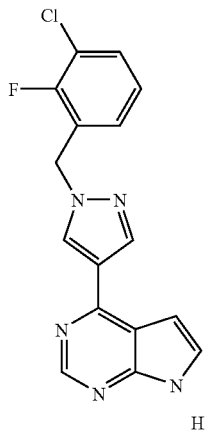
254

Uses, Formulation and Administration
Pharmaceutically Acceptable Compositions

In another embodiment, the invention provides a pharmaceutical composition comprising a compound of formulae I or II.

In a further embodiment, the composition additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

According to another embodiment, the invention provides a composition comprising a compound of this invention or a pharmaceutically acceptable derivative thereof and a pharmaceutically acceptable carrier, adjuvant, or vehicle. The amount of compound in the compositions of this invention is such that is effective to measurably inhibit a protein kinase, particularly a JAK family kinase, in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitorily active metabolite or residue thereof" means that a metabolite or residue thereof is also an inhibitor of a JAK family kinase.

As used herein, the term "pharmaceutically acceptable salt" refers to those salts which are, within the scope of sound medical judgement, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The term "measurably inhibit", as used herein means a measurable change in kinase activity, particularly JAK kinase activity, between a sample comprising a compound of this invention and a JAK kinase and an equivalent sample comprising JAK kinase in the absence of said compound.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Exce-lon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions

In one embodiment, the invention provides a method of inhibiting JAK kinase activity in a patient, comprising administering to said patient a compound or composition of the invention.

In another embodiment, the invention comprises a method of treating or lessening the severity of a JAK-mediated condition or disease in a patient. The term "JAK-mediated disease", as used herein means any disease or other deleterious condition in which a JAK family kinase, in particular JAK2 or JAK3, is known to play a role. In a further embodiment, the invention comprises a method of treating a JAK3-mediated disease. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas. In another embodiment, the invention comprises a method for treating a JAK2-mediated disease, such as, for example, a myeloproliferative disease.

In another embodiment, the invention provides a method of treating or lessening the severity of a disease of condition selected from a proliferative disorder, a cardiac disorder, a neurodegenerative disorder, an autoimmune disorder, a condition associated with organ transplant, an inflammatory disorder, an immune disorder or an immunologically mediated disorder, comprising administering to said patient a compound or composition of the invention.

In a further embodiment, the method comprises the additional step of administering to said patient an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders, wherein said additional therapeutic agent is appropriate for the disease being treated and said additional therapeutic agent is administered together with said composition as a single dosage form or separately from said composition as part of a multiple dosage form.

In one embodiment, the disease or disorder is allergic or type I hypersensitivity reactions, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), schizophrenia, cardiomyocyte hypertrophy, reperfusion/ischemia, stroke, baldness, transplant rejection, graft versus host disease, rheumatoid arthritis, amyotrophic lateral sclerosis, and multiple sclerosis, and solid and hematologic malignancies such as leukemias and lymphomas. In a further embodiment, said disease or disorder is asthma. In another embodiment, said disease or disorder is transplant rejection.

In another embodiment, a compound or composition of this invention may be used to treat a myeloproliferative disorder. In one embodiment, the myeloproliferative disorder is polycythemia vera, essential thrombocythemia, or chronic idiopathic myelofibrosis. In another embodiment, the myeloproliferative disorder is myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML or juvenile myelomonocytic leukemia.

In another embodiment, the invention provides a method of inhibiting JAK kinase activity in a biological sample, comprising contacting said biological sample with a compound or composition of the invention.

The term "biological sample", as used herein, means an ex vivo sample, and includes, without limitation, cell cultures or extracts thereof, tissue or organ samples or extracts thereof, biopsied material obtained from a mammal or extracts thereof, and blood, saliva, urine, feces, semen, tears, or other body fluids or extracts thereof.

Inhibition of kinase activity, particularly JAK kinase activity, in a biological sample is useful for a variety of purposes that are known to one of skill in the art. Examples of such purposes include, but are not limited to, blood transfusion, organ transplantation, biological specimen storage, and biological assays.

In certain embodiments of the present invention an "effective amount" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like.

In an alternate embodiment, the methods of this invention comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug.

Methodology for Synthesis and Characterization of Compounds

The compounds of this invention may be prepared in general by methods known to those skilled in the art for analogous compounds or by those methods depicted in the Examples below. See, e.g., the examples described in WO 2005/095400 and WO 2006/127587, which are herein incorporated by reference in its entirety.

All references provided in the Examples are herein incorporated by reference. As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

General Synthetic Scheme

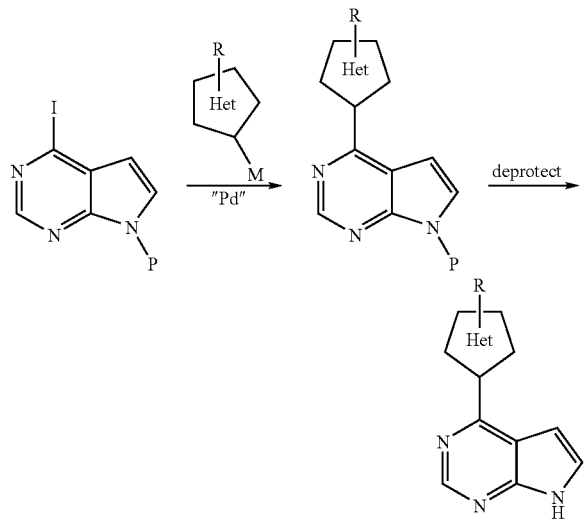

P = protecting group such as tosyl or mesyl, M = boronic acid, boronic ester, trialkylstannane or Zincate Compounds of the invention may be synthesized following the general approach outlined above. Starting with the appropriately protected 4-iododeazapurine, palladium-mediated cross coupling can be effected with heteroaryl boronic acids, or pinnacoleborane esters. Alternatively, heteroarylstannanes or arylzincates derived from the corresponding aryl halides can be used in cross coupling reactions. Deprotection of the deazapurine followed by further elaboration of the R group provides the desired compounds.

Exemplary heteroaryl precursors that may be used in the above-described synthetic scheme are described in the following publications: WO 2004/081008; WO 2005/063755; WO 2003/053925; Wendt et al., Bioorg. Med. Chem. Lett. 14(12): 3063-3068 (2004); Hocek et al., J. Med. Chem. 48 (18): 5869-5873 (2005); Malamas et al., J. Med. Chem. 47 (21): 5021-5040 (2004); Xu et al., Bioorg. Med. Chem. Lett. 15 (10): 2533-2536 (2005); and Advanced Synthesis & Catalysis 345 (9, 10): 1103- (2003). In addition, a number of heteroaryl precursors are available commercially.

EXAMPLES

Example 1

Preparation of Thiazolyl-Pyrrolo[2,3-d]Pyrimidines of the Invention

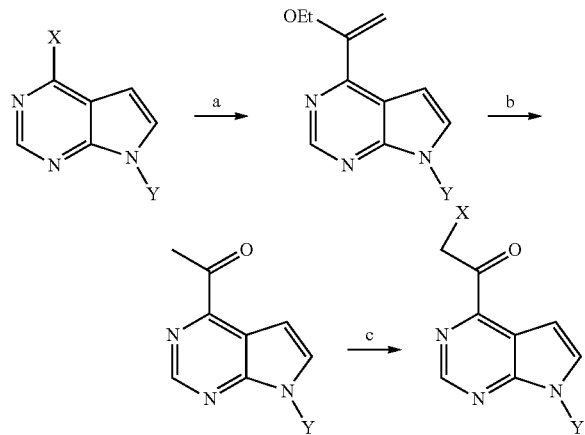

X is halogen; Y is protecting group (e.g., tosylate)
(a) tri-n-butyl(1-ethoxyvinyl) tin, Pd(PPh$_3$)$_2$Cl$_2$, toluene, 90° C.
(b) 6N HCl, MeOH, THF
(c) HBr, HOAc

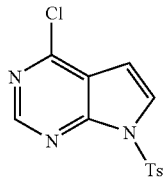 [SMILES: Cc1ccc(S(=O)(=O)n2ccc3c(Cl)ncnc32)cc1]

4-Chloro-7-(toluene-4-sulfonyl)-7H-pyrrolo[2,3-d]pyrimidine: To a solution of [10 g, 65.1 mmol] of 4-Chloro-7H-pyrrolo[2,3-d]pyrimidine in 250 mL of dry THF was cautiously added portionwise over 5 minutes time [2.86 g, 71.6 mmol] sodium hydride (60% oil dispersion). Reaction was then allowed to stir for 30 minutes at ambient temperature under a blanket of nitrogen gas. [12.96 g, 68.0 mmol] of solid toluene sulphonyl chloride was then added, in one portion and the reaction mixture was allowed to stir for one hour additional at ambient temperature. Ten mL of water was then cautiously added to the reaction (a quench for the excess hydride) and the solvent was removed under reduced pressure to ¼ the original volume. The residue was then suspended in 300 mL of water, stirred at ambient temperature for 30 minutes and isolated as a white solid via suction filtration. The material was washed with additional water and the damp cake was suspended in a minimum of acetonitrile and stirred overnight at ambient temperature. The precipitate was isolated via suction filtration and washed cautiously with cold acetonitrile and washed with hexanes; material air dried. Yield: 17.2 g of an off white solid (85%).

NMR: 500 MHz in CDCL3 δ8.75(s,1H), 8.09(d,2H J=8.5 Hz), 7.78(d,1H J=4.1 Hz), 7.36(d,2H J=8.5 Hz), 6.70(d,1H J=4.1 Hz), 2.4(s,3H)

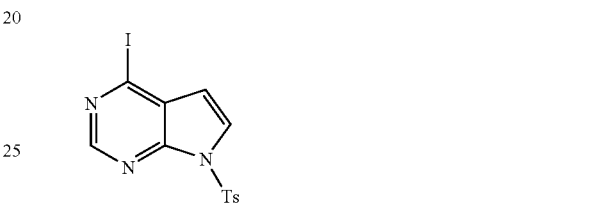

4-Iodo-7-(toluene-4-sulfonyl)-7H-pyrrolo[2,3-d]pyrimidine: [5 g. 16.2 mmol] of 4-Chloro-7-(toluene-4-sulfonyl)-7H-pyrrolo[2,3-d]pyrimidine was added in small portions, to 100 mL of cold stirring 47% stabilized hydriodic acid at 0° C. and stirred for one hour cold; the temperature was then allowed to warm to ambient temperature and stirred an additional 5 hrs. The reaction mixture was diluted with water and the solid was isolated via suction filtration, the solid being washed with additional water. The crude solid was dissolved in dichloromethane and washed twice with saturated sodium hydrogen carbonate solution, brined, dried (Na$_2$SO$_4$) and the solvent was removed under reduced pressure and triturated with a 2:1 mixture of hexanes/MTBE to yield 5.7 g of a white material (88%).

NMR: 500 MHz in CDCL3 δ8.61(s,1H), 8.06(d,2H J=8.5 Hz), 7.75(d,1H J=4.1 Hz), 7.32(d,2H J=8.5 Hz), 6.45(d,1H J=4.1 Hz), 2.4(s,3H)

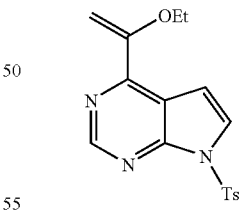

4-(1-Ethoxy-vinyl)-7-(toluene-4-sulfonyl)-7H-pyrrolo[2,3-d]pyrimidine: [10 g, 25 mmol] of 4-Iodo-7-(toluene-4-sulfonyl)-7H-pyrrolo[2,3-d]pyrimidine was dissolved/suspended in 200 mL of dry toluene along with [2.0 g, 2.85 mmol] of palladium (II) bis-triphenylphosphine dichloride. The mixture was purged with nitrogen gas for ~5 minutes before mixture was heated to 90° C. in an oil bath under an atmosphere of nitrogen gas. Added slowly dropwise over 2 hours, was [12.66 mL, 13.54 g, 37.5 mmol] of tri-n-butyl(1-ethoxyvinyl) tin in 100 mL of dry toluene. After completing the addition, the mixture was heated for an additional 6 hours under nitrogen. The reaction was cooled to ambient temperature and the solvent was removed under reduced pressure until the remaining volume was ⅕ the original. Added to this slurry was 160 mL of petroleum ether and the mixture was stirred for 1 hour, the solid being isolated via suction filtration and washed with petroleum ether. The damp solid was slurried in acetonitrile, stirred for one hour and the solid re-isolated via suction filtration and airdried. The resulting pale yellow solid, 7.2 g representing an 82% yield was utilized without further treatment.

NMR: 500 MHz in CDCL3 δ8.9(s,1H), 8.07(d,2H, J=8.5 Hz), 7.7(d,1H, J=4.1 Hz), 7.28(d,2H, J=8.5 Hz), 7.04(d,1H, J=4.1 Hz), 5.7(d,1H, J=2 Hz), 4.58(d,1H, J=2 Hz), 4.0(quart, 2H), 2.4(s,3H), 1.5(t,3H).

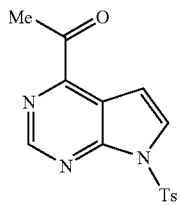

1-[7-(Toluene-4-sulfonyl)-7H-pyrrolo[2,3-d]pyrimidin-4-yl]-ethanone: [7.25 g, 21.12 mmol] of 4-(1-Ethoxy-vinyl)-7-(toluene-4-sulfonyl)-7H-pyrrolo[2,3-d]pyrimidine was dissolved in 50 mL each of methanol and THF and stirred with 10 mL of 6N HCL for 4.0 hours at ambient temperature. The solvents were removed under reduced pressure and the residue was partitioned between dichloromethane and saturated sodium hydrogen carbonate solution. The organic fraction was brined and dried with anhydrous sodium sulphate and the solvent was removed under reduced pressure. The crude material was triturated with a mixture of MTBE and petroleum ether (1:4) for several hours and the solid finally isolated via suction filtration and air dried. The 5.95 g of pale yellow material, representing a 89% yield was used without further purification.

NMR: 500 MHz CDCL3 δ9.0(s,1H), 8.08(d,2H, J=8.4 Hz), 7.87(d,1H, J=4.1 Hz), 7.3(m,3H), 2.8(s,3H), 2.4(s,3H).

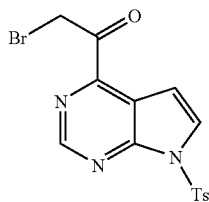 [SMILES: Cc1ccc(S(=O)(=O)n2ccc3c(C(=O)CBr)ncnc32)cc1]

2-Bromo-1-[7-(toluene-4-sulfonyl)-7H-pyrrolo[2,3-d]pyrimidin-4-yl]-ethanone: [5.95 g, 18.88 mmol] of 1-[7-(Toluene-4-sulfonyl)-7H-pyrrolo[2,3-d]pyrimidin-4-yl]-ethanone was dissolved/suspended in 90 mL of glacial acetic acid and [7.53 mL, 10.197 g, 37.76 mmol] of 30% hydrogen bromide in acetic acid. Added dropwise to this stirring mixture at ambient temperature, was [0.970 mL, 3.02 g, 18.88 mmol] of bromine in 10 mL of glacial acetic acid over 1.0 hour. The reaction was stirred an additional 4.0 hours at ambient temperature during which time a yellow precipitate forms. The solvent was removed under reduced pressure and the residue was partitioned between dichloromethane and saturated sodium hydrogen carbonate solution. The organic phase was washed with water, brine, and dried with anhydrous sodium sulphate and the solvent was removed under reduce pressure. The crude solid was triturated/stirred with MTBE overnight and the solid isolated via suction filtration and airdried to yield 4.2 g of pale yellow solid, a 56.6% yield.

NMR: 500 MHz in CDCL3 δ9.1(s,1H), 8.09(d,2H, J=8.5 Hz), 7.93(d,1H, J=4.0 Hz), 7.33(d,2H, J=8.5 Hz). 7.29(d,1H, J=4.0 Hz), 4.83(s,2H), 2.4(s,3H).

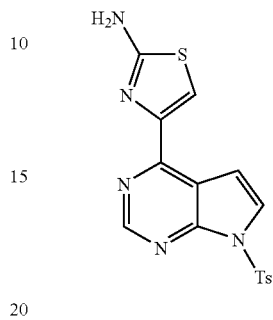

4-[7-(Toluene-4-sulfonyl)-7H-pyrrolo[2,3-d]pyrimidin-4-yl]-thiazol-2-ylamine: Into 75 mL of acetone was successively added [4.2 g, 10.65 mmol] of 2-Bromo-1-[7-(toluene-4-sulfonyl)-7H-pyrrolo[2,3-d]pyrimidin-4-yl]-ethanone followed by [0.81 g, 10.65 mmol] of thiourea. The reaction was then stirred for 4.0 hours at ambient temperature. The pale yellow precipitate was collected via suction filtration and washed with more acetone. The crude cake was suspended into 20 mL of triethylamine and stirred for one hour. The material was then diluted with water and suction filtered to isolate the solid. The damp cake was triturated with acetonitrile, the solid isolated again via suction filtration and airdried. The beige solid, 2.6 g, represents a 72% yield of the free base.

NMR: 500 MHz in CDCL3 δ8.92(s,1H), 8.08(d,2H, J=8.5 Hz), 7.73(d,1H, J=4.1 Hz), 7.70(s,1H), 7.42(d,1H, J=4.1 Hz), 7.28(d,2H, J=8.5 Hz), 5.1(br m,2H, exch), 2.4(s,3H).

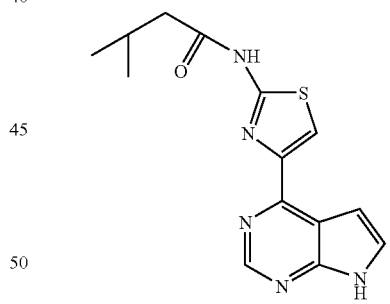

3-Methyl-N-[4-(1H-pyrrolo[2,3-b]pyridin-4-yl)-thiazol-2-yl]-butyramide (Compound 31): To a solution of [60 mg, 0.1615 mmols] of 4-[7-(Toluene-4-sulfonyl)-7H-pyrrolo[2, 3-d]pyrimidin-4-yl]-thiazol-2-ylamine in 1 mL of dry pyridine contained in a microwave vial, was added successively; [46 mg, 0.242 mmol] of EDCI, and [27 uL, 25 mg, 0.242 mmol] of isovaleric acid. The reaction was heated via microwave to 150° C. (150 W) for 10 minutes. The vial was opened and the pyridine was removed under a nitrogen stream before the residue was re-dissolved in a mixture of THF/methanol (2:1). To this solution was added, 3 drops of 50% sodium hydroxide and the reaction was stirred for approx one hour at ambient temperature. The hydrolysis was determined to be complete by HPLC and reaction was brought to low pH by addition of conc. Hydrochloric acid (11.0M). The solvents were removed via a stream of nitrogen gas and residue was dissolved in DMSO and particulates allowed to settle before purifying the crude material via $C_{18}$ HPLC utilizing water/acetonitrile/trifluoroacetic acid as the eluent. This yielded 14 mg of the final product as the TFA salt after lyophilization of the aqueous HPLC fractions; a 20.8% yield.

All other amide derivatives synthesized from 4-[7-(Toluene-4-sulfonyl)-7H-pyrrolo[2,3-d]pyrimidin-4-yl]-thiazol-2-ylamine were accomplished in an analogous manner.

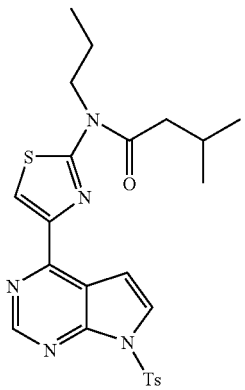 [SMILES: CCCN(C(=O)CC(C)C)c1nc(-c2ncnc3c2ccn3S(=O)(=O)c2ccc(C)cc2)cs1]

3-Methyl-N-propyl-N-{4-[7-(toluene-4-sulfonyl)-7H-pyrrolo[2,3-d]pyrimidin-4-yl]-thiazol-2-yl}-butyramide: [100 mg; 0.22 mmol] of 3-Methyl-N-{4-[1-(toluene-4-sulfonyl)-1H-pyrrolo[2,3-b]pyridin-4-yl]-thiazol-2-yl}-butyramide was dissolved in 1 mL of dry DMF and to this solution was added [13.0 mg; 0.27 mmol] of sodium hydride (60% in oil dispersion) and the reaction was stirred at 40° C. for 10 minutes before addition of [21.5 uL; 37.37 mg; 0.22 mmol] of n-propyliodide, in one portion. The reaction was stirred for one hour more at 40° C. After reaction was determined to be complete, the solvent was removed under reduced pressure and residue triturated with methyl t-butyl ether and filtrate decanted away from oil. The trituration was performed again and the crude reaction mixture stirred overnight at ambient temperature, the material solidifies. The material was isolated via suction filtration and washed with more ether, again with petroleum ether and air dried. This provides a dark beige powder; 83 mg representing a 76% yield.

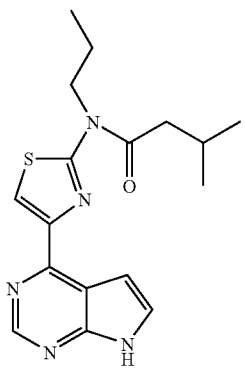 [SMILES: CCCN(C(=O)CC(C)C)c1nc(-c2ncnc3[nH]ccc23)cs1]

3-Methyl-N-propyl-N-[4-(7H-pyrrolo[2,3-d]pyrimidin-4-yl)-thiazol-2-yl]-butyramide (Compound 103): To 55 mg [0.11 mmol] of 3-Methyl-N-propyl-N-{4-[7-(toluene-4-sulfonyl)-7H-pyrrolo[2,3-d]pyrimidin-4-yl}-butyramide dissolved in 2 mL of dry THF was added 5 drops of a 1M tetra n-butylammonium fluoride solution in THF, the vial was capped and heated/stirred at 80° C. for 4 hours. Reaction determined to be complete via HPLC and reaction was cooled. The solvent was removed under an $N_2$ stream and residue was partitioned between DCM and water. The organic layer was brined and dried with anhydrous sodium sulphate and the solvent removed under vacuum. The crude product was purified on $C_{18}$ silica with water/acetonitrile/TFA as the eluent, isolating 15 mg of a yellow solid which constituted a 39% yield.

Example 2

Preparation of Pyrrolyl-Pyrrolo[2,3-d]Pyrimidines of the Invention

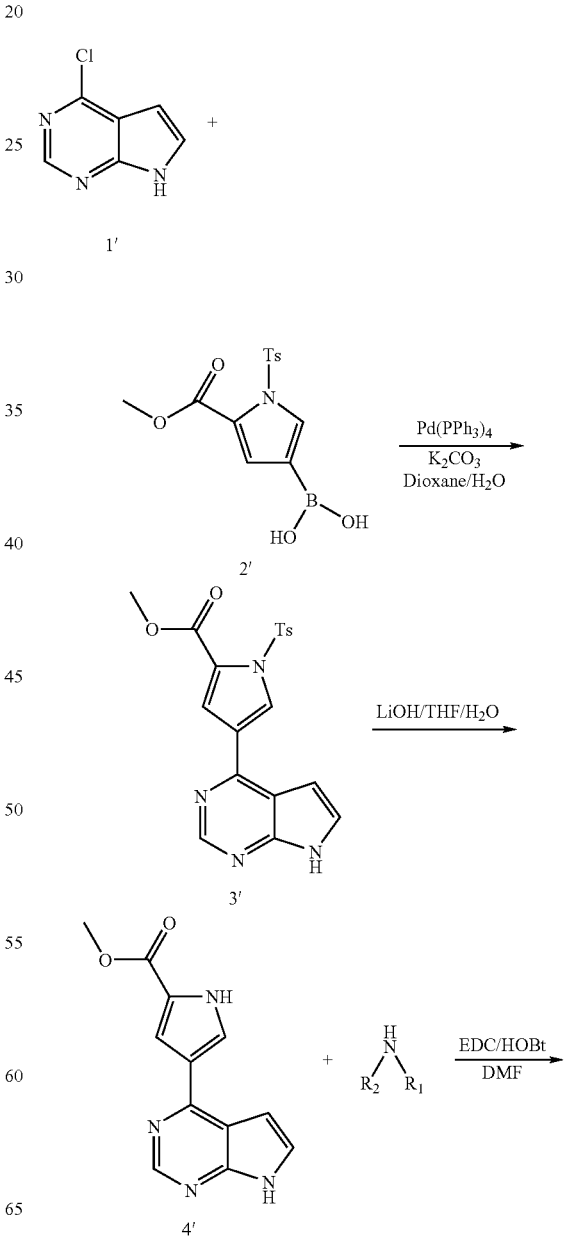

-continued

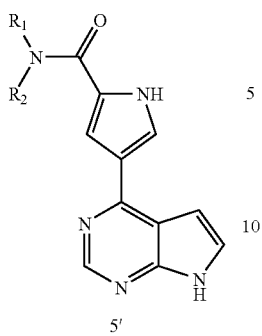

5'

4-(7H-Pyrrolo[2,3-d]pyrimidin-4-yl)-1-(toluene-4-sulfonyl)-1H-pyrrole-2-carboxylic acid methyl ester (3') Under $N_2$, Compound 1' (1.3 g, 8.49 mmol) and compound 2' (1.1 equivalent, 9.34 mmol) and $K_2CO_3$ (3.3 equivalent, 28 mmol) were dissolved into 9 mL of dioxane and 3 mL of $H_2O$ in a microwave. To this reaction mixture, catalytic amount of $Pd(PPh_3)_4$ was added and the tube was under microwave irradiation at 170° C. for 10 min. After cooled down the reaction mixture, the product crashed out and filtered off the solid, washed with $H_2O$ and $CH_3CN$ respectively to obtain title compound 3' quantitatively. MS+1=397.2.

4-(7H-Pyrrolo[2,3-d]pyrimidin-4-yl)-1H-pyrrole-2-carboxylic acid (4') To a microwave tube with compound 3' from previous step, LiOH (4 equivalent, 33.96 mmol) was added, followed by THF (8 mL) and $H_2O$ (4 mL). The reaction mixture was microwave irradiated at 150° C. for 10 min. Poured reaction mixture into a beaker, and 2N HCl was added to the reaction mixture drop wise to adjust the pH of the solution to 4-5. In the process of acidifying the solution, precipitation was formed, filtered off the solid and washed with $H_2O$ extensively and then small amount of $CH_3CN$. Dried to give title compound 4' quantitatively. MS+1=229.1

4-(7H-Pyrrolo[2,3-d]pyrimidin-4-yl)-1H-pyrrole-2-carboxylic acid amide (5') To a vial with Compound 4' (0.1 mmol) in DMF (1 mL), EDC (2 equivalent, 0.2 mmol) and HOBt (0.5 equivalent, 0.05 mmol) were added and the reaction mixture was stirred at room temperature for half an hour. Amine (1.2 equivalent, 0.12 mmol) was added and the reaction mixture was stirred at room temperature for 2-3 hour. Reverse phase HPLC was used to purify the final compound.

Example 3

Preparation of Furanyl-Pyrrolo[2,3-d]Pyrimidines of the Invention

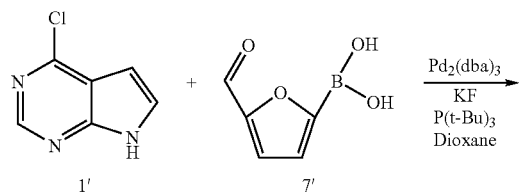

-continued

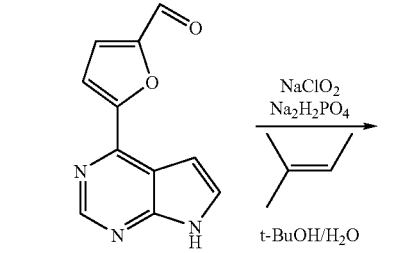

8'

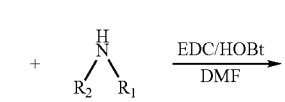

9'

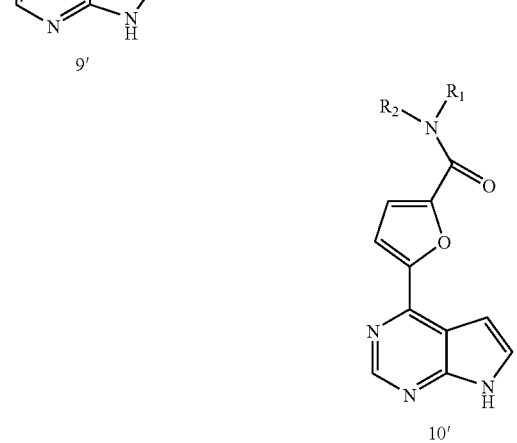

10'

5-(7H-Pyrrolo[2,3-d]pyrimidin-4-yl)-furan-2-carbaldehyde (8') Under $N_2$, Compound 1' (0.875 g, 5.7 mmol) and compound 7' (1.01 g, 7.2 mmol) and KF (3.3 equivalent, 18.8 mmol) were dissolved into 10 mL of dioxane in a microwave. To this reaction mixture, catalytic amount of $Pd_2(dba)_3$ (0.015% mol) and $P(t-Bu)_3$ (0.045% mol) were added, and the tube was microwave irradiated at 160° C. for 15 min. After it was concentrated down, $CH_3CN$ was added to the reaction mixture. The product precipitated out and the solid was filtered off, washed with $H_2O$ and $CH_3CN$ respectively to obtain title compound 8'. MS+1=214.1.

5-(7H-Pyrrolo[2,3-d]pyrimidin-4-yl)-furan-2-carboxylic acid (9') Sodium dihydrogen phosphate (210 mg, 1.75 mmol), 2-methyl-2-butene (0.742 mL, 7.0 mmol) and sodium chlorite (127 mg, 1.4 mmol) were consecutively added to a solution of compound 8' (74.5 mg, 0.35 mmol) in t-BuOH (6 mL) and $H_2O$ (2.4 mL) at 0° C. under $N_2$, and the solution was stirred at room temperature over night. Water was added to the solution and the aqueous layer was adjusted to pH 2 with 20% aqueous solution of phosphoric acid. A precipitate was formed, was filtered off, washed with $H_2O$, and dried to give the title compound 9' (32 mg, 40%).

5-(7H-Pyrrolo[2,3-d]pyrimidin-4-yl)-furan-2-carboxylic acid amide (10') To a vial with Compound 9' (0.1 mmol) in DMF (1 mL), EDC (2 equivalent, 0.2 mmol) and HOBt (0.5 equivalent, 0.05 mmol) were added and the reaction mixture was stirred at room temperature for half an hour. Amine (1.2 equivalent, 0.12 mmol) was added and the reaction mixture was stirred at room temperature for 2-3 hour. Reverse phase HPLC was used to purify the final compound.

Example 4

Preparation of Pyrazolyl-Pyrrolo[2,3-d]Pyrimidines of the Invention

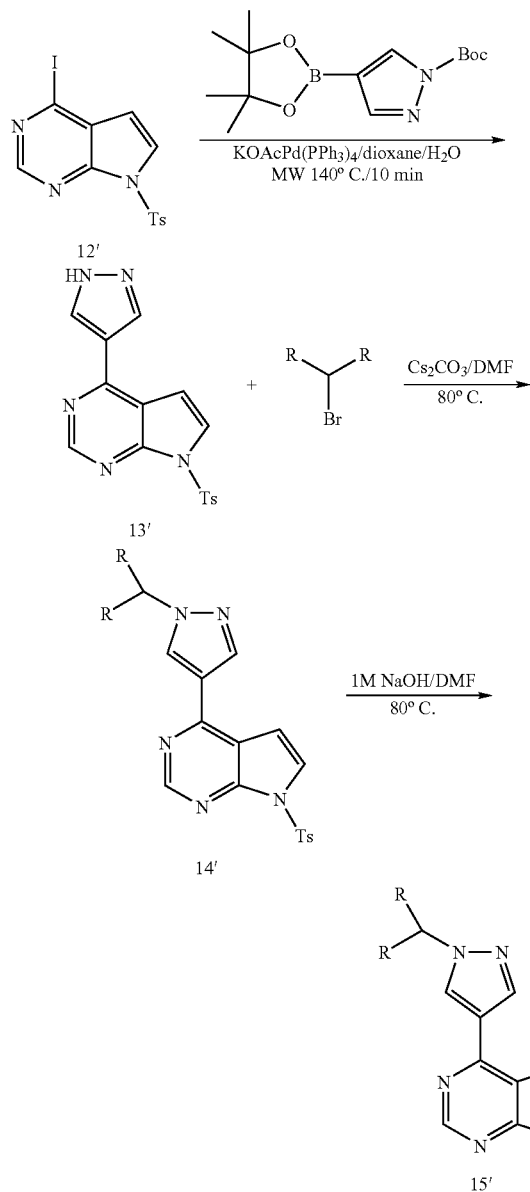

4-(1H-pyrazo-4-yl)-7-tosyl-7H-pyrrolo[2,3-d]pyrimidine (13'): The reaction mixture of 4-iodo-7-tosyl-7H-pyrrolo[2,3-d]pyrimidine (12', 0.800 g, 2 mmol), tert-butyl 4-(4,4,5,5-tetramethyl-1,3,2-dioxaborolan-2-yl)-1-H-pyrazole-1-carboxylate, 3.5 ml 2M KOAc, 0.12 g (0.1 mmol) Palladium tetrakistriphenylphosphine and 10 ml 1,4-dioxane was deoxygenated by bubbling $N_2$ for 20 min. The reaction mixture was heated at 140° C. on microwave synthesizer for 10 min. Work up: The reaction mixture was cooled to room temperature and filtered. The filtration cake is 2.0 g 95% pure title product, yield 50%.

4-(1-(Hexan-3-yl)-1H-pyrazol-4-yl)-7-tosyl-7H-pyrrolo-[2,3-d]pyrimidine (example of 14'): The DMF suspension of 4-(1H-pyrazo-4-yl)-7-tosyl-7H-pyrrolo-[2,3-d]pyrimidine, 3-bromohexane and $CsCO_3$ was stirred at 80° C. for overnight. LC/MS indicated the product peak and some starting material. No work up and the reaction material was carried on for next step. No yield was calculated.

4-(1-(hexan-3-yl)-1H-pyrazol-4-yl)-7H-pyrrolo[2,3-d]pyrimidine (example of 15', Compound 94): To the crude product mixture of 4-(1-(hexan-3-yl)-1H-pyrazol-4-yl)-7-tosyl-7H-pyrrolo-[2,3-d]pyrimidine was added 1 mL 1M NaOH solution, the reaction mixture was stirred at 80° C. for 3 h. LC/MS indicated no starting material. Work up: The reaction mixture was filtered through syringe filter and injected on to prep HPLC, the product fraction was collected and dried on EZ 2-plus. No yield was calculated.

Example 5

Preparation of Thiazolyl-Pyrrolo[2,3-d]Pyrimidines of the Invention

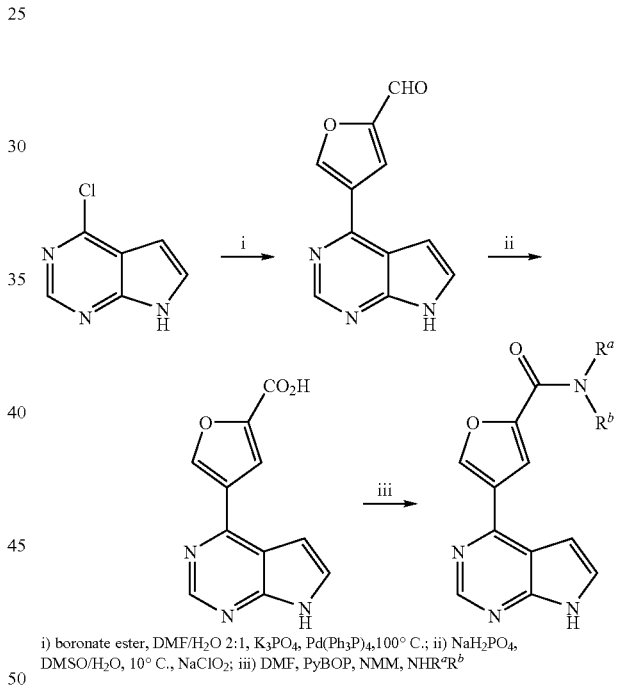

i) boronate ester, DMF/$H_2O$ 2:1, $K_3PO_4$, Pd(Ph$_3$P)$_4$,100° C.; ii) NaH$_2$PO$_4$, DMSO/$H_2O$, 10° C., NaClO$_2$; iii) DMF, PyBOP, NMM, NHR$^a$R$^b$ 4-(7H-pyrrolo[2,3-d]pyrimidin-4-yl)furan-2-carbaldehyde: 1 g [4.5 mMols] of 4-(4,4,5,5-tetramethyl-1,3,2-dioxaborolan-2-yl)furan-2-carbaldehyde, 550 mg [3.6 mMols]-4- chloro-7H-pyrrolo[2,3-d]pyrimidine and 1.52 g [6.7 mMols] of tripotassium phosphate were placed in 20 mL DMF and 10 mL water and purged with nitrogen gas while stirring for 10 minutes at ambient temperature. To this stirring suspension, 400 mg, 0.45 mMols] of tetrakistriphenylphosphine palladium (0) was added in one portion, and reaction vessel was placed in a preheated bath at 110° C. The reaction was stirred and heated under a nitrogen atmosphere for 30 minutes (deemed complete by analytical liquid chromatography). The reaction mixture was cooled and suction filtered to remove the ligand present as a precipitate, which was washed with a little DMF/H$_2$O 2:1. The combined filtrates were reduced in volume to one quarter of the original under reduced pressure and diluted slowly with water with stirring. The resulting fine precipitate was centrifuged down and the pellet was washed with more water, re-centrifuged and transferred to a RB with acetonitrile. This solvent was reduced to dryness under reduced pressure. The material, 670 mg (yield 87%) of a light beige powder was carried on without further purification. LC/ms m+1=214.

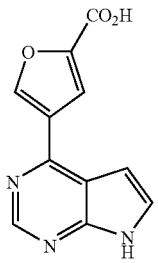

4-(7H-pyrrolo[2,3-d]pyrimidin-4-yl)furan-2-carboxylic acid: 600 mg [2.82 mMols] of 4-(7H-pyrrolo[2,3-d]pyrimidin-4-yl)furan-2-carbaldehyde was dissolved in 5.0 mL of DMSO/2.0 mL of water and stirred with 210 mg [1.75 mMols] of sodium dihydrogen phosphate, reducing the temperature as cold as possible so as not to effect crystallization. 532 mg sodium chlorite [5.88 mMols] in 4.0 mL of water was slowly added dropwise to this stirring solution. Solution was allowed to warm to ambient temperature and diluted with water to effect precipitation. The fine flocculent material was centrifuged down and washed with water and re-centrifuged. The oily pellet was transferred to a RB with acetonitrile and the solvents were removed under reduced pressure. The residue was stirred with a mixture of MTBE/acetonitrile (4:1) overnight and the powder isolated in the morning via suction filtration, washed with the same mixture and air dried. The material, (yield 64.6%) a beige powder, was utilized without further purification. LC/MS m+1 230/m−1 228.

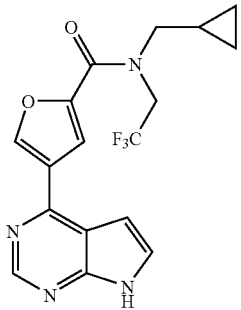 [SMILES: O=C(c1cc(-c2ncnc3[nH]ccc23)co1)N(CC1CC1)CC(F)(F)F]

N-(cyclopropylmethyl)-4-(7H-pyrrolo[2,3-d]pyrimidin-4-yl)-N-(2,2,2-trifluoroethyl)furan-2-carboxamide (Compound 231): 35 mg [0.153 mMols] of 4-(7H-pyrrolo[2,3-d]pyrimidin-4-yl)furan-2-carboxylic acid was dissolved in 1.5 mL of DMF and stirred with 120 mg [0.22 mMols] of PyBOP, 50 µL [46 mg, 0.46 mMols] of N-methylmorpholine, and 50 mg [0.26 mMols] of N-(2,2,2-trifluoroethyl) N-2-cyclopropylethylamine overnight at ambient temperature. The solvent was removed under a nitrogen stream at 30° C. and residue dissolved in methanol with several drops of TFA to protonate the amines present. The crude material was purified via C$_{18}$ silica utilizing a gradient of water/acetonitrile/TFA as an eluent 5%-95%. The product, 4 mg of a beige powder (after lyophilization of filtrates) was obtained; yield 9.5%.

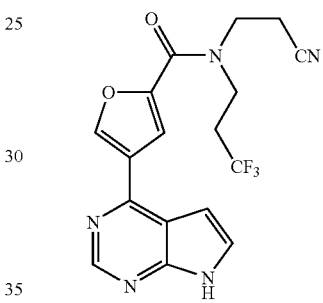

N-(2-cyanoethyl)-4-(7H-pyrrolo[2,3-d]pyrimidin-4-yl)-N-(3,3,3-trifluoropropyl)furan-2-carboxamide (Compound 230): In an analogous fashion, N-(2-cyanoethyl)-4-(7H-pyrrolo[2,3-d]pyrimidin-4-yl)-N-(3,3,3-trifluoropropyl)furan-2-carboxamide was prepared and purified to yield 6.0 mg of a beige powder, yield 7.9%.

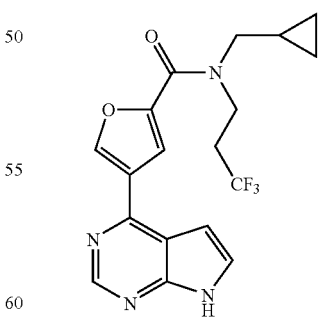

N-(cyclopropylmethyl)-4-(7H-pyrrolo[2,3-d]pyrimidin-4-yl)-N-(3,3,3-trifluoropropyl)furan-2-carboxamide (Compound 229): In an analogous fashion, N-(cyclopropylmethyl)-4-(7H-pyrrolo[2,3-d]pyrimidin-4-yl)-N-(3,3,3- trifluoropropyl)furan-2-carboxamide was prepared and purified to yield 4.0 mg of a beige powder, yield 5.2%.

Example 6

Preparation of Furanyl-Pyrrolo[2,3-d]Pyrimidines of the Invention

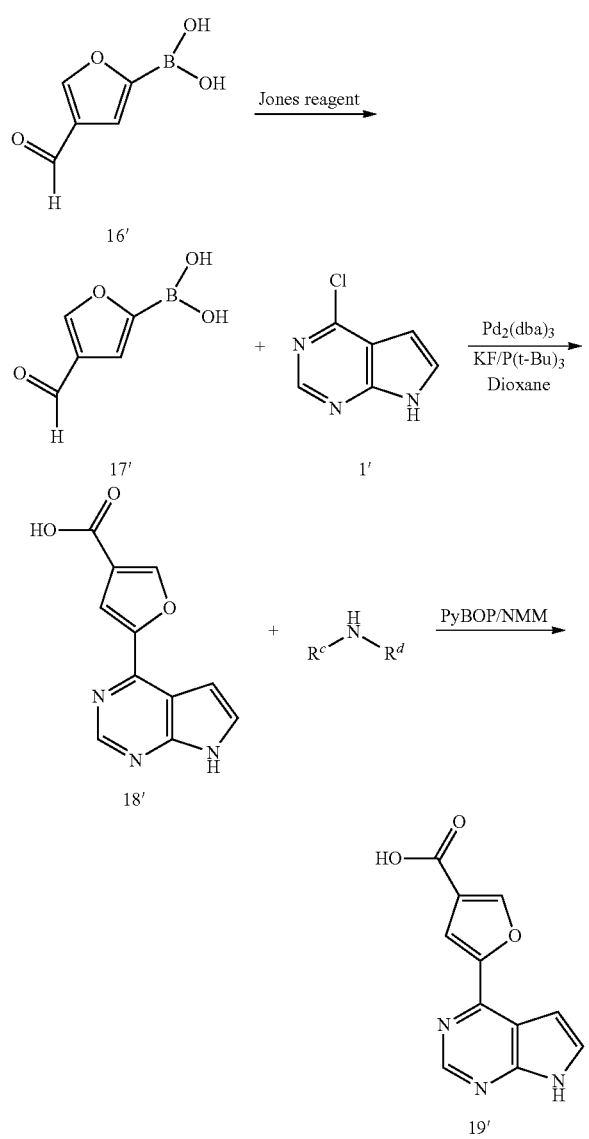

5-boronofuran-3-carboxylic acid (17'): 139 mg compound 16' [1 mmol] was dissolved into 3 mL acetone at 0° C., to which 5 equivalent of Jones Reagent was added slowly during the course of 5 min. The reaction mixture was stirred at room temperature for 1 hour, the reaction mixture was poured into 10 mL of ether and the solid filtered off. The ether was removed to give the crude compound 2. MS−1=155.0.

5-(1H-pyrrolo[2,3-b]pyridin-4-yl)furan-3-carboxylic acid (18'): To a microwave tube with 50 mg compound 17' [0.32 mmol], 2 mL of dioxane was added, followed by compound 1' (1.1 equiv.), KF (3.3 equiv.), $Pd_2(dba)_3$ (10% mol equiv.) and $P(t-Bu)_3$ (30% mol equiv) and the reaction tube was subjected to microwave irradiation for 15 min. at 160° C. After the reaction cooled down, the solid was filtered off, washed with small amount of $CH_3CN$ to give the title compound 18'. MS+1=229.9.

5-(1H-pyrrolo[2,3-b]pyridin-4-yl)furan-3-carboxamide (19'): To a vial with compound 18' (0.1 mmol) in DMF (1 mL), PyBOP (2 equivalent, 0.2 mmol) and NMM (2 equivalent, 0.2 mmol) were added and the reaction mixture was stirred at room temperature for half an hour. The desired amine (1.2 equivalent, 0.12 mmol) was added and the reaction mixture was stirred at room temperature for 2-3 hour. Reverse phase HPLC was used to purify the final compound 19'.

Other compounds of the invention may be synthesized in analogous fashion to those examples presented herein.

Example 7

Analytical Results

Tables 3 and 4 below depict exemplary $^1$H-NMR data (NMR) and liquid chromatographic mass spectral data, reported as mass plus proton (M+H), as determined by electrospray, and retention time (RT) for certain compounds of the present invention, wherein compound numbers in Tables 3 and 4 correspond to the compounds depicted in Tables 1 and 2 respectively (empty cells in the NMR column indicate that results were not available). If multiple lots were made and tested, only the results from the first lot tested are depicted.

TABLE 3

| Cpd # | M + H | RT | NMR |
|---|---|---|---|
| 1 | 382.00 | 2.00 | (CD3OD) 3.85 (m, 2H), 5.15 (t, 1H), 7.2 (m, 1H), 7.3 (m, 3H), 7.4 (s, 1H), 7.8 (m, 2H), 8.1 (s, 1H), 8.8 (s, 1H) |
| 2 | 202.10 | 1.60 | (500 MHz, dmso-d6) 12.3 (s, 1H), 8.81 (s, 1H), 8.55 (d, 1H), 7.96 (dd, 1H), 7.70 (d, 1H), 7.05 (d, 1H) ppm |
| 3 | 200.20 | 1.30 | (500 MHz, dmso-d6) 12.7 (s, 1H), 8.88 (s, 1H), 8.79 (s, 1H), 8.38 (s, 1H), 7.77 (s, 1H), 7.14 (s, 1H), 3.99 (s, 3H) ppm |
| 4 | 186.20 | 2.20 | (500 MHz, dmso-d6) 12.3 (s, 1H), 8.82 (d, 1H), 8.64 (s, 1H), 8.00 (m, 1H), 7.60 (m, 1H), 7.12 (m, 1H), 6.66 (m, 1H) ppm |

TABLE 3-continued

| Cpd # | M + H | RT | NMR |
|---|---|---|---|
| 5 | 186.20 | 2.20 | |
| 6 | 296.10 | 1.50 | (500 MHz, DMSO-d6) 12.51 (s, 1H), 8.80 (d, J = 10.7 Hz, 2H), 8.40 (s, 1H), 7.72 (s, 1H), 7.11 (s, 1H), 4.39-4.33 (m, 2H), 2.36-2.26 (m, 2H), 2.14-2.06 (m, 2H) |
| 7 | 310.30 | 1.59 | |
| 8 | 270.30 | 1.49 | |
| 9 | 284.30 | 1.63 | |
| 10 | 292.30 | 1.44 | |
| 11 | 298.40 | 1.74 | |
| 12 | 268.30 | 1.40 | |
| 13 | 296.30 | 1.67 | |
| 14 | 266.30 | 1.37 | |
| 15 | 267.30 | 1.30 | |
| 16 | 308.80; 309.20 | 1.37; 1.45 | (500 MHz, MeOD) 8.82 (s, H), 8.14 (d, J = 1.4 Hz, 1H), 7.80 (d, J = 3.7 Hz, 1H), 7.46 (d, J = 1.5 Hz, 1H), 7.25 (d, J = 3.7 Hz, 1H), 3.87 (s, 4H), 3.34 (s, H), 2.91 (t, J = 6.7 Hz, 2H), 1.41 (t, J = 6.8 Hz, 3H), |
| 17 | 308.20 | 1.70 | |
| 18 | 372.30 | 1.13 | |
| 19 | 323.30 | 1.70 | |
| 20 | 324.30 | 1.85 | |
| 21 | 323.30 | 1.60 | |
| 22 | 337.30 | 1.70 | |
| 23 | 295.20 | 1.30 | |
| 24 | 280.20 | 1.40 | |
| 25 | 344.30 | 1.38 | |
| 26 | 312.30 | 1.80 | |
| 27 | 298.30 | 1.70 | |
| 28 | 340.30 | 2.00 | |
| 29 | 371.30 | 1.80 | |
| 30 | 346.30 | 1.90 | |
| 31 | 302.00 | 2.00 | 500 MHz/DMSO-d6: 12.3 (br s, 1H), 12.17 (s, 1H), 8.8 (s, 1H), 8.25 (s, 1H), 7.7 (m, 1H), 7.35 (m, 1H), 2.4 (d, 2H), 2.1 (sept, 1H), 097 (d, 6H) |
| 32 | 328.00 | 2.20 | 500 MHz/DMSO-d6: 12.3 (br s, 1H), 12.17 (s, 1H), 8.8 (s, 1H), 8.2 (s, 1H) 7.7 (m, 1H), 7.3 (m, 1H), 2.57 (d, 2H under DMSO peak), 2.27 (quint, 1H) 1.78 (m, 2H), 1.6 (m, 2H), 1.53 (m, 2H), 1.2 (m, 2H) |
| 33 | 358.00 | 2.70 | 500 MHz/DMSO-d6: 12.3 (br s, 1H), 12.17 (s, 1H), 8.8 (s, 1H), 8.2 (s, 1H) 7.73 (m, 1H), 7.33 (m, 1H), 2.57 (dd, 1H under DMSO peak), 2.37 (dd, 1H), 2.1 (m, 1H), 1.33 (dd, 1H), 1.15 (dd, 1H), 0.97 (d, 3H), 0.9 (s, 9H) |
| 34 | 228.20 | 1.39 | (500 MHz, Methanol-d4) 8.85 (s, 1H), 8.77 (s, 1H), 8.43 (s, 1H), 7.83 (d, J = 3.7 Hz, 1H), 7.30 (d, J = 3.7 Hz, 1H), 4.74 (qn, J = 6.7 Hz, 1H), 1.61 (d, J = 6.7 Hz, 6H), 0.00 (TMS) |
| 35 | 242.30 | 1.56 | (500 MHz, Methanol-d4) 8.86 (s, 1H), 8.79 (s, 1H), 8.45 (s, 1H), 7.84 (d, J = 3.7 Hz, 1H), 7.31 (d, J = 3.7 Hz, 1H), 4.51-4.47 (m, 1H), 2.05-1.98 (m, 1H), 1.95-1.89 (m, 1H), 1.59 (d, J = 6.8 Hz, 3H), 0.87 (t, J = 7.4 Hz, 3H), 0.00 (TMS) |
| 36 | 253.30 | 1.69 | (500 MHz, Methanol-d4) 8.86 (s, 1H), 8.78 (s, 1H), 8.44 (s, 1H), 7.85 (d, J = 3.7 Hz, 1H), 7.31 (d, J = 3.7 Hz, 1H), 4.94-4.90 (m, 1H), 2.29-2.24 (m, 2H), 2.16-2.09 (m, 2H), 1.98-1.93 (m, 2H), 1.83-1.79 (m, 2H), 0.00 (TMS) |
| 37 | 284.30 | 2.17 | (500 MHz, Methanol-d4) 8.85 (s, 1H), 8.78 (s, 1H), 8.46 (s, 1H), 7.84 (d, J = 3.7 Hz, 1H), 7.29 (d, J = 3.6 Hz, 1H), 4.44-4.40 (m, 1H), 2.03-1.96 (m, 2H), 1.87-1.80 (m, 2H), 1.31-1.24 (m, 2H), 1.17-1.12 (m, 2H), 0.94 (t, 3H), 0.00 (TMS)-0.04 (s, H), |
| 38 | 256.30 | 1.78 | (500 MHz, Methanol-d4) 8.86 (s, 1H), 8.79 (s, 1H), 8.45 (s, 1H), 7.85 (d, J = 3.7 Hz, 1H), 7.31 (d, J = 3.7 Hz, 1H), 4.61-4.57 (m, 1H), 2.05-1.97 (m, 2H), 1.87-1.80 (m, 2H), 1.59 (d, J = 4.2, 6.6 Hz, 3H), 1.34-1.28 (m, 2H), 1.23-1.17 (m, 2H), 0.92 (t, J = 7.3, 12.5 Hz, 3H), 0.00 (TMS) |
| 39 | 256.30 | 1.74 | (500 MHz, Methanol-d4) 8.85 (s, 1H), 8.79 (s, 1H), 8.47 (s, 1H), 7.84 (d, J = 3.7 Hz, 1H), 7.31 (d, J = 3.7 Hz, 1H), 4.21 (dd, J = 4.6, 9.5 Hz, 1H), 2.04-1.92 (m, 4H), 0.84 (t, J = 7.4 Hz, 3H), 0.00 (d, J = 3.1 Hz, H), |
| 40 | 300.40 | 1.40 | |
| 41 | 312.40 | 1.50 | |
| 42 | 326.40 | 1.40 | |
| 43 | 368.40 | 1.80 | |
| 44 | 327.40 | 1.20 | |
| 45 | 298.30 | 1.30 | |
| 46 | 347.10 | 1.20 | |
| 47 | 325.30 | 1.40 | |
| 48 | 347.40 | 1.30 | |
| 49 | 333.00 | 1.10 | |
| 50 | 325.40 | 1.10 | |

TABLE 3-continued

| Cpd # | M + H | RT | NMR |
|---|---|---|---|
| 51 | 312.40 | 1.40 | |
| 52 | 307.30 | 1.50 | |
| 53 | 350.30 | 1.90 | |
| 54 | 310.40 | 1.80 | CD3OD(H) 8.8 s (1H), 8.1 s (1H), 7.8 d (1H), 7.5 s (1H), 7.2 d (1H), 4.7 bs (1H), 4.5 bs (1H), 2.5 bs (1H), 2.2 bs (1H), 1.8 bs (1H), 1.6 bs (1H), 1.2 d (6H) |
| 55 | 324.30 | 1.70 | |
| 56 | 298.30 | 1.30 | |
| 57 | 300.00 | 1.90 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 3.4 (quin, 1H), 2.3 (m, 2H), 2.2 (m, 2H), 2.0 (dd, 1H), 1.9 (m, 1H) |
| 58 | 300.00 | 1.90 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 1.77 (m, 1H), 1.43 (m, 1H), 1.15 (m, 4H) 0.86 (m, 1H) |
| 59 | 312.00 | 1.90 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 5.7 (s, 2H), 3.4 (quin, 1H), 2.6 (m, 4H) |
| 60 | 330.00 | 1.90 | |
| 61 | 330.00 | 1.90 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 3.93 (d, 2H), 3.35 (t, 2H), 2.85 (m, 1H), 1.8 (m, 2H), 1.7 (m, 2H) |
| 62 | 342.00 | 2.40 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 1.95 (d, 2H), 1.78 (d, 2H), 1.5 (quar, 2H), 1.43 (m, 1H), 0.98 (quart, 2H), 0.89 (d, 3H) |
| 63 | 358.00 | 1.80 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 3.39 (s, 3H), 3.2 (m, 1H), 2.6 (, t, 1H), 2.25 (d, 1H), 2.05 (d, 1H), 1.83 (m, 1H), 1.3 (m, 2H), 1.07 (m, 1H) |
| 64 | 328.00 | 1.90 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 3.7 (m, 2H) |
| 65 | 342.00 | 1.60 | 500 MHz DMSO-d6: 12.4 (br s, 1H), 12.15 (s, 1H), 8.83 (s, 1H), 8.25 (s, 1H), 7.8 (s, 1H), 7.35 (s, 1H), 3.05 (m, 1H), 2.55 (m, 2H), 2.37 (m, 2H), 2.18 (m, 2H). 1.9 (m, 2H) |
| 66 | 316.00 | 2.10 | 500HMHz: DMSO-d6: 12.35 (br s, 1H), 12.15 (s, 1H), 8. (s, 1H), 8.2 (s, 1H), 7.68 (s, 1H), 7.43 (s, 1H), 2.33 (s, 2H), 1.07 (s, 9H) |
| 67 | 342.00 | 2.50 | 500HMHz: DMSO-d6: 12.35 (br s, 1H), 12.15 (s, 1H), 8. (s, 1H), 8.2 (s, 1H), 7.68 (s, 1H), 7.43 (s, 1H), 2.55 (m, 1H), 2.17 (m, 1H), 1.4-1.7 (cplx m, 8H), 1.1 (m, 3H) |
| 68 | 350.00 | 2.20 | |
| 69 | 300.00 | 1.80 | 500 MHz DMSO-d6: 12.27 (br s, 1H), 12.23 (s, 1H), 8.78 (s, 1H), 8.2 (s, 1H), 7.65 (m, 1H), 7.34 (m, 1H), 5.85 (m, 1H), 5.07 (dd, 1H), 5.0 (dd, 1H). 2.6 (t, 2H), 2.4 (t, 2H) |
| 70 | 300.00 | 1.70 | 500 MHz DMSO-d6: 12.27 (br s, 1H), 12.23 (s, 1H), 8.78 (s, 1H), 8.2 (s, 1H), 7.65 (m, 1H), 7.34 (m, 1H), 2.47 (d, 2H), 1.06 (m, 1H), 0.5 (m, 2H), 0.23 (m, 2H) |
| 71 | 316.00 | 1.40 | 500 MHz DMSO-d6: 12.27 (br s, 1H), 12.23 (s, 1H), 8.8 (s, 1H), 8.2 (s, 1H), 7.65 (m, 1H), 7.34 (m, 1H), 2.81 (t, 2H), 2.7 (t, 2H), 2.15 (s, 3H) |
| 72 | 316.00 | 2.10 | 500 MHz DMSO-d6: 12.27 (br s, 1H), 12.23 (s, 1H), 8.8 (s, 1H), 8.2 (s, 1H) 7.65 (m, 1H), 7.34 (m, 1H), 2.5 (t, 1H), 1.5 (m, 4H), 0.9 (d, 6H) |
| 73 | 297.30 | 1.61 | (500 MHz, DMSO-d6) 8.82 (s, 2H), 8.45 (s, 2H), 8.39 (d, J = 3.5 Hz, 1H), 7.77 (s, 1H), 7.19 (s, 1H), 5.07 (q, J = 7.2 Hz, 1H), 2.68-2.63 (m, 1H), 1.68 (d, 3H), 0.67-0.61 (m, 2H), 0.47-0.41 (m, 2H), 0.00 (TMS) |
| 74 | 313.30 | 2.30 | (500 MHz, DMSO-d6) 8.82 (d, J = 12.6 Hz, 2H), 8.43 (s, 1H), 8.22 (t, J = 5.7 Hz, 1H), 7.77 (s, 1H), 7.19 (s, 1H), 5.18 (q, J = 7.1 Hz, 1H), 3.02 (td, J = 6.6, 4.0 Hz, 1H), 2.98-2.88 (m, 2H), 1.77-1.67 (m, 2H), 0.88-0.79 (m, 6H) |
| 75 | 325.30 | 2.39 | (500 MHz, DMSO-d6) 8.87 (s, 1H), 8.83 (d, J = 6.5 Hz, 1H), 8.43 (s, 1H), 8.26 (d, J = 7.2 Hz, 1H), 7.77 (s, 1H), 7.19 (s, 1H), 5.12 (q, J = 7.1 Hz, 1H), 4.02-3.95 (m, 1H), 1.85-1.69 (m, 5H), 1.65-1.60 (m, 2H), 1.57-1.35 (m, 4H), −0.00 (d, J = 3.3 Hz, H), |
| 76 | 341.30 | 1.89 | (500 MHz, DMSO-d6) 8.88 (d, J = 6.1 Hz, 2H), 8.48 (s, 1H), 8.36-8.32 (m, 1H), 7.83 (s, 1H), 7.25 (s, 1H), 5.23 (td, J = 7.1, 5.5 Hz, 1H), 3.88-3.82 (m, 1H), 3.77-3.72 (m, 1H), 3.64-3.59 (m, 1H), 3.23-3.13 (m, 2H), 1.90-1.71 (m, 6H), 1.52-1.43 (m, 1H), −0.00 (d, J = 3.2 Hz, H), |
| 77 | 285.30 | 1.48 | (500 MHz, DMSO-d6) 8.88 (d, J = 6.1 Hz, 2H), 8.48 (s, 1H), 8.36-8.32 (m, 1H), 7.83 (s, 1H), 7.25 (s, 1H), 5.23 (td, J = 7.1, 5.5 Hz, 1H), 3.88-3.82 (m, 1H), 3.77-3.72 (m, 1H), 3.64-3.59 (m, 1H), 3.23-3.13 (m, 2H), 1.90-1.71 (m, 6H), 1.52-1.43 (m, 1H), −0.00 (d, J = 3.2 Hz, H), |
| 78 | 299.30 | 1.39 | (500 MHz, DMSO-d6) 8.84 (s, 1H), 8.80 (s, 1H), 8.43 (s, 1H), 8.16 (d, J = 7.5 Hz, 1H), 7.78 (s, 1H), 7.20 (s, 1H), 5.11 (q, J = 7.1 Hz, 1H), 3.86-3.80 (m, 1H), 1.75-1.69 (m, 3H), 1.08 (dd, J = 6.6, 11.6 Hz, 6H), −0.00 (d, J = 3.3 Hz, H), |

TABLE 3-continued

| Cpd # | M + H | RT | NMR |
|---|---|---|---|
| 79 | 315.30 | 1.40 | |
| 80 | 315.30 | 1.57 | (500 MHz, DMSO-d6) 8.79 (s, 1H), 8.75 (s, 1H), 8.39 (s, 1H), 8.30 (s, 1H), 7.72 (s, 1H), 7.13 (s, 1H), 5.18 (q, J = 7.1 Hz, 1H), 3.38-3.35 (m, 2H), 3.28-3.25 (m, 1H), 1.70 (d, J = 7.1 Hz, 2H), −0.00 (d, J = 3.2 Hz, H), |
| 81 | 315.30 | 1.59 | |
| 82 | 329.30 | 1.63 | |
| 83 | 329.30 | 1.69 | |
| 84 | 331.30 | 2.02 | (500 MHz, DMSO-d6) 8.83 (s, 1H), 8.80 (s, 1H), 8.43 (s, 1H), 8.36 (t, J = 5.5 Hz, 1H), 7.77 (s, 1H), 7.19 (s, 1H), 5.17 (q, J = 7.1 Hz, 1H), 3.34-3.24 (m, 2H), 2.56-2.50 (m, 2H), 2.06 (s, 3H), 175-1.72 (m, 3H), 0.00 (TMS) |
| 85 | 343.30 | 2.21 | (500 MHz, DMSO-d6) 8.82 (s, 1H), 8.79 (s, 1H), 8.42 (s, 1H), 8.21 (t, J = 5.4 Hz, 1H), 7.75 (s, 1H), 7.17 (s, 1H), 5.20 (q, J = 7.1 Hz, 1H), 3.56 (m, 1H), 3.41-3.35 (m, 2H), 3.27-3.17 (m, 2H), 1.76-1.70 (m, 4H), 1.02 (d, 6H), −0.00 (d, J = 3.3 Hz, H) |
| 86 | 347.30 | 2.69 | |
| 87 | 311.30 | 1.95 | (500 MHz, DMSO-d6) 8.85 (d, J = 11.1 Hz, 2H), 8.46 (s, 1H), 7.81 (s, 1H), 7.23 (d, J = 1.8 Hz, 1H), 5.51 (q, J = 7.0 Hz, 1H), 3.64-3.60 (m, 1H), 3.46-3.42 (m, 1H), 1.95-1.69 (m, 4H), 1.63 (d, J = 6.8 Hz, 3H), 0.04 (s, H), 0.00 (s, H), |
| 88 | 313.30 | 2.28 | (500 MHz, DMSO-d6) 8.87 (s, 1H), 8.84 (s, 1H), 8.46 (s, 1H), 7.82 (s, 1H), 7.25 (s, 1H), 5.65 (q, J = 6.9 Hz, 1H), 3.57-3.49 (m, 1H), 3.46-3.33 (m, 2H), 3.26-3.20 (m, 1H), 1.69 (d, J = 6.9 Hz, 3H), 1.13 (t, J = 7.1 Hz, 3H), 1.03 (t, J = 7.0 Hz, 3H), 0.00 (TMS) 0.00 (s, H), |
| 89 | 350.30 | 2.28 | (500 MHz, DMSO-d6) 8.87 (s, 1H), 8.81 (s, 1H), 8.55 (t, J = 5.2 Hz, 1H), 8.43 (s, 1H), 7.77 (s, 1H), 7.19 (s, 1H), 6.67 (s, 1H), 5.95 (s, 1H), 5.89-5.88 (m, 1H), 5.20 (q, J = 7.1 Hz, 1H), 4.32-4.24 (m, 2H), 3.59 (s, 3H), 1.68 (d, J = 6.9 Hz, 3H), 0.00 (s, H), |
| 90 | 299.30 | 1.89 | (500 MHz, DMSO-d6) 8.81 (s, 1H), 8.77 (s, 1H), 8.41 (s, 1H), 8.29 (d, J = 9.4 Hz, 1H), 7.74 (s, 1H), 7.16 (s, 1H), 5.14 (q, J = 7.1 Hz, 1H), 3.10-3.01 (m, 2H), 1.75-1.70 (m, 4H), 1.43 (qn, J = 7.2 Hz, 2H), 0.84 (t, J = 7.4 Hz, 3H), 0.00 (s, H), |
| 91 | 339.30 | 1.98 | (500 MHz, DMSO-d6) 8.94 (t, J = 6.3 Hz, 1H), 8.83 (d, J = 7.5 Hz, 2H), 8.44 (s, 1H), 7.78 (s, 1H), 7.20 (s, 1H), 5.28 (q, J = 7.2 Hz, 1H), 4.02-3.91 (m, 2H), 1.76-1.68 (d, 3H), 0.00 (TMS) |
| 92 | 284.20 | 2.13 | (500 MHz, CD3OD) 8.88 (s, 1H), 8.83 (s, 1H), 8.49 (s, 1H), 7.86 (d, J = 3.7 Hz, 1H), 7.34 (s, 1H), 4.33-4.27 (m, 1H), 2.06-1.86 (m, 4H), 1.40-1.23 (m, 3H), 0.96-0.82 (m, 5H), 0.00 (TMS) |
| 93 | 270.00 | 1.93 | (500 MHz, CD3OD) 8.87 (s, 1H), 8.80 (s, 1H), 8.47 (s, 1H), 7.87 (d, 1H), 7.32 (d, 1H), 4.59-4.55 (m, 1H), 2.05-1.99 (m, 1H), 1.94-1.84 (m, 2H), 1.61-1.58 (d, 2H), 1.39-1.27 (m, 3H), 1.15-1.13 (m, 1H), 1.03 dt, J = 6.6 Hz, 2H), 0.94-0.82 (m, 3H). |
| 94 | 270.00 | 1.93 | (500 MHz, CD3OD) 8.86 (s, 1H), 8.80 (s, 1H), 8.47 (s, 1H), 7.85 (d, 1H), 7.30 (d, 1H), 4.33 (m, 1H), 2.05-1.82 (m, 7H), 1.3 (m, 1H), 1.15 (m, 1H), 0.92 (t, J = 7.4 Hz, 3H), 0.83 (t, J = 7.4 Hz, 3H), 0.00 (m, H), |
| 95 | 314.30 | 1.95 | (500 MHz, DMSO-d6) 8.86 (d, J = 8.1 Hz, 2H), 8.45 (s, 1H), 7.79 (s, 1H), 7.18 (s, 1H), 5.30 (m, 1H), 1.76 (d, J = 7.3 Hz, 3H), 1.40 (s, 9H), 0.00 (TMS) |
| 96 | 314.00 | 2.00 | 500 MHz, DMSO-d6: 12.3br s, 1H), 12.2 (s, 1H), 8.78 (s, 1H), 8.18 (s, 1H) 7.65 (m, 1H), 7.34 (m, 1H), 2.5 (t, 2H), 1.53 (dt, 2H), 0.75 (m, 1H), 0.4 (dt, 2H), 0.09 (dt, 2H) |
| 97 | 304.00 | 1.50 | 500 MHz DMSO-d6: 12.24 (s, 1H), 8.78 (s, 1H), 8.23 (s, 1H), 7.65m, 1H), 7.42 (m, 1H), 4.1 (quart, 1H), 3.3 (s, 3H), 1.32 (D, 3H) |
| 98 | 316.00 | 2.00 | 500 MHz DMSO-d6: 12.24 (s, 1H), 8.78 (s, 1H), 8.23 (s, 1H), 7.65m, 1H), 7.32 (m, 1H), 2.3 (dd, 1H), 1.9 (sext, 1H), 1.39 (sept, 1H), 1.25 (m, 1H), 0.93 (d, 3H), 0.9 (t, 3H) |
| 99 | 342.00 | 1.90 | 500 MHz DMSO-d6: 12.24 (s, 1H), 8.78 (s, 1H), 8.23 (s, 1H), 7.65m, 1H), 7.32 (m, 1H), 2.83 (m, 2H), 2.68 (m, 2H) |
| 100 | 344.00 | 1.70 | 500 MHz DMSO-d6: 12.6 (s, 1H), 12.24 (s, 1H), 8.78 (s, 1H), 8.23 (s, 1H), 7.65m, 1H), 7.32 (m, 1H), 5.0 (quat, 1H), 4.4 (br m, 1H), |
| 101 | 352.00 | 1.70 | 500 MHz DMSO-d6: 12.25 (s, 1H), 12.20 (s, 1H), 8.78 (s, 1H), 8.23 (s, 1H), 7.65m, 1H), 7.55 (d, 2H), 7.45 (m, 1H), 7.36 (m, 2H), 7.31 (m, 1H), 5.35 (s, 1H) |
| 102 | 356.00 | 1.90 | 500 MHz DMSO-d6: 12.46 (s, 1H), 12.20 (s, 1H), 8.78 (s, 1H), 8.23 (s, 1H), 7.65m, 1H), 7.30 (m, 1H), 3.09 (m, 1H), 2.8 (m, 1H), 2.5 (m, 1H) |
| 103 | 344.00 | 2.30 | 500 MHz DMSO-d6: 12.4 (br m, 1H), 8.8 (s, 1H), 8.32 (s, 1H), 7.72 (m, 1H) 7.25 (m, 1H), 4.3 (t, 2H), 2.68 (d, 2H), 2.2 (sept, 1H), 1.83 (quin, 2H), 1.03 (t, 3H), 0.99 (d, 6H) |

TABLE 3-continued

| Cpd # | M + H | RT | NMR |
|---|---|---|---|
| 104 | 330.00 | 1.98 | 500 MHz DMSO-d6: 12.55 (br m, 1H), 8.88 (s, 1H), 8.4 (s, 1H), 7.75 (m, 1H) 7.25 (m, 1H), 4.4 (quart, 2H), 2.68 (d, 2H), 2.2 (sept, 1H), 1.4 (t, 3H), 1.0 (d, 6H) |
| 105 | 316.00 | 1.70 | 500 MHz DSMO-d6: 12.5 (br m, 1H), 8.85 (s, 1H), 8.36 (s, 1H), 7.7 (m, 1H), 7.30 (m, 1H), 3.82 (s, 3H), 2.68 (d, 2H), 2.17 (sept, 1H), 0.98 (d, 6H) |
| 106 | 228.20 | 1.43 | (500 MHz, DMSO-d6) 12.79 (s, 1H), 8.86 (d, J = 2.4 Hz, 2H), 8.44 (s, 1H), 7.81 (s, 1H), 7.20 (s, 1H), 4.23 (t, J = 7.0 Hz, 2H), 2.50 (qn, J = 1.7 Hz, DMSO-d6), 1.88 (qn, J = 7.2 Hz, 2H), 0.88 (t, J = 7.4 Hz, 3H), 0.00 (TMS) |
| 107 | 256.30 | 1.82 | (500 MHz, DMSO-d6) 12.68 (s, 1H), 8.84 (d, J = 7.5 Hz, 2H), 8.40 (s, 1H), 7.78 (s, 1H), 7.17 (d, J = 2.0 Hz, 1H), 4.28 (t, J = 7.3 Hz, 2H), 2.50 (qn, J = 1.8 Hz, DMSO-d6), 1.79-1.75 (m, 2H), 1.53 (qn, J = 6.7 Hz, 1H), 0.93 (d, J = 6.6 Hz, 6H), 0.00 (TMS) |
| 108 | 414.10 | 2.08 | |
| 109 | 364.10 | 1.90 | CD3CN (H) 10.4 s (1H), 9.9 s (1H), 8.7 s (1H), 7.9 s (1H0, 7.5 s (1H), 7.45 s(1H), 4.4 q (2H), 3.8 d (2H), 1.3 m (1H), 0.6 m (2H), 0.3 m (2H) |
| 110 | 378.10 | 1.90 | CD3CN (H) 10.4 s (1H), 9.9 s (1H), 8.7 s (1H), 7.9 s (1H0, 7.45 d (2H), 3.9 m (2H), 3.7 m (2H), 2.7 m (2H), 1.2 m (1H), 0.6 m (2H), 0.3 m (2H) |
| 111 | 357.10 | 1.70 | |
| 112 | 375.10 | 1.80 | |
| 113 | 391.10 | 1.90 | |
| 114 | 372.10 | 2.00 | |
| 115 | 335.10 | 1.60 | |
| 116 | 372.10 | 2.00 | |
| 117 | 357.20 | 1.95 | |
| 118 | 347.10 | 2.20 | |
| 119 | 296.00 | 1.40 | |
| 120 | 365.10 | 2.30 | |
| 121 | 353.10 | 2.21 | |
| 122 | 379.10; 379.30 | 2.30; 2.60 | |
| 123 | 415.10 | 2.50 | |
| 124 | 358.10 | 2.10 | |
| 125 | 336.10 | 1.80 | CD3CN (H) 11.0 s (1H), 8.9 S (1H), 7.9 d (1H), 7.7 d (1H), 7.3 d (1H), 7.2 d (1H), 4.0 m (2H), 3.7 m (2H), 2.8 t (2H), 1.2 m (1H), 0.6 m (2H), 0.4 m (2H) |
| 126 | 311.10 | 1.90 | CD3CN (H) 11.8 s (1H), 8.9 S (1H), 7.9 d (1H), 7.7 d (1H), 7.3 d (1H), 7.2 d (1H), 4.8 m (1H), 4.5 m (1H), 2.4 m (1H), 2.2 (1H), 1.8 m (1H), 1.7 m (1H), 1.3 m (3H), 1.1 m (3H) |
| 127 | 325.00 | 1.90 | |
| 128 | 342.00 | 2.60 | 500 MHz DMSO-d6: 13.8 (br m, 1H), 8.97 (s, 1H), 8.6 (s, 1H), 7.82 (s, 1H) 7.3 (s, 1H), 6.1 (m, 1H), 5.2 (d, J = 10, 1H), 5.1 (d, J = 17, 1H), 5.04 (br s, 1H) 3.6 (pair of m, 1H), 2.6 (d, 2H), 2.15 (sept, 1H), 0.98 (d, 6H) |
| 129 | 412.00 | 2.90 | |
| 130 | 201.10 | 0.87 | (500 MHz, DMSO-d6) 12.14 (s, 1H), 8.64 (s, 1H), 8.32 (s, 1H), 7.53 (d, 1H), 6.97 (d, 1H), 2.50 (t, J = 1.7 Hz, H), 0.00 (s, H), |
| 131 | 351.22 | 2.80 | CD3CN (H) 11.8 s (1H), 8.9 S (1H), 7.9 S (1H), 7.7 S (1H), 7.6 D (1H), 7.2 D (1H), 3.9 S (2H), 3.3 (2H), 2.6 d (2H), 1.0 m (1H), 0.5 m (2H), 0.2 m (2H) |
| 132 | 310.40 | 2.60 | CD3OD(H) 8.8 s (1H), 8.1 s (1H), 7.8 d (1H), 7.5 s (1H), 7.2 d (1H), 4.5 bs (2H), 2.2 bs (2H), 1.8 m (2H), 1.4 d (6H) |
| 133 | 286.20 | 1.20 | |
| 134 | 334.20 | 1.30 | |
| 135 | 361.40 | 1.60 | |
| 136 | 365.50 | 1.50 | |
| 137 | 348.30 | 2.00 | |
| 138 | 312.40 | 1.90 | |
| 139 | 348.20 | 1.70 | |
| 140 | 286.20 | 1.20 | |
| 141 | 216.90 | 0.39 | (500 MHz, Methanol-d4) 8.17 (d, J = 5.1 Hz, 1H), 7.48 (d, J = 5.1 Hz, 1H), 7.42 (d, J = 3.5 Hz, H1), 6.93 (d, J = 3.5 Hz, 1H) |
| 142 | 329.20 | 1.50 | (d6-DMSO) 12.54 (s, 1H), 11.87 (s, 1H), 8.29 (d, 1H), 7.97 (d, 1H), 7.62 (d, 1H), 7.59 (dd, 1H), 2.36 (dd, 1H), 2.14 (ddd, 1H), 1.51 (ddd, 1H), 1.27 (ddd, 1H) |
| 143 | 385.10 | 2.00 | |
| 144 | 371.50 | 1.90 | |
| 145 | 359.50 | 1.80 | |
| 146 | 317.20 | 1.50 | |
| 147 | 365.40 | 1.80 | (d6-DMSO) 12.71 (s, 1H), 11.79 (s, 1H), 8.28 (d, 1H), 8.03 (s, 1H), 7.94 (d, 1H), 7.69 (dd, 1H), 7.62 (m, 3H), 7.56 (dd, 1H), 7.13 (s, 1H) |
| 148 | 343.30 | 1.70 | |
| 149 | 383.40 | 2.00 | |

TABLE 3-continued

| Cpd # | M + H | RT | NMR |
|---|---|---|---|
| 150 | 399.50 | 2.30 | (d6-DMSO) 12.24 (s, 1H), 11.89 (s, 1H), 8.30 (d, 1H), 7.99 (s, 1H), 7.63 (d, 1H), 7.60 (dd, 1H), 7.12 (s, 1H), 5.58 (s, 3H), 2.68 (s, 2H), 2.57 (s, 2H), 1.62 (br s, 8H) |
| 151 | 385.50 | 2.10 | (d6-DMSO) 12.21 (s, 1H), 11.91 (s, 1H), 8.30 (d, 1H), 7.99 (s, 1H), 7.64 (d, 1H), 7.60 (dd, 1H), 7.14 (s, 1H), 3.55 (s, 3H), 3.14 (q, 1H), 2.85 (q, 1H), 2.10-1.35 (m, 8H) |
| 152 | 385.50 | 2.10 | (d6-DMSO) 12.35 and 12.21 (2s, 1H), 11.90 (s, 1H), 8.30 (d, 1H), 7.98 (s, 1H), 7.64 (d, 1H), 7.60 (dd, 1H), 7.13 (s, 1H), 3.13 (q, 1H), 2.85 (q, 1H), 2.09-1.36 (m, 8H) |
| 153 | 331.20 | 1.70 | (d6-DMSO) 12.35 and 12.21 (2s, 1H), 11.90 (s, 1H), 8.30 (d, 1H), 7.98 (s, 1H), 7.64 (d, 1H), 7.60 (dd, 1H), 7.13 (s, 1H), 3.13 (q, 1H), 2.85 (q, 1H), 2.09-1.36 (m, 8H) |
| 154 | 379.40 | 2.00 | (d6-DMSO) 12.79 (s, 1H), 11.84 (s, 1H), 8.30 (d, 1H), 8.06 (s, 1H), 7.93 (d, 1H), 7.76-7.65 (m, 3H), 7.63 (d, 1H), 7.57 (dd, 1H), 7.14 (s, 1H), 3.78 (s, 3H) |
| 155 | 395.50 | 2.00 | |
| 156 | 353.40 | 2.10 | |
| 157 | 373.50 | 2.10 | |
| 158 | 185.10 | 1.40 | (500 MHz, MeOD) 8.56 (s, H), 7.70 (t, J = 1.6 Hz, H), 7.40 (d, J = 3.6 Hz, H), 6.94-6.90 (m, 3H). |

TABLE 4

| Cpd # | M + H | RT | NMR |
|---|---|---|---|
| 159 | 342.00 | 0.94 | |
| 160 | 214.20 | 1.37 | (500 MHz, Methanol-d4) 8.87 (s, 1H), 8.39 (s, 1H), 8.09 (s, 1H), 7.64 (s, 1H), 4.08 (s, 3H), 3.31 (qn, J = 1.5 Hz, Methanol-d4), 2.38 (s, 3H), 0.00 (s, H) |
| 161 | 242.30 | 1.78 | (500 MHz, Methanol-d4) 8.87 (s, 1H), 8.44 (s, 1H), 8.11 (s, 1H), 7.64 (s, 1H), 4.30 (t, J = 6.9 Hz, 2H), 3.31 (qn, J = 1.6 Hz, Methanol-d4), 2.37 (s, 3H), 1.98 (qn, J = 7.2 Hz, 2H), 0.97 (t, J = 7.4 Hz, 3H), 0.00 (s, H) |
| 162 | 256.30 | 2.19 | (500 MHz, Methanol-d4) 8.88 (s, 1H), 8.44 (s, 1H), 8.11 (s, 1H), 7.64 (s, 1H), 4.16 (d, 2H), 2.38 (s, 3H), 2.37-2.26 (m, 1H), 0.98 (d, J = 6.7 Hz, 6H), 0.00 (s, H) |
| 163 | 270.30 | 2.83 | (500 MHz, Methanol-d4) 8.87 (s, 1H), 8.45 (s, 1H), 8.10 (s, 1H), 7.64 (s, 1H), 4.19 (t, J = 7.4 Hz, 2H), 3.31 (q, J = 1.4 Hz, H), 1.89-1.84 (m, 2H), 1.64-1.56 (m, 1H), 1.00 (dd, J = 2.7, 6.6 Hz, 6H), 0.00 (d, J = 2.8 Hz, H) |
| 164 | 290.30 | 2.26 | (500 MHz, Methanol-d4) 8.86 (s, 1H), 8.50 (s, 1H), 8.19 (s, 1H), 7.82 (s, 1H), 4.34 (t, J = 7.3 Hz, 2H), 3.31 (qn, J = 1.6 Hz, Methanol-d4), 1.87-1.83 (m, 2H), 1.60 (qn, J = 6.7 Hz, 1H), 1.03 (d, J = 6.6 Hz, 6H), 0.00 (s, H), |
| 165 | 262.20 | 1.78 | (500 MHz, Methanol-d4) 8.87 (s, 1H), 8.51 (s, 1H), 8.21 (s, 1H), 7.84 (s, 1H), 4.28 (t, J = 6.9 Hz, 2H), 3.31 (t, J = 1.5 Hz, H), 1.97 (qn, J = 7.2 Hz, 2H), 0.97 (t, J = 7.4 Hz, 3H), 0.00 (s, H) |
| 166 | 276.20 | 2.03 | (500 MHz, Methanol-d4) 8.90 (s, 1H), 8.52 (s, 1H), 8.22 (s, 1H), 7.89 (s, 1H), 4.13 (d, J = 7.3 Hz, 2H), 3.31 (q, J = 1.5 Hz, H), 2.33-2.25 (m, 1H), 0.97 (d, J = 6.6 Hz, 6H), 0.00 (s, H), |
| 167 | 328.30 | 1.50 | |
| 168 | 345.30 | 1.40 | |
| 169 | 371.50 | 1.50 | |
| 170 | 342.30 | 1.70 | |
| 171 | 387.50 | 1.70 | |
| 172 | 343.30 | 1.40 | |
| 173 | 433.50 | 1.80 | |
| 174 | 331.30 | 1.30 | |
| 175 | 352.50 | 2.00 | |
| 176 | 329.30 | 1.20 | (500 MHz, Methanol-d4) 8.95 (s, 1H), 8.54 (s, 1H), 7.87 (d, J = 3.6 Hz, 1H), 7.52 (d, J = 3.6 Hz, 1H), 3.49-3.40 (m, 2H), 3.17 (dd, J = 3.7, 8.5 Hz, 2H), 2.24-2.21 (m, 1H), 2.03-1.92 (m, 4H) |
| 177 | 429.50 | 2.10 | |
| 178 | 429.50 | 2.10 | |
| 179 | 407.30 | 1.60 | (500 MHz, DMSO-d6) 12.28 (s, 1H), 12.08 (s, 1H), 8.74 (d, J = 3.4 Hz, 1H), 8.14 (d, J = 3.0 Hz, H1), 7.60 (s, 1H), 7.30 (dd, J = 1.8, 3.3 Hz, 1H), 3.65-3.63 (m, 2H), 3.29 (s, 4H), 2.91 (s, 3H), 2.81 (t, J = 11.8 Hz, 2H), 2.73-2.68 (m, 1H), 2.02-2.00 (m, 2H), 1.76-1.68 (m, 2H) |
| 180 | 353.50 | 2.00 | |
| 181 | 353.50 | 2.00 | |
| 182 | 371.50 | 1.90 | |

TABLE 4-continued

| Cpd # | M + H | RT | NMR |
|---|---|---|---|
| 183 | 336.10 | 2.07 | CD3CN10.9 s (1H), 8.9 s (1H), 8.2 s (1H), 7.9 s (1H), 7.7 s (1H), 7.2 s (1H), 3.9 t (2H), 3.5 d (2H), 2.9 m (2H), 1.1-1.2 bs (1H), 0.6 m (2H), 0.4 s (2H) |
| 184 | 338.10 | 1.86 | H-DMSO-d6 (150C) 11.7 bs (1H), 11.3 bs (1H), 8.7 s (1H), 7.8 s (1H), 7.5 s (1H), 7.3 s (1H), 6.9 s (1H), 4.3 m (2H), 2.1 m (2H), 1.9 m (2H), 1.8 m (2H), 1.6 m (2H), 1.0 t (6H) |
| 185 | 338.00 | 1.90 | 300 MHz; DMSO-d6: 12.4 (br s, 1H), 12.2 (br s, 1H), 8.7 (s, 1H), 7.9 (s, 1H) 7.7 (s, 1H), 7.4 (s, 1H), 7.1 (s, 1H), 4.3m, 1H), 4.1 (m, 1H), 1.8 (m, 6H), 1.2 (m, 2H), 1.0 (m, 6H) |
| 186 | 392.30 | 2.30 | |
| 187 | 337.30 | 1.80 | |
| 188 | 392.30 | 2.30 | |
| 189 | 336.30 | 2.10 | |
| 190 | 362.40 | 2.30 | |
| 191 | 393.30 | 2.70 | |
| 192 | 338.30 | 2.10 | |
| 193 | 393.30 | 2.60 | |
| 194 | 339.00 | 2.60 | 500 MHz DMSO-d6: 12.34 (br s, 1H), 8.8 (s, 1H), 7.75 (s, 1H), 7.62 (m, 1H), 7.21 (m, 1H), 7.0 (s, 1H), 4.6 (m, 1H), 4.1 (m, 1H), 2.2 (m, 1H), 1.9 (m, 1H), 1.8 (m, 2H), 1.35 (d of m, 3H), 1.24 (m, 1H), 0.88 (m, 3H), 0.7 (m, 3H) |
| 195 | 365.40 | 2.50 | MeOD (H) 8.9 s (1H), 8.4 s (1H), 7.8 s (1H), 7.2 s (1H), 4.4 q (2H), 3.6 d (2H), 1.1 bs (1H), 0.6 (2H), 0.3 bs (2H) |
| 196 | 379.50 | 2.50 | MeOD (H) 8.8 s (1H), 8.2 s (1H), 7.7 s (1H), 7.6 s (1H), 7.1 s (1H), 3.9 m (2H), 3.5 m (2H), 2.7 m (2H), 1.1 bs (1H), 0.6 m (2H), 0.3 m (2H) |
| 197 | 311.40 | 2.10 | |
| 198 | 346.50 | 1.95 | (500 MHz, Methanol-d4) 8.84 (s, 1H), 7.88 (d, 1H), 7.85 (s, 1H), 7.3 (d, 1H), 3.85-3.55 (m, 4H), 1.75 (m, 2H), 1.45-1.52 (m, 5H), 1.0 (t, 3H) |
| 199 | 380.50 | 2.04 | (500 MHz, Methanol-d4) 8.82 (s, 1H), 7.9 (s, 2H), 7.83 (s, 1H), 7.40-7.28 (m, 5H), 4.97 (s, 2H), 3.65 (s, 2H) |
| 200 | 314.20 | 1.57 | |
| 201 | 326.30 | 2.01 | (500 MHz, DMSO-d6) 8.92 (s, 1H), 7.70 (s, 2H), 7.03 (s, 1H), 3.59-3.50 (m, 4H), 2.36- (s, 3H), 1.61 (m, 2H), 1.33 (q, J = 7.4 Hz, 2H), 0.92 (t, J = 7.3 Hz, 3H), 0.01--0.00 (m, H) |
| 202 | 360.30 | 2.05 | (500 MHz, DMSO-d6) 12.50 (s, 1H), 8.88 (s, 1H), 7.73 (s, 1H), 7.64 (s, 1H), 7.38 (t, J = 7.4 Hz, 2H), 7.33-7.28 (m, 3H), 4.84 (s, 2H), 3.56 (s, 2H), 2.36 (s, 3H), 1.21 (t, 3H), 0.00 (TMS) |
| 203 | 360.30 | 1.97 | |
| 204 | 322.20 | 1.84 | (500 MHz, DMSO-d6) 8.89 (s, 1H), 7.69-7.65 (m, 2H), 7.24 (d, J = 12.7 Hz, 1H), 5.93 (s, 1H), 5.84 (s, 1H), 5.27 (m, 1H), 4.92 (m, 1H), 2.35 (s, 3H), 1.38 (d, J = 6.2 Hz, 6H), 0.0 (TMS) |
| 205 | 326.30 | 1.99 | (500 MHz, DMSO-d6) 8.89 (s, 1H), 7.69-7.65 (m, 2H), 7.10 (s, 1H), 3.25 (m, 5H), 2.4 (s, 3H), 1.65 (m, 2H), 1.37-1.25 (m, 6H), 0.88 (t, 3H), 0.00 (TMS) |
| 206 | 312.30 | 1.87 | |
| 207 | 323.20 | 1.61 | (500 MHz, DMSO-d6) 8.87 (s, 1H), 7.69 (s, 1H), 7.63 (s, 1H), 7.10 (s, 1H), 3.82 (s, 2H), 3.58 (s, 2H), 2.90 (t, 2H), 2.35 (s, 3H), 1.24 (t, 3H), 0.00 (TMS) |
| 208 | 392.20 | 2.17 | (500 MHz, DMSO-d6) 8.87 (s, 1H), 7.69 (s, 1H), 7.63 (s, 1H), 7.10 (s, 1H), 3.82 (s, 2H), 3.58 (s, 2H), 2.90 (t, 2H), 2.35 (s, 3H), 1.24 (m, 5H), 0.00 (TMS) |
| 209 | 340.30 | 2.13 | (500 MHz, DMSO-d6) 8.94 (s, 1H), 7.71 (s, 2H), 7.00 (s, 1H), 3.85 (d, J = 12.4 Hz, 2H), 3.51 (s, 2H), 2.34 (s, 3H), 1.66-1.60 (m, 4H), 1.32 (q, J = 7.5 Hz, 2H), 0.91 (t, 3H), 0.00 (TMS) |
| 210 | 367.00 | 2.60 | |
| 211 | 381.00 | 2.80 | |
| 212 | 407.00 | 3.00 | |
| 213 | 344.10 | 1.82 | H DMSO-d6: 9.92 (s, 1H), 8.10 (s, 1H), 7.87 (s, 1H), 7.45 (s, 1H), 4.73-4.67 (m, 1H), 4.43-4.28 (m, 1H), 3.10-2.97 (m, 2H), 1.84-1.7 (m, 2H), 1.2 (d, 6H) |
| 214 | 318.00 | 2.20 | |
| 215 | 393.00 | 1.90 | 300 MHz; DMSO-d6: 12.6 (s, 1H), 8.8 (s, 1H), 7.8 (s, 1H), 7.7 (s, 1H), 7.3 (s, 1H), 7.0 (1H), 3.6 (m, 4H), 3.1 (m, 1H), 2.6 (m, 2H), 1.7 (m, 6H), |
| 216 | 379.00 | 1.90 | |
| 217 | 309.00 | 2.30 | 300 MHz, DMSO-d6: 12.35 (s, 1H), 8.79 (s, 1H), 7.71 (m, 1H), 7.53 (d, 1H), 7.20 (d, 1H), 6.98 (m, 1H), 5.93 (m, 2H), 5.25 (m, 4H), 4.17 (m, 4H) |
| 218 | 297.00 | 2.40 | |
| 219 | 283.00 | 2.20 | 300 MHz DMSO-d6: 12.3 (s, 1H), 8.7 (s, 1H), 7.7 (s, 2H), 7.6 (s, 1H), 7.35 (s, 1H), 7.0s, 1H), 3.9 (m, 2H) 1.97 (m, 4H) |
| 220 | 373.00 | 2.80 | |
| 221 | 326.00 | 2.50 | |
| 222 | 373.00 | 2.80 | |

TABLE 4-continued

| Cpd # | M + H | RT | NMR |
|---|---|---|---|
| 223 | 406.30 | 2.01 | |
| 224 | 324.30 | 1.61 | |
| 225 | 392.30 | 1.89 | |
| 226 | 349.30 | 1.55 | |
| 227 | 412.20 | 2.26 | DMSO d-6: 8.82 (s, 1H), 7.92 (s, 1H), 7.73 (s, 1H), 7.26 (s, 1H), 3.82 (m, 2H), 3.58 (m, 2H), 2.78-2.62 (m, 2H), 1.1 (m, 1H), 0.60-0.54 (m, 2H), 0.34-0.28 (m, 2H) |
| 228 | 378.30 | 1.88 | (CD3CN) 11.2 s (1H), 9.0 s (1H), 8.2 s 91H), 7.9 s (1H), 7.6 s (1H), 7.2 s (1H), 4.6 t (2H), 3.9 s (3H), 37 d (2H), 1.1 m (1H), 0.6 m (2H), 0.2 m (2H) |
| 229 | 379.00 | 2.60 | 300 MHz; DMSO-d6: 12.45 (s, 1H), 8.9 (s, 1H), 8.85 (s, 1H), 7.75 (m, 2H), 7.08 (m, 1H), 3.83 (m, 2H), 3.52 (m, 2H), 2.72 (m, 2H), 1.12 (m, 1H), 0.55 (m, 2H), 0.3 (m, 2H) |
| 230 | 378.00 | 2.20 | 300 MHz; DMSO-d6: 12.45 (s, 1H), 8.9 (s, 1H), 8.85 (s, 1H), 7.75 (m, 2H), 7.08 (m, 1H), 3.83 (m, 4H), 3.0 (m, 2H), 2.75 (m, 2H) |
| 231 | 365.00 | 2.60 | 300 MHz; DMSO-d6: 12.4 (s, 1H), 8.93 (s, 1H), 8.82 (s, 1H), 7.82 (s, 1H), 7.7 (m, 1H), 7.04 (m, 1H), 3.6 (m, 2H), 1.1 (m, 1H), 0.5 (m, 2H). 0.3 (m, 2H) |
| 232 | 326.30 | 2.20 | |
| 233 | 314.20 | 1.50 | |
| 234 | 298.20 | 1.80 | |
| 235 | 324.20 | 2.00 | |
| 236 | 294.20 | 1.80 | |
| 237 | 323.30 | 1.70 | |
| 238 | 392.20 | 2.60 | |
| 239 | 331.10 | 1.82 | CDCl3: 9.0 (s, 1H), 8.16 (d, 1H), 7.62 (s, 1H), 7.60 (d, 1H), 4.8 (m, 1H), 3.67 (m, 1H), 1.3 (m, 10H) |
| 240 | 412.20 | 2.43 | CDCl3: 8.94 (s, 1H), 8.16 (s, 1H), 7.55 (s, 1H), 7.40 (s, 1H), 4.27 (m, 2H), 3.90 (m, 2H), 2.76 (m, 1H), 2.15 (m, 2H), 1.95-1.78 (m, 4H). |
| 241 | 426.20 | 2.47 | CDCl3: 8.94 (s, 1H), 8.21 (s, 1H), 7.63 (s, 1H), 7.52 (s, 1H), 3.80 (m, 4H), 2.80-2.65 (m, 1H), 2.68-2.45 (m, 2H), 2.20-2.05 (m, 2H), 1.95-1.78 (m, 4H). |
| 242 | 411.20 | 1.95 | CDCl3: 8.94 (s, 1H), 8.05 (s, 1H), 7.66 (s, 1H), 7.45 (s, 1H), 4.0 (m, 4H), 2.93 (t, 2H), 2.75-2.65 (m, 2H). |
| 243 | 371.30 | 1.89 | CDCl3: 9.05 (s, 1H), 8.05 (s, 1H), 7.60 (s, 1H), 7.40 (s, 1H), 3.9-3.7 (m, 2H), 3.66-3.45 (m, 2H), 2.67-2.48 (m, 2H),, 2.20-2.02 (m, 1H), 1.0 (d, 6H). |
| 244 | 414.20 | 2.34 | CDCl3: 9.02 (s, 1H), 8.05 (s, 1H), 7.60 (s, 1H), 7.40 (s, 1H), 3.88-3.7 (m, 2H), 3.66-3.45 (m, 2H), 2.67-2.50 (m, 2H),, 2.18-2.02 (m, 1H), 0.95 (d, 6H). |
| 245 | 309.00 | 2.20 | 300 MHz, DMSO-d6: 12.4 (s, 1H), 8.9 (s, 1H), 8.8 (s, 1H), 7.7 (m, 1H), 7.66 (s, 1H), 7.0 (m, 1H), 5.93 (m, 2H), 5.25 (m, 4H), methylenes obscured by water peak |
| 246 | 339.00 | 2.60 | 300 MHz, acetone-d6: 11.5 (s, 1H), 8.8 (s, 1H), 8.74 (s, 1H), 7.84 (s, 1H), 7.73 (m, 1H), 7.08 (m, 1H), 4.55 (m, 1), 4.18 (m, 1H), 3.1 (m4H), 1.44 (m, 4H), 0.9 (m, 6H) |
| 247 | 367.00 | 2.50 | 300 MHz, DMCSO-d6: 12.4 (s, 1H), 8.88 (s, 1H), 8.78 (s, 1H), 7. (m, 1H), 7.63 (s, 1H), 7.07 (m, 1H), 4.55 (m, 1H), 3.6 (m, 2H), 2.6 (m, 2H) |
| 248 | 373.00 | 2.70 | |
| 249 | 311.00 | 210 | 300 MHz; DMSO-d6: 12.5 (s, 1H), 8.92 (m, 1H), 8.84 (s, 1H), 7.75 (m, 1H), 7.71 (s, 1H), 7.01 (m, 1H), 4.76 (m, 1H), 2.27 (m, 1H), 1.7 (m, 2H), 1.56 (m, 1H), 1.34 (d, 3H), 1.28 (d, 1.5H), 1.05 (d, 1.5H) |
| 250 | 393.00 | 2.80 | |
| 251 | 379.00 | 2.80 | |
| 252 | 381.00 | 2.70 | 300 MHz-DMSO-d6: 12.95 (br s, 1H), 9.07 (s, 1H), 8.94 (s, 1H), 7.89 (m, 2H), 7.22 (m, 1H), 3.7 (m, 2H), 3.4 (m, 2H), 2.6 (m, 2H), 1.8 (m, 1H), 0.89 (d, 6H) |
| 253 | 240.00 | 1.75 | (CDCl3, 300 MHz) 10.19 (s, 1H), 8.99 (s, 1H), 8.15 (s, 1H), 8.02 (d, 1H), 7.80-7.44 (m, 3H), 6.92 (d, 1H) |
| 254 | 328.0 | 2.50 | (300 MHz, DMSO-d6) 12.37 (s, 1H), 8.88 (s, 1H), 8.75 (s, 1H), 8.38 (s, 1H), 7.70-7.22 (m, 4H), 7.05 (s, 1H), 5.59 (s, 2H) |

Example 8

JAK3 Inhibition Assay

Compounds were screened for their ability to inhibit JAK3 using the assay shown below. Reactions were carried out in a kinase buffer containing 100 mM HEPES (pH 7.4), 1 mM DTT, 10 mM $MgCl_2$, 25 mM NaCl, and 0.01% BSA. Substrate concentrations in the assay were 5 µM ATP (200 uCi/µmole ATP) and 1 µM poly(Glu)$_4$Tyr. Reactions were carried out at 25° C. and 1 nM JAK3.

To each well of a 96 well polycarbonate plate was added 1.5 µl of a candidate JAK3 inhibitor along with 50 µl of kinase buffer containing 2 µM poly(Glu)$_4$Tyr and 10 µM ATP. This was then mixed and 50 µl of kinase buffer containing 2 nM JAK3 enzyme was added to start the reaction. After 20 minutes at room temperature (25° C.), the reaction was stopped with 50 µl of 20% trichloroacetic acid (TCA) that also contained 0.4 mM ATP. The entire contents of each well were then transferred to a 96 well glass fiber filter plate using a TomTek Cell Harvester. After washing, 60 µl of scintillation fluid was added and $^{33}$P incorporation detected on a Perkin Elmer TopCount.

Example 9

JAK2 Inhibition Assay

The assays were as described above in Example 36 except that JAK-2 enzyme was used, the final poly(Glu)$_4$Tyr concentration was 15 µM, and final ATP concentration was 12 µM.

Tables 5 and 6 depict enzyme inhibition data ($K_i$) for certain exemplary compounds. Compound numbers in Tables 5 and 6 correspond to those compounds depicted in Tables 1 and 2, respectively. In Tables 5 and 6, "A" represents a $K_i$ of less than 0.1 µM, "B" represents a $K_i$ of between 0.1 and ≤0.5 µM, "C" represents a $K_i$ of >0.5 µM and less than 5.0 µM and "D" represents a $K_i$ of >5.0 µM.

TABLE 5

| Cpd# | JAK2 | JAK3 |
| --- | --- | --- |
| 1 |  | A |
| 2 | B | B |
| 3 | B | B |
| 4 | C | B |
| 5 | B | B |
| 6 | A | B |
| 7 | A | A |
| 8 | A | B |
| 9 | A | A |
| 10 | A | A |
| 11 | A | B |
| 12 | A | B |
| 13 | A | A |
| 14 | A | B |
| 15 | A | A |
| 16 | A | A |
| 17 | A | A |
| 18 | A | A |
| 19 | A | A |
| 20 | A | A |
| 21 | A | A |
| 22 | A | A |
| 23 | A | A |
| 24 | A | B |
| 25 | A | B |
| 26 | A | A |
| 27 | A | B |
| 28 | A | B |
| 29 | A | A |
| 30 | A | A |
| 31 | A | A |
| 32 | A | A |
| 33 | A | B |
| 34 | A | A |
| 35 | A | A |
| 36 | A | A |
| 37 | A | A |
| 38 | A | A |
| 39 | A | A |
| 40 | A | B |
| 41 | B | C |
| 42 | B | C |
| 43 | C | C |
| 44 | C | C |
| 45 | C | C |
| 46 | B | B |
| 47 | B | B |
| 48 | A | A |
| 49 | A | B |
| 50 | C | C |

TABLE 5-continued

| Cpd# | JAK2 | JAK3 |
| --- | --- | --- |
| 51 | B | C |
| 52 | A | B |
| 53 | A | B |
| 54 | A | A |
| 55 | A | B |
| 56 | B | C |
| 57 | A | A |
| 58 | A | A |
| 59 | A | A |
| 60 | A | A |
| 61 | A | A |
| 62 | A | B |
| 63 | A | B |
| 64 | A | A |
| 65 | A | A |
| 66 | A | A |
| 67 | A | A |
| 68 | A | A |
| 69 | A | A |
| 70 | A | A |
| 71 | A | B |
| 72 | A | A |
| 73 | B | B |
| 74 | B | A |
| 75 | B | A |
| 76 | C | C |
| 77 | B | C |
| 78 | B | B |
| 79 | C | B |
| 80 | C | B |
| 81 | C | C |
| 82 | B | B |
| 83 | C | B |
| 84 | B | B |
| 85 | C | C |
| 86 | B | B |
| 87 | B | B |
| 88 | B | A |
| 89 | A | B |
| 90 | B | A |
| 91 | A | A |
| 92 | A | A |
| 93 | A | A |
| 94 | A | A |
| 95 | B | V |
| 96 | A | A |
| 97 | A | B |
| 98 | A | A |
| 99 | A | A |
| 100 | A | A |
| 101 | A | A |
| 102 | A | A |
| 103 | A | A |
| 104 | A | A |
| 105 | A | A |
| 106 | A | B |
| 107 | A | B |
| 108 | A | A |
| 109 | A | A |
| 110 | A | A |
| 111 | A | A |
| 112 | A | A |
| 113 | A | A |
| 114 | A | A |
| 115 | A | A |
| 116 | A | A |
| 117 | A | B |
| 118 | A | A |
| 119 | A | A |
| 120 | A | A |
| 121 | A | A |
| 122 | A | A |
| 123 | A | A |
| 124 | A | B |
| 125 | A | A |
| 126 | A | A |
| 127 | A | A |
| 128 | A | A |

TABLE 5-continued

| Cpd# | JAK2 | JAK3 |
|------|------|------|
| 129 | A | B |
| 130 | B | B |
| 131 | A | A |
| 132 | A | B |
| 133 | A | B |
| 134 | A | A |
| 135 | A | A |
| 136 | A | B |
| 137 | A | B |
| 138 | A | A |
| 139 | A | B |
| 140 | A | B |
| 141 | C | C |
| 142 | C | C |
| 143 | B | B |
| 144 | B | B |
| 145 | B | B |
| 146 | B | B |
| 147 | B | C |
| 148 | A | B |
| 149 | A | B |
| 150 | A | B |
| 151 | A | B |
| 152 | A | B |
| 153 | B | B |
| 154 | B | B |
| 155 | A | B |
| 156 | A | B |
| 157 | A | B |
| 158 | | |

TABLE 6

| Cpd# | JAK2 | JAK3 |
|------|------|------|
| 159 | C | D |
| 160 | B | B |
| 161 | B | B |
| 162 | A | B |
| 163 | A | B |
| 164 | A | B |
| 165 | A | B |
| 166 | A | B |
| 167 | A | A |
| 168 | A | B |
| 169 | A | A |
| 170 | A | B |
| 171 | A | A |
| 172 | A | B |
| 173 | A | A |
| 174 | A | B |
| 175 | A | B |
| 176 | A | A |
| 177 | B | B |
| 178 | B | B |
| 179 | A | A |
| 180 | B | B |
| 181 | B | B |
| 182 | A | B |
| 183 | A | A |
| 184 | A | B |
| 185 | A | B |
| 186 | A | B |
| 187 | A | A |
| 188 | A | B |
| 189 | A | A |
| 190 | B | C |
| 191 | A | A |
| 192 | A | A |
| 193 | A | A |
| 194 | A | A |
| 195 | A | B |
| 196 | A | B |
| 197 | A | C |
| 198 | A | A |
| 199 | A | A |
| 200 | B | C |
| 201 | A | B |
| 202 | A | B |
| 203 | A | B |
| 204 | A | B |
| 205 | A | B |
| 206 | A | B |
| 207 | A | B |
| 208 | A | A |
| 209 | A | B |
| 210 | A | A |
| 211 | A | A |
| 212 | A | A |
| 213 | A | A |
| 214 | A | A |
| 215 | A | A |
| 216 | A | A |
| 217 | A | A |
| 218 | A | B |
| 219 | B | C |
| 220 | A | B |
| 221 | C | C |
| 222 | A | A |
| 223 | A | A |
| 224 | A | B |
| 225 | A | A |
| 226 | A | A |
| 227 | A | A |
| 228 | A | A |
| 229 | A | B |
| 230 | A | B |
| 231 | A | A |
| 232 | A | B |
| 233 | A | C |
| 234 | A | C |
| 235 | A | A |
| 236 | A | B |
| 237 | A | A |
| 238 | A | B |
| 239 | A | B |
| 240 | A | A |
| 241 | A | B |
| 242 | A | A |
| 243 | A | A |
| 244 | A | B |
| 245 | A | B |
| 246 | A | B |
| 247 | B | C |
| 248 | A | B |
| 249 | | |
| 250 | A | B |
| 251 | B | B |
| 252 | B | B |
| 253 | C | B |
| 254 | | |

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound selected from any one of the following structural formulae or a pharmaceutically acceptable salt thereof:
7
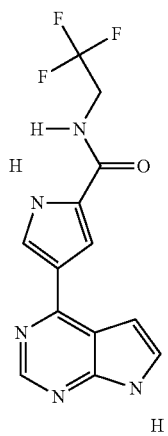
8
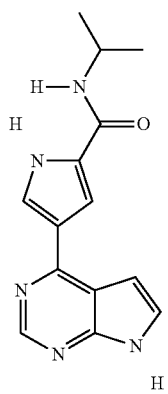
9
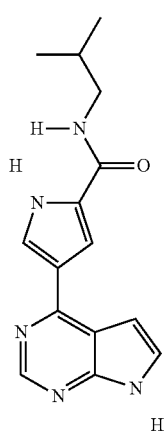
10
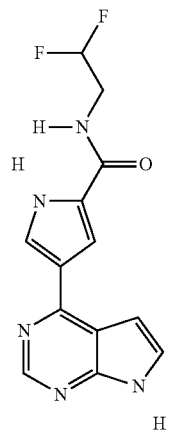
11
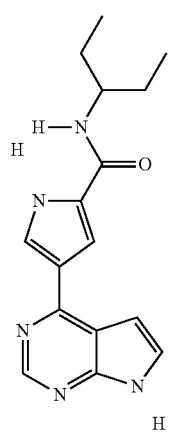
12
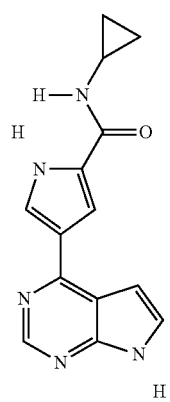

13
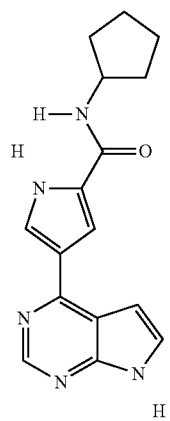
14
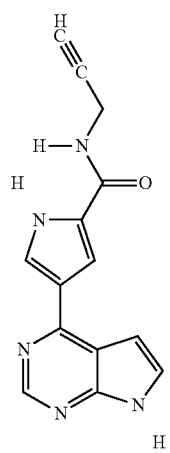
15
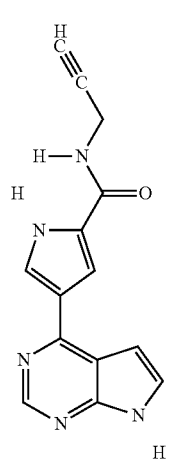
16
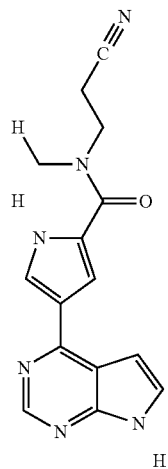
17
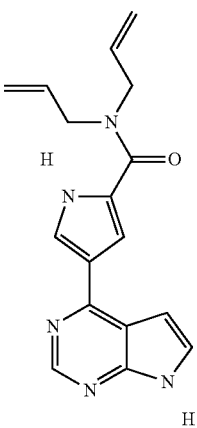
18
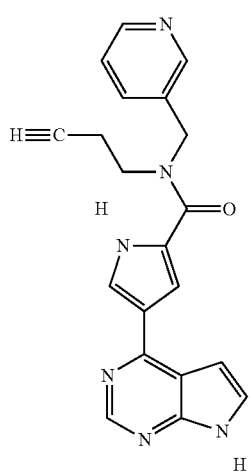

-continued
| | |
|---|---|
| 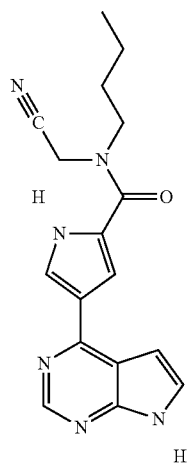 19 | 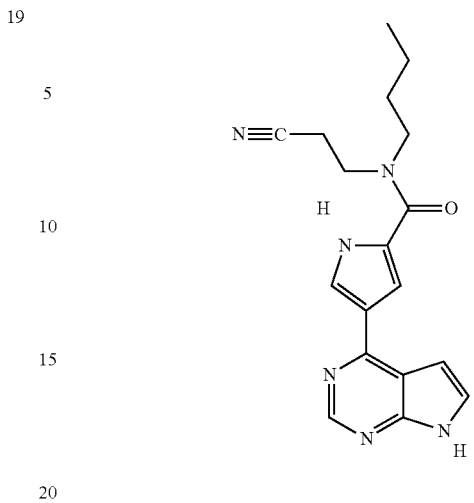 22 |
| 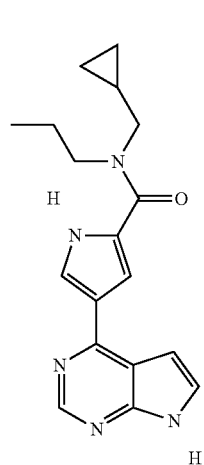 20 | 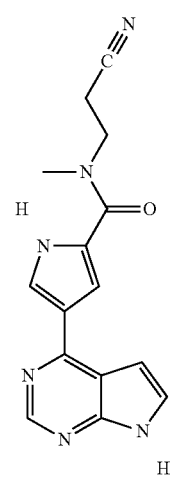 23 |
| 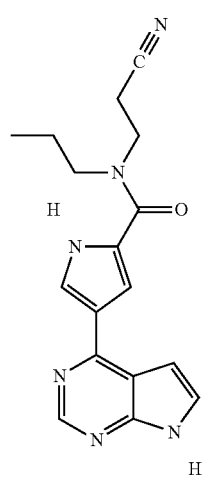 21 | 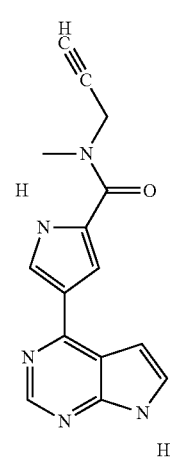 24 |

147 -continued
25
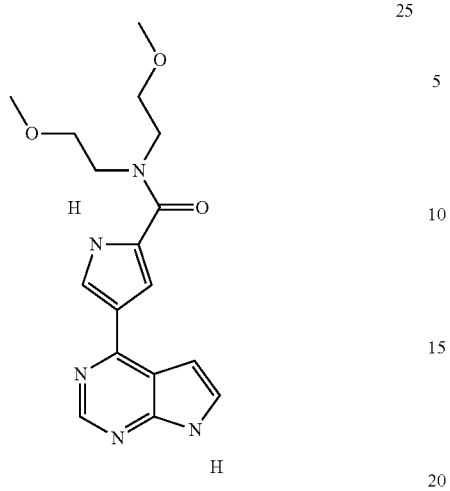
26
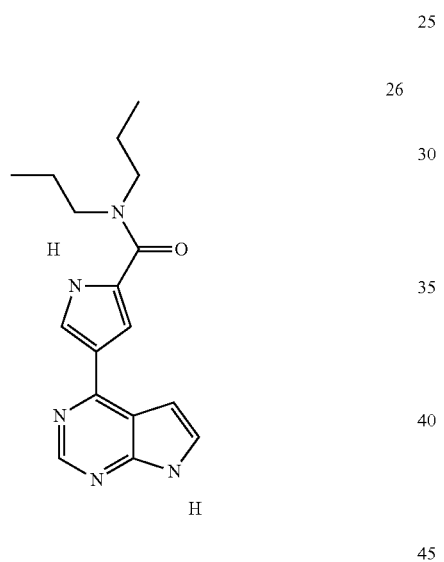
27
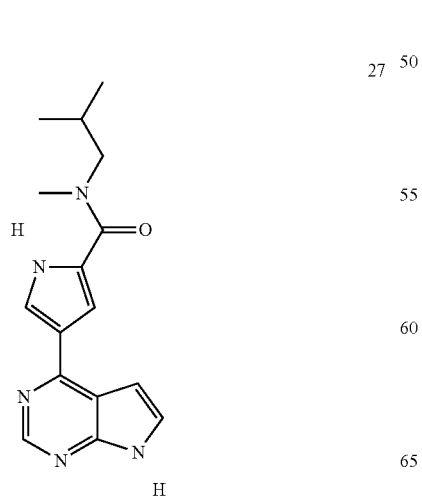
148 -continued
28
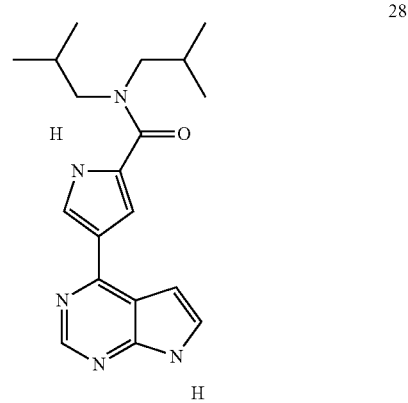
29
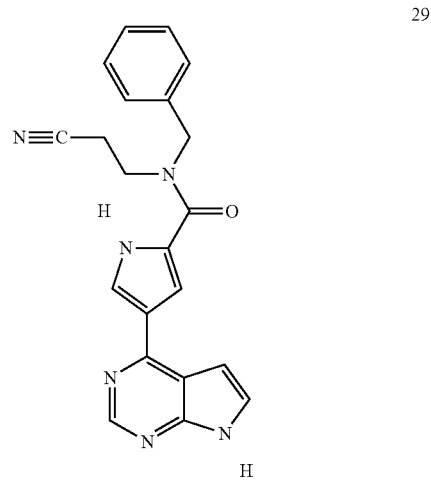
30
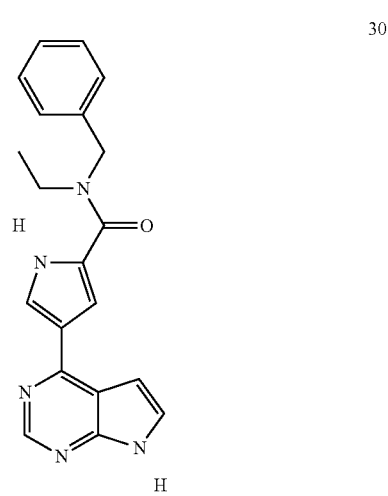

| 40 | 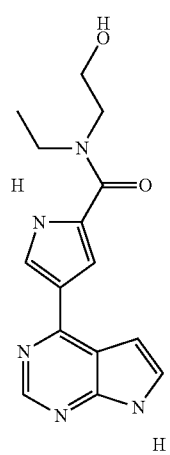 | 43 | 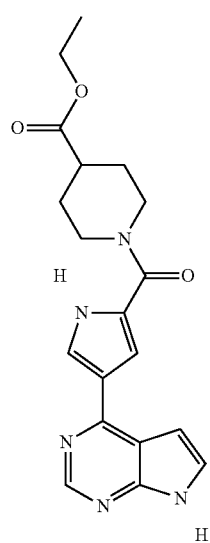 |
| 41 | 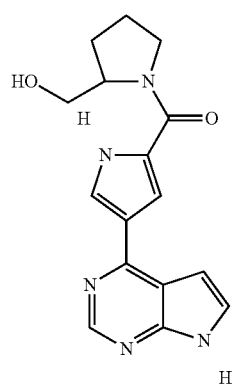 | 44 | 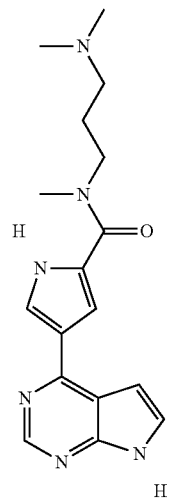 |
| 42 | 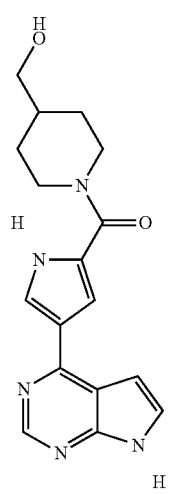 | 45 | 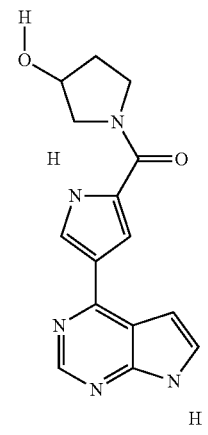 |

| 46 | 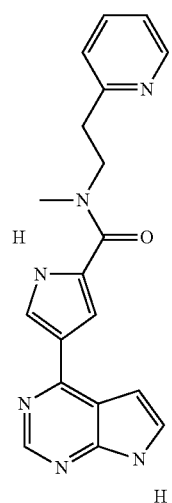 | 49 | 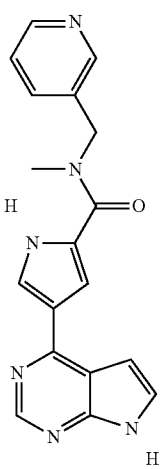 |
|---|---|---|---|
| 47 | 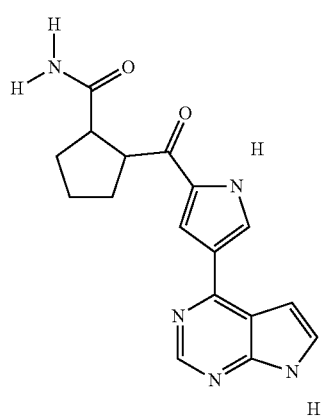 | 50 | 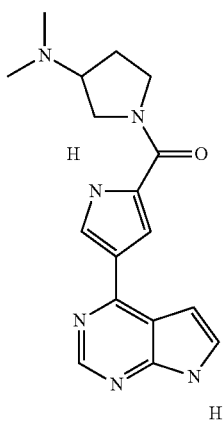 |
| | | 51 | 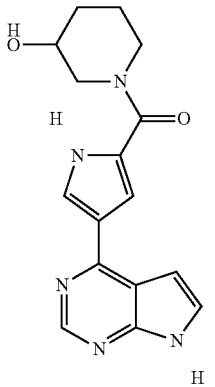 |
| 48 | | 52 | 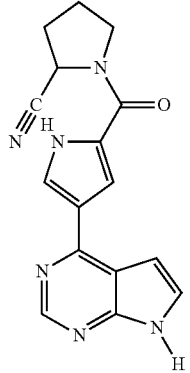 |

| 153 -continued | | 154 -continued | |
|---|---|---|---|
| 53 | 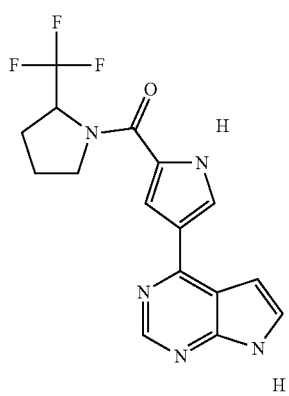 | 108 | 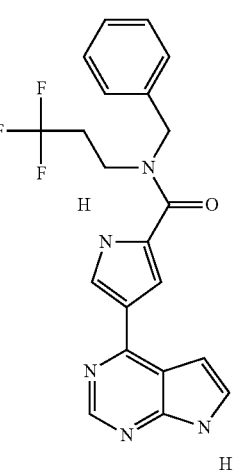 |
| 54 | | | |
| 55 | | 109 | 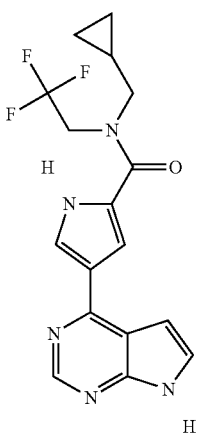 |
| 56 | | 110 | 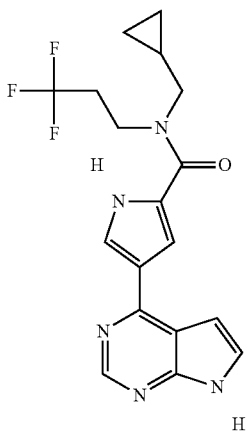 |

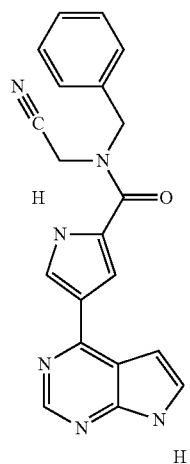 111
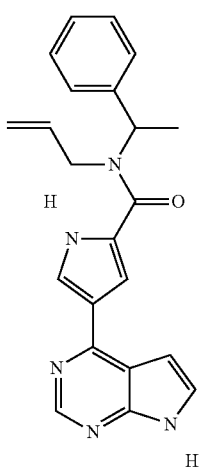 114
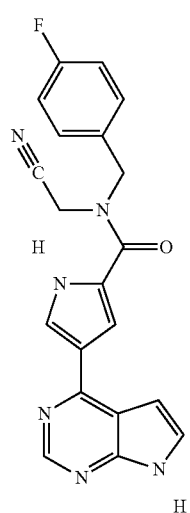 112
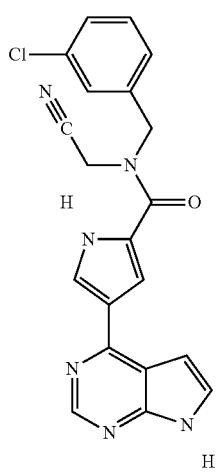 115
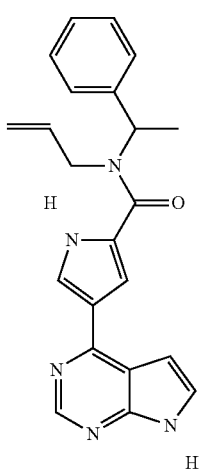 113
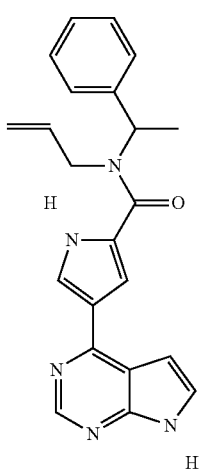 116

157 -continued | 158 -continued

2. A compound selected from any one of the following structural formulae or a pharmaceutically acceptable salt thereof:
138
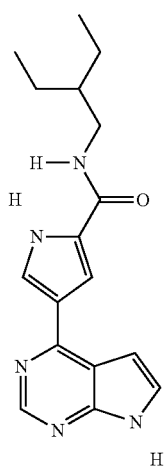
139
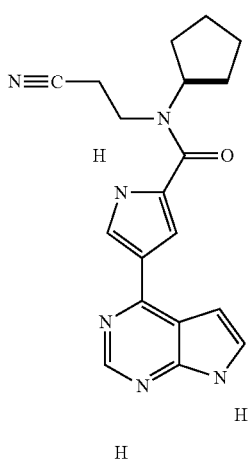
140
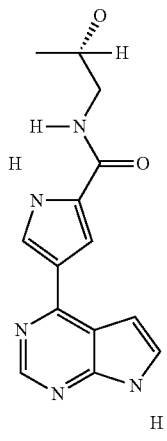
158
184
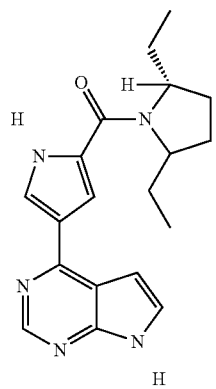
185
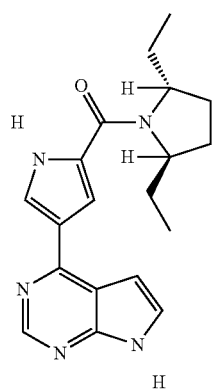
186
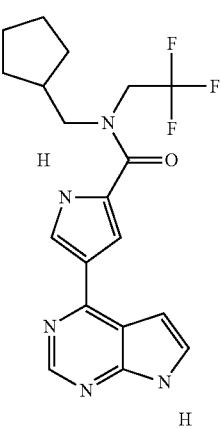

| | |
|---|---|
| 187 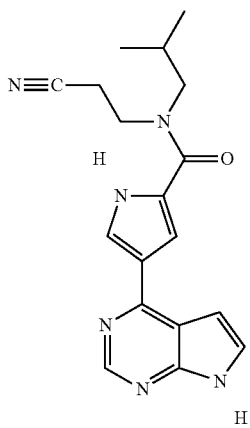 | 198 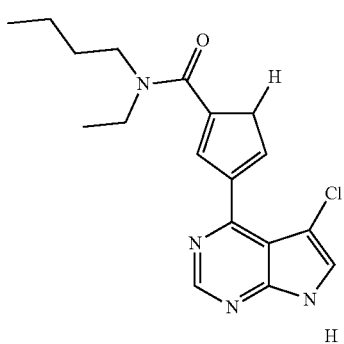 |
| 188 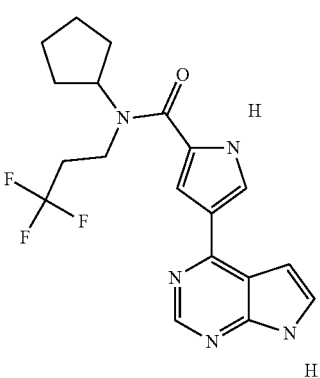 | 199 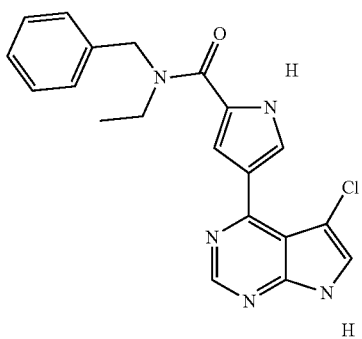 |
| 189 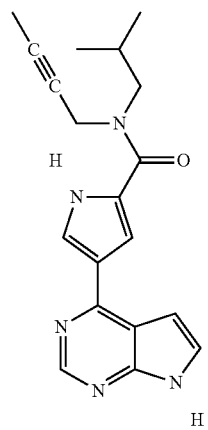 | 200 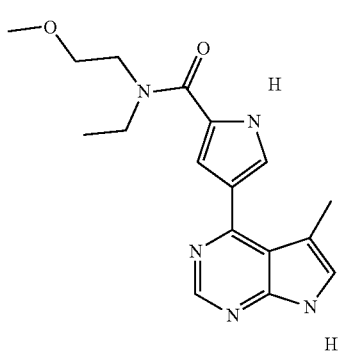 |
| 190 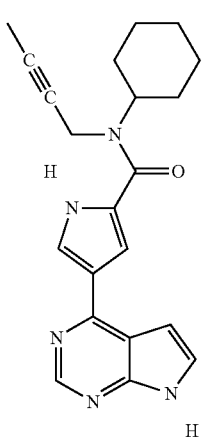 | 201 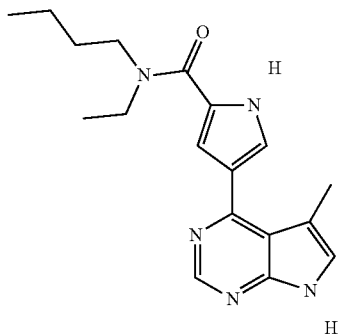 |

| | |
|---|---|
| 202 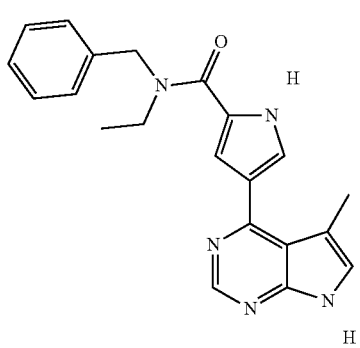 | 206 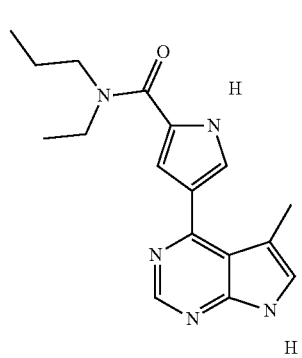 |
| 203 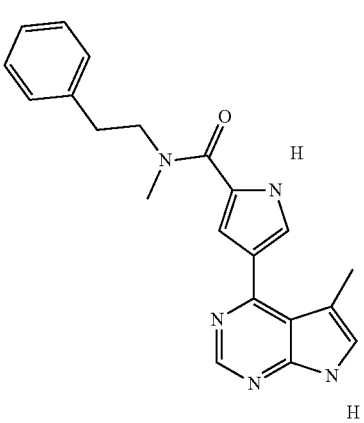 | 207 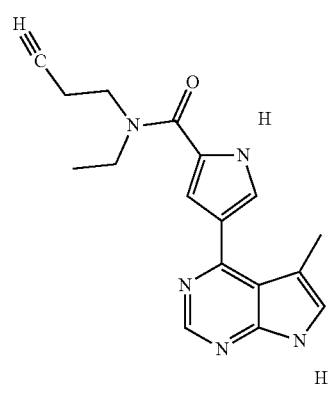 |
| 204 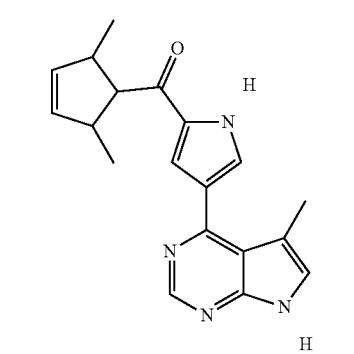 | 208 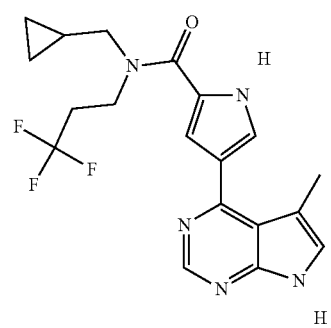 |
| 205 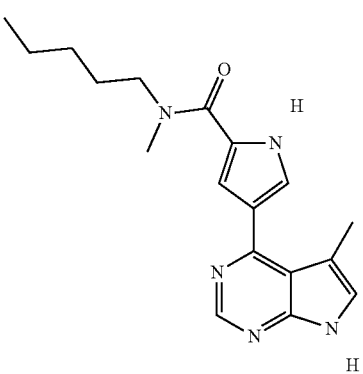 | 209 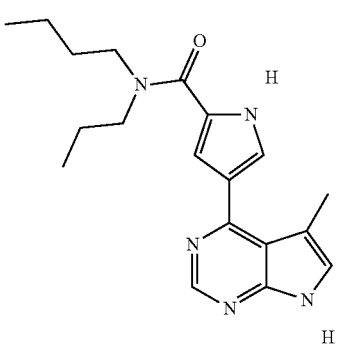 |

| 165 -continued | | 166 -continued | |
|---|---|---|---|
| 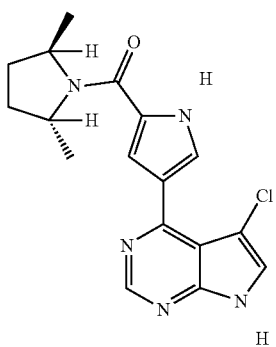 | 213 | 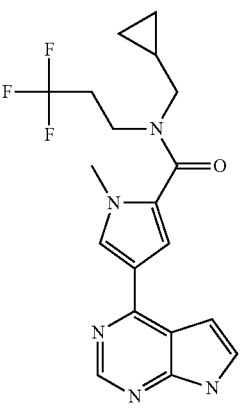 | 225 |
| 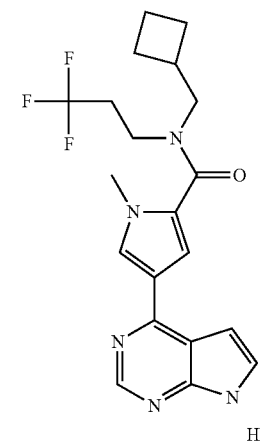 | 214 | 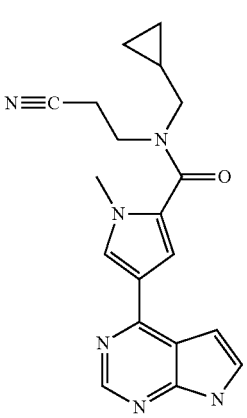 | 226 |
| | 223 | 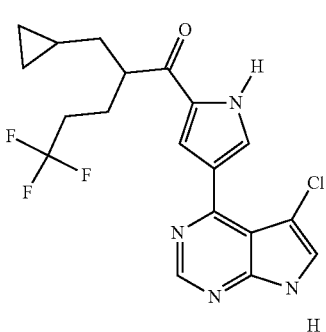 | 227 |
| 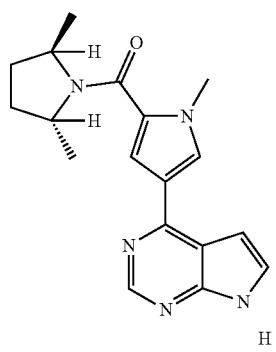 | 224 | 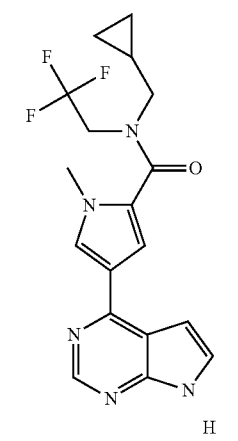 | 228 |

| 167 -continued | | 168 -continued | |
|---|---|---|---|
| | 232 | 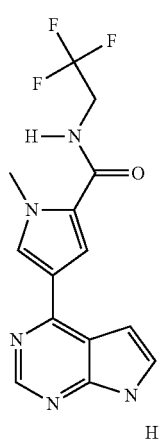 | 235 |
| | 233 | 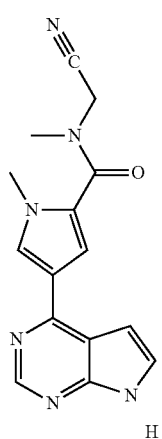 | 236 |
| 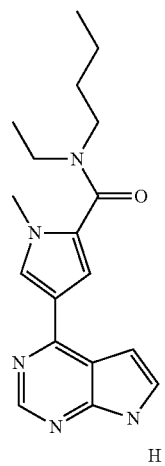 | 234 | 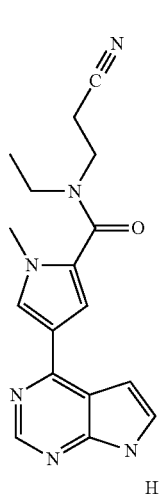 | 237 |

-continued

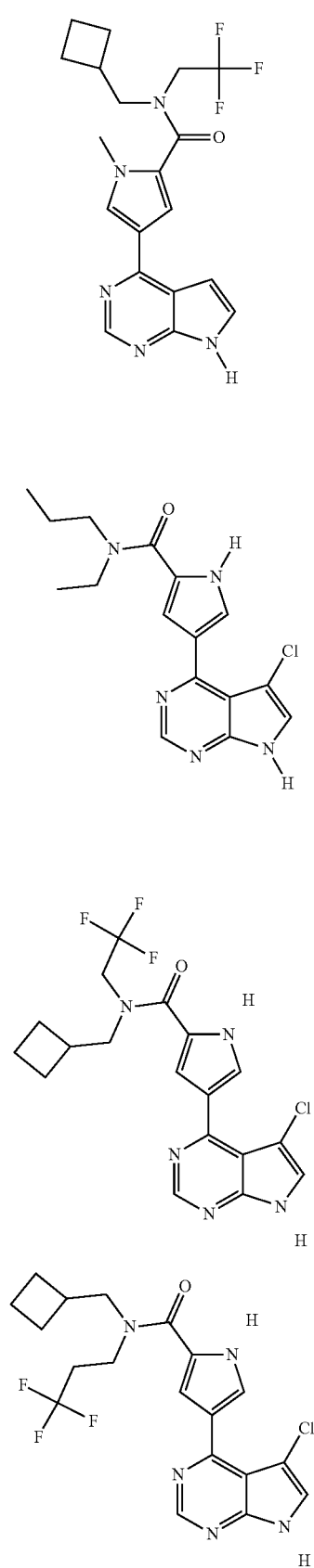

-continued

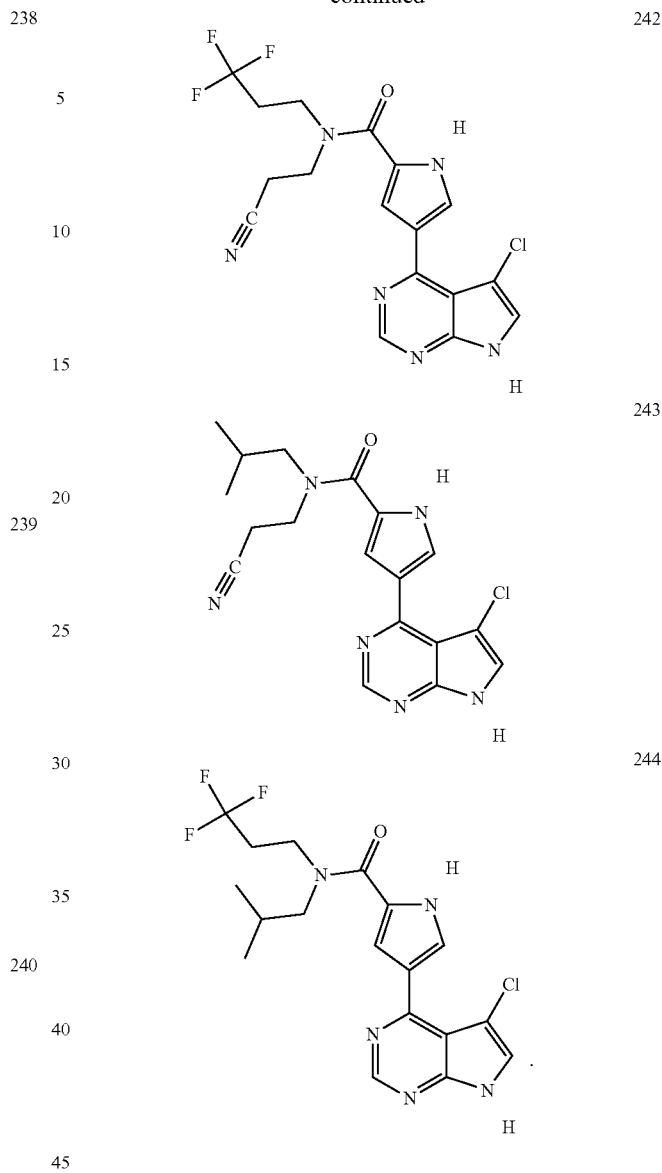

3. A pharmaceutical composition comprising a compound according to claim 1, and a pharmaceutically acceptable carrier, adjuvant, or vehicle.

4. The composition according to claim 3, additionally comprising a therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders.

5. A pharmaceutical composition comprising a compound according to claim 1, and a pharmaceutically acceptable carrier, adjuvant, or vehicle.

6. A pharmaceutical composition comprising a compound according to claim 2, and a pharmaceutically acceptable carrier, adjuvant, or vehicle.

* * * * *